US010688315B2

(12) United States Patent
Medendorp, Jr. et al.

(10) Patent No.: US 10,688,315 B2
(45) Date of Patent: Jun. 23, 2020

(54) PHOTOTHERAPY DEVICES FOR TREATMENT OF DERMATOLOGICAL DISORDERS OF THE SCALP

(71) Applicant: Know Bio, LLC, Durham, NC (US)

(72) Inventors: Nicholas William Medendorp, Jr., Raleigh, NC (US); Gerald H. Negley, Chapel Hill, NC (US); Matthew Carl Reynolds, Chapel Hill, NC (US); James Michael Lay, Apex, NC (US)

(73) Assignee: Know Bio, LLC, Durham, NC (US)

( * ) Notice: Subject to any disclaimer, the term of this patent is extended or adjusted under 35 U.S.C. 154(b) by 384 days.

(21) Appl. No.: 15/222,292

(22) Filed: Jul. 28, 2016

(65) Prior Publication Data

US 2017/0028216 A1    Feb. 2, 2017

Related U.S. Application Data

(60) Provisional application No. 62/197,736, filed on Jul. 28, 2015.

(51) Int. Cl.
*A61N 5/06* (2006.01)
*A61B 90/00* (2016.01)
*A61B 18/00* (2006.01)

(52) U.S. Cl.
CPC .. *A61N 5/0616* (2013.01); *A61B 2018/00642* (2013.01); *A61B 2018/00791* (2013.01);
(Continued)

(58) Field of Classification Search
None
See application file for complete search history.

(56) References Cited

U.S. PATENT DOCUMENTS 5,228,431 A   7/1993 Giarretto
5,549,639 A   8/1996 Ross
(Continued)

FOREIGN PATENT DOCUMENTS

AU   2016100390 A4   7/2016
CN   101687101 A    3/2010
(Continued)

OTHER PUBLICATIONS

International Preliminary Report on Patentability for PCT/US2016/044403, dated Feb. 8, 2018, 8 pages.
(Continued)

*Primary Examiner* — Carl H Layno
*Assistant Examiner* — Dacheng Xie
(74) *Attorney, Agent, or Firm* — Nexsen Pruet, LLC; David S. Bradin

(57) ABSTRACT

Modulated light therapy devices for treatment of dermatological disorders of the scalp are provided. An exemplary device includes a flexible printed circuit board (FPCB) supporting at least one light emitting device having an emitter height. The FPCB includes multiple interconnected panels and bending regions defined in and between at least some of the interconnected panels as to allow the FPCB to be configured in a concave shape to cover at least a portion of a cranial vertex of the patient. At least one light-transmissive layer proximate to the FPCB is configured to transmit (e.g., incoherent) light emissions generated by at least one light emitting device. At least one standoff is configured to be arranged between the FPCB and the scalp of the patient, wherein the at least one standoff includes a standoff height that exceeds the emitter height.

14 Claims, 34 Drawing Sheets

(52) U.S. Cl.
CPC ... *A61B 2090/033* (2016.02); *A61B 2090/061* (2016.02); *A61B 2090/065* (2016.02); *A61B 2090/0804* (2016.02); *A61B 2090/0814* (2016.02); *A61N 5/0617* (2013.01); *A61N 2005/063* (2013.01); *A61N 2005/0633* (2013.01); *A61N 2005/0647* (2013.01); *A61N 2005/0652* (2013.01); *A61N 2005/0662* (2013.01)

(56) References Cited

U.S. PATENT DOCUMENTS

| | | | |
|---|---|---|---|
| 5,616,140 A * | 4/1997 | Prescott | A61N 5/0616 606/10 |
| 6,096,066 A | 8/2000 | Chen et al. | |
| 6,171,332 B1 | 1/2001 | Whitehurst | |
| 6,283,956 B1 | 9/2001 | McDaniel | |
| 6,290,713 B1 | 9/2001 | Russell | |
| 6,443,978 B1 | 9/2002 | Zharov | |
| 6,497,719 B2 | 12/2002 | Pearl et al. | |
| 6,645,230 B2 | 11/2003 | Whitehurst | |
| 6,663,659 B2 | 12/2003 | McDaniel | |
| 6,676,655 B2 | 1/2004 | McDaniel | |
| 6,887,260 B1 | 5/2005 | McDaniel | |
| 6,918,922 B2 | 7/2005 | Oron | |
| 6,936,044 B2 | 8/2005 | McDaniel | |
| 6,955,684 B2 | 10/2005 | Savage, Jr. et al. | |
| 6,989,023 B2 | 1/2006 | Black | |
| 7,201,764 B2 | 4/2007 | Pearl et al. | |
| 7,201,765 B2 | 4/2007 | McDaniel | |
| 7,267,673 B2 | 9/2007 | Pilcher et al. | |
| 7,303,578 B2 | 12/2007 | De Taboada et al. | |
| 7,304,201 B2 | 12/2007 | Holloway et al. | |
| 7,309,348 B2 | 12/2007 | Streeter et al. | |
| 7,494,503 B2 | 2/2009 | McDaniel | |
| D599,954 S | 9/2009 | Michaels et al. | |
| D631,604 S | 1/2011 | Michaels et al. | |
| D635,686 S | 4/2011 | Tucker et al. | |
| D639,751 S | 6/2011 | Tucker et al. | |
| D640,793 S | 6/2011 | Britt | |
| 8,053,977 B2 | 11/2011 | Lifka et al. | |
| 8,146,607 B2 | 4/2012 | Rabin et al. | |
| 8,192,473 B2 | 6/2012 | Tucker et al. | |
| 8,252,033 B2 | 8/2012 | Tucker et al. | |
| 8,518,029 B2 | 8/2013 | Birmingham et al. | |
| 8,556,951 B2 | 10/2013 | Witt et al. | |
| 8,641,702 B2 | 2/2014 | Pilcher et al. | |
| 8,651,111 B2 | 2/2014 | McDaniel | |
| 8,747,446 B2 | 6/2014 | Chen et al. | |
| 8,758,215 B2 | 6/2014 | Legendre et al. | |
| 8,771,327 B2 | 7/2014 | Pearl et al. | |
| D712,561 S | 9/2014 | Hagenauer | |
| 8,845,704 B2 | 9/2014 | Dunning et al. | |
| D716,493 S | 10/2014 | Michaels et al. | |
| 8,900,282 B2 | 12/2014 | Brawn | |
| 8,900,283 B2 | 12/2014 | Johnson et al. | |
| 9,017,391 B2 | 4/2015 | McDaniel | |
| 9,040,103 B2 | 5/2015 | Marrot et al. | |
| 9,132,279 B2 | 9/2015 | Roersma et al. | |
| 9,144,690 B2 | 9/2015 | McDaniel | |
| 9,192,780 B2 | 11/2015 | McDaniel | |
| 9,215,921 B2 | 12/2015 | Thiebaut et al. | |
| 9,227,082 B2 | 1/2016 | McDaniel | |
| D754,897 S | 4/2016 | Michaels et al. | |
| 9,308,389 B2 | 4/2016 | Brawn | |
| 9,415,237 B2 | 8/2016 | Wagenaar Cacciola et al. | |
| D777,339 S | 1/2017 | Chen | |
| 9,545,524 B2 | 1/2017 | Maas et al. | |
| 9,554,963 B2 | 1/2017 | Pilcher et al. | |
| 9,561,386 B2 | 2/2017 | Pearl et al. | |
| 9,616,013 B2 | 4/2017 | Casasanta, III et al. | |
| 9,636,522 B2 | 5/2017 | Oversluizen et al. | |
| 9,724,536 B1 | 8/2017 | Rabin et al. | |
| D804,047 S | 11/2017 | Michaels et al. | |
| 2002/0128648 A1 | 9/2002 | Weber et al. | |
| 2003/0076281 A1 * | 4/2003 | Morgan | F24C 7/004 345/44 |
| 2003/0130709 A1 | 7/2003 | D.C. et al. | |
| 2003/0167080 A1 | 9/2003 | Hart et al. | |
| 2003/0236487 A1 | 12/2003 | Knowlton | |
| 2004/0044384 A1 | 3/2004 | Leber et al. | |
| 2004/0073079 A1 | 4/2004 | Altshuler et al. | |
| 2004/0162596 A1 | 8/2004 | Altshuler et al. | |
| 2005/0045189 A1 | 3/2005 | Jay | |
| 2006/0227844 A1 * | 10/2006 | Guenter | H01S 5/18388 372/101 |
| 2006/0258896 A1 | 11/2006 | Haber et al. | |
| 2006/0287696 A1 * | 12/2006 | Wright | A61N 5/0613 607/88 |
| 2007/0060819 A1 | 3/2007 | Altshuler et al. | |
| 2007/0106856 A1 | 5/2007 | Nomura et al. | |
| 2007/0185553 A1 | 8/2007 | Kennedy | |
| 2007/0208396 A1 | 9/2007 | Whatcott et al. | |
| 2007/0213792 A1 | 9/2007 | Yaroslavsky et al. | |
| 2007/0233208 A1 | 10/2007 | Kurtz et al. | |
| 2008/0033516 A1 | 2/2008 | Altshuler et al. | |
| 2008/0269849 A1 | 10/2008 | Lewis | |
| 2008/0319430 A1 | 12/2008 | Zenzie et al. | |
| 2009/0254156 A1 | 10/2009 | Powell et al. | |
| 2009/0318802 A1 | 12/2009 | Boyden | |
| 2010/0004645 A1 | 1/2010 | Jeong et al. | |
| 2010/0049180 A1 | 2/2010 | Wells et al. | |
| 2010/0076529 A1 | 3/2010 | Tucker et al. | |
| 2010/0106077 A1 * | 4/2010 | Rabin | A61N 5/0616 604/20 |
| 2010/0204762 A1 | 8/2010 | De Taboada et al. | |
| 2010/0242155 A1 | 9/2010 | Carullo, Jr. | |
| 2010/0331928 A1 | 12/2010 | Dunning et al. | |
| 2011/0015707 A1 | 1/2011 | Tucker et al. | |
| 2011/0054573 A1 | 3/2011 | Mitchell | |
| 2011/0144410 A1 | 6/2011 | Kennedy | |
| 2011/0144727 A1 | 6/2011 | Benedict | |
| 2011/0160814 A2 | 6/2011 | Tucker et al. | |
| 2011/0264174 A1 | 10/2011 | McNeill et al. | |
| 2011/0301673 A1 | 12/2011 | Hoffer et al. | |
| 2012/0059440 A1 | 3/2012 | Hamid | |
| 2012/0065709 A1 | 3/2012 | Dunning et al. | |
| 2013/0041432 A1 | 2/2013 | Tucker et al. | |
| 2013/0131762 A1 | 5/2013 | Oversluizen et al. | |
| 2013/0144364 A1 | 6/2013 | Wagenaar Cacciola et al. | |
| 2014/0128941 A1 * | 5/2014 | Williams | A61N 5/06 607/88 |
| 2014/0128942 A1 | 5/2014 | Bembridge et al. | |
| 2014/0148879 A1 | 5/2014 | Mersch | |
| 2014/0243933 A1 | 8/2014 | Ginggen | |
| 2014/0276248 A1 | 9/2014 | Hall et al. | |
| 2014/0303693 A1 | 10/2014 | Haarlander et al. | |
| 2014/0350643 A1 | 11/2014 | Pepitone et al. | |
| 2015/0005854 A1 | 1/2015 | Said | |
| 2015/0112411 A1 | 4/2015 | Beckman et al. | |
| 2015/0297914 A1 | 10/2015 | Hamid et al. | |
| 2016/0051835 A1 | 2/2016 | Tapper et al. | |
| 2016/0106999 A1 | 4/2016 | Michaels et al. | |
| 2016/0271420 A1 * | 9/2016 | Pina | A61N 5/0617 |

FOREIGN PATENT DOCUMENTS

| | | |
|---|---|---|
| CN | 102247656 A | 11/2011 |
| CN | 102348425 A | 2/2012 |
| CN | 102380169 A | 3/2012 |
| CN | 203169848 U | 9/2013 |
| CN | 103930162 A | 7/2014 |
| EP | 2508229 A1 | 10/2012 |
| EP | 3069762 A1 | 9/2016 |
| WO | 2004033040 A1 | 4/2004 |
| WO | 2008131343 A1 | 10/2008 |
| WO | 2008144157 A1 | 11/2008 |
| WO | 2013036558 A1 | 3/2013 |
| WO | 2014146029 A1 | 9/2014 |
| WO | 2015006309 A1 | 1/2015 |

(56) References Cited

OTHER PUBLICATIONS

Author Unknown, "Theradome Laser Helmet Review—A 120 Day Continuous Journal," Prevent Hair Loss Products, Jan. 14, 2014, retrieved Jun. 27, 2017, https://web.archive.org/web/20140610024017/http://preventhairlossproducts.com:80/theradome-laser-helmet-review-120-day-continuous-journal/, pp. 1-4.
International Search Report and Written Opinion for PCT/US2016/44403, dated Dec. 16, 2016, 11 pages.
Theradome Laser Helmet Review—A 120 Day Continuous Journal—Prevent Hair Loss Pr . . . —(https://web.archive.org/web/20140610024017/http://preventhairloss products.com/theradome-laser-helmet- review-120-day-continuous-journal/.
Beyakirthi, Sharnika, "Nitric oxide," DermNet NZ, 2009, 4 pages, http://www.dermnetnz.org/topics/nitric-oxide/.
Andrew, Penelope J. et al., "Enzymatic function of nitric oxide synthases," Cardiovascular Research, vol. 43, No. 3, Aug. 15, 1999, pp. 521-531.
Author Unknown, "Brilliant Light Therapy," In Light Wellness Systems, eBrochure, Date Unknown, 5 pages.
Author Unknown, "Healed by Light," Digi-Key Electronics, Jul. 1, 2014, 4 pages, http://www.digikey.com/es/articles/techzone/2014/jul/healed-by-light.
Author Unknown, "illuMask," La Lumiere, Date Unknown, 2 pages, http://www.illumask.com/dimming/.
Author Unknown, "Near-IR Photoluminescent Dyes for Molecular Labeling," NanoQuantum, Technology, 2013, 7 pages, http://www.nanoquantum.com/Technology .html.
Author Unknown, "Philips Blue Touch," Koninklijke Philips NV., Version 1.0.1, Sep. 1, 2013, 2 pages.
Author Unknown, "Ultraviolet Light Therapy," Wound Care Centers, Date Unknown, 3 pages, http://www.woundcarecenters.org/article/wound-therapies/ultraviolet-light-therapy.
Author Unknown, "What is Light Therapy used for?" Rio, The Dezac Group, Ltd, Date Unknown, 4 pages, http://www.lightmask.com/uses_for_lt.htm#top.
Avci, Pinar et al., "Low-Level Laser (Light) Therapy (LLL T) for Treatment of Hair Loss," Lasers in Surgery and Medicine, vol. 46, 2014, pp. 144-151.
Avci, Pinar et al., "Low-Level Laser (Light) Therapy (LLL T) in Skin: Stimulating, Healing, Restoring," Seminars in Cutaneous Medicine and Surgery, vol. 32, No. 1, 2013, pp. 41-52.
Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.
Barolet, Daniel, "Light-Emitting Diodes (LEOs) in Dermatology," Seminars in Cutaneous Medicine and Surgery, vol. 27, No. 4, Dec. 1, 2008, pp. 227-238.
Cals-Grierson, M.-M. et al., "Nitric oxide function in the skin," Nitric Oxide, vol. 10, No. 4, Jun. 2004, pp. 179-193.
Chaves, Maria Emilia De Abreu et al., "Effects of low-power light therapy on wound healing: Laser x LED," Anais Brasileiros de Dermatologia, vol. 89, No. 4, Jul./Aug. 2014, pp. 616-623.
Farivar, Shirin et al., "Biological Effects of Low Level Laser Therapy," Journal of Lasers in Medical Sciences, vol. 5, No. 2, Spring 2014, pp. 58-62.
Feelisch, Martin et al., "Concomitant S-, N-, and heme-nitrosis{yl}ation in biological tissues and fluids: implications for the fate of NO in vivo," FASEB, vol. 16, No. 13, Nov. 2002, pp. 1775-1785.
Gupta, Asheesh et al., "History and Fundamentals of Low-Level Laser {Light) Therapy," Handbook of Photomedicine, Chapter 5, CRC Press, 2014, pp. 43-52.
Hamblin, Michael R et al., "Mechanisms of Low Level Light Therapy," Proceedings of the SPIE, vol. 6140, Feb. 10, 2006, pp. 614001-1 to 641001-12.
Hamblin, Michael R, "Mechanisms of Low Level Light Therapy," Aug. 14, 2008, 22 pages, http://photobiology_info//Hamblin.html.
Hamblin, Michael R, The Role of Nitric Oxide in Low Level Light Therapy, Proceedings of SPIE, vol. 6846, 2008, p. 684602-1 to 684602-14.
Karu, Tiina I., "Low-Power Laser Therapy," Biomedical Photonics Handbook, Chapter 48, CRC Press, 2003, pp. 8-1 to 48-25.
Kirima, Kazuyoshi et al., "Evaluation of systemic blood NO dynamics by EPR spectroscopy: HbNO as an Endogenous index of NO," American Journal of Physiology Heart and Circulatory Physiology, vol. 285, No. 2, Aug. 2003,pp. H589-H596.
Kovacs, Izabella et al., "Nitric oxide-based protein modification: formation and site-specificity of protein nitrosylation," Frontiers in Plant Science, vol. 4, Article 137, May 14, 2013, 10 pages.
Leong, Mimi, "Effects of Light-Emitiing Diode Photostimulation on Burn Wound Healing," thesis, The University of Texas Graduate School of Biomedical Sciences at Galveston, May 2006, 92 pages.
Mandel, Arkady, et al., "A renaissance in low-level laser {light) therapy—LLLT," Photonics and Lasers in Medicine, vol. 1, No. 4, Nov. 2012, pp. 231-234.
Martin, Richard, "Laser-Accelerated Inflammation/Pain Reduction and Healing," Practical Pain Management, vol. 3, No. 6, Nov./Dec. 2003, pp. 20-25.
Phurrough, Steve et al., "Decision Memo for Infrared Therapy Devices {CAG-00291 N)," Centers for Medicare & Medicaid Services, Oct. 24, 2006, 37 pages.
Poyton, Roberto et al., "Therapeutic Photobiomodulation: Nitric Oxide and a Novel Function of Mitochondrial Cytochrome C Oxidase," Discovery Medicine, Feb. 20, 2011, 11 pages.
Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 Pages.
Adamskaya, Natalia et al., "Light therapy by blue LED improves wound healing in an excision model in rats," Injury, 2010, 5 pages.
Author Unknown, "IPL Hair Removal," Spectrum Science & Beauty, Spectrum Blog, Sep. 16, 2014, 3 Pages, http://www.spectrumsciencebeauty.eom.au/ipl-hair-removal/#prettyPhoto.

* cited by examiner

PHOTOTHERAPY DEVICES FOR TREATMENT OF DERMATOLOGICAL DISORDERS OF THE SCALP

CROSS-REFERENCE TO RELATED APPLICATION

This application is a non-provisional patent application based on and claiming priority to U.S. Provisional Patent Application No. 62/197,736 filed on Jul. 28, 2015. The disclosure of the foregoing patent application is hereby incorporated herein by reference in its entirety.

TECHNICAL FIELD

This disclosure relates to devices and methods for phototherapeutic treatment of topical dermatological disorders of the scalp, such as androgenetic alopecia, acne, psoriasis, dermatitis, and other conditions.

BACKGROUND

Androgenetic alopecia is a common form of hair loss in both men and women. In men, this condition is also known as "male-pattern baldness" or pattern hair loss. This form of hair loss affects an estimated 60 million men in the United States alone. Although risk factors contributing to this condition are still being studied, researchers have determined that androgenetic alopecia is related to hormones called androgens, and particularly to an androgen called dihydrotestosterone. Increased levels of androgens in hair follicles can lead to a shorter cycle of hair growth, as well as the growth of shorter and thinner strands of hair. A majority of men regard baldness as an unwanted and distressing experience. Although baldness attributable to androgenetic alopecia is not as common in women as in men, the psychological effects of hair loss tend to be much greater for women. Although androgenic alopecia may not be the main cause of hair loss in most women, female hair loss has been reported to affect around 20 million women in the United States.

Early stages of hair loss can be slowed or reversed with medication. FDA-approved drugs include minoxidil and finasteride. Other treatment options include tretinoin combined with minoxidil, ketoconazole shampoo, and spironolactone. Advanced cases of hair loss may be resistant or unresponsive to pharmaceutical therapy. A number of patients elect to undergo surgical hair transplantation.

Various phototherapy devices for addressing androgenetic alopecia have been developed. The term "phototherapy" relates to the therapeutic use of light. Without necessarily being directed to treatment of hair loss, various light therapies (e.g., including low level light therapy (LLLT) and photodynamic therapy (PDT)) have been publicly reported or claimed to provide various health related medical benefits—including, but not limited to: treating skin or tissue inflammation; promoting tissue or skin healing or rejuvenation; enhancing wound healing; pain management; reducing wrinkles, scars, stretch marks, varicose veins, and spider veins; enhancing mood; treating microbial infections; treating hyperbilirubinemia; and treating various oncological and non-oncological diseases or disorders.

Various mechanisms by which phototherapy has been suggested to provide therapeutic benefits include: increasing circulation (e.g., by increasing formation of new capillaries); stimulating the production of collagen; stimulating the release of adenosine triphosphate (ATP); enhancing porphyrin production; reducing excitability of nervous system tissues; stimulating fibroblast activity; increasing phagocytosis; inducing thermal effects; stimulating tissue granulation and connective tissue projections; reducing inflammation; and stimulating acetylcholine release. Phototherapy has also been suggested to stimulate cells to generate nitric oxide. Various biological functions attributed to nitric oxide include roles as signaling messenger, cytotoxin, antiapoptotic agent, antioxidant, and regulator of microcirculation. Nitric oxide is recognized to relax vascular smooth muscles, dilate blood vessels, inhibit aggregation of platelets, and modulate T cell-mediate immune response. Nitric oxide is produced by multiple cell types in skin, and is formed by the conversion of the amino acid L-arginine to L-citrulline and nitric oxide, mediated by the enzymatic action of nitric oxide synthases (NOSs).

One example of a commercially available phototherapy device intended for addressing hair loss is the iGrow® laser hair rejuvenation system (Apira Science, Boca Raton, Fla., US), which embodies a rigid helmet (similar in appearance to a bicycle helmet) utilizing a combination of red laser diodes and light emitting diodes operating at 655 nm±5 nm. Another example of a commercially available phototherapy device intended for addressing hair loss is the Theradome™ LH80 Pro helmet (similar in appearance to a bicycle helmet), which utilizes 80 lasers with a peak wavelength of 678 nm (Theradome, Inc., Pleasanton, Calif., US). Yet another example of a commercially available phototherapy device intended for addressing hair loss is the Capillus® laser cap (Capillus LLC, Miami, Fla., US) embodying a rigid cap insert with 272 laser diodes operating at 650 nm arranged to fit beneath a conventional head covering such as a baseball cap, a headscarf, or a beanie. Other commercially available phototherapy devices intended for addressing hair loss include laser combs, such as the Hairmax® laser comb (Lexington Int., LLC, Boca Raton, Fla., US). Various Hairmax® laser combs utilize 7 to 12 laser modules operating at 655 nm±10 nm.

Existing phototherapy devices have limitations that affect their utility. Rigid helmet-type phototherapy devices may be uncomfortable and unsightly for many users, and such devices may be cumbersome to manufacture. Providing substantially uniform and/or uninterrupted coverage over an entire area to be treated may also be challenging for conventional phototherapy helmets, caps, and combs (e.g., as they require user movement and compliance). Thermal management may also be a concern for conventional phototherapy helmets and caps.

The art continues to seek improved phototherapy devices providing desirable illumination characteristics and capable of overcoming challenges associated with conventional phototherapy devices.

SUMMARY

Aspects of the disclosure relate to wearable devices for delivering light energy to a scalp of a patient, and methods of making and using such devices.

In a first aspect, the disclosure relates to a phototherapy device for delivering light emissions (e.g., light energy) to a scalp of a patient, the device including a flexible printed circuit board (FPCB), at least one light-transmissive layer (e.g., encapsulant or lens), and a plurality of standoffs. The FPCB includes a proximal surface supporting at least one light emitting device having an emitter height above the proximal surface, wherein the FPCB comprises a plurality of interconnected panels and a plurality of bending regions defined in and between at least some of the plurality of interconnected panels so as to allow the FPCB to provide a concave shape to cover at least a portion of a cranial vertex of the patient. The at least one light-transmissive layer is arranged proximate to the FPCB and is configured to transmit at least some light emissions generated by the at least one light emitting device. The plurality of standoffs is configured to be arranged between the FPCB and the scalp of the patient, wherein at least some standoffs of the plurality of standoffs comprise a standoff height that exceeds the emitter height.

In certain embodiments, the phototherapy device further includes driver circuitry configured to energize the at least one light emitting device to generate light emissions. In certain embodiments, the at least one light emitting device comprises a plurality of light emitting devices.

In certain embodiments, the phototherapy device further includes a shaping member having a generally concave interior arranged to receive the FPCB. In certain embodiments, the phototherapy device further includes a fabric covering arranged to cover the FPCB. In certain embodiments, the FPCB is arranged to accommodate outward expansion and inward contraction to permit the plurality of standoffs to contact the scalp of the patient. In certain embodiments, the phototherapy device further includes a fabric cap positioned proximate to a distal surface of the FPCB, wherein the fabric cap defines an aperture configured to receive an electronics housing containing at least a portion of the driver circuitry.

In certain embodiments, the phototherapy device further includes an energy storage device electrically coupled to the driver circuitry. In certain embodiments, the energy storage device comprises a battery, and the battery is retained by a battery holder coupled to the electronics housing.

In certain embodiments, the phototherapy device further includes a power supply circuit arranged to provide at least one conditioned power signal for use by at least one of a microcontroller of the phototherapy device or the at least one light emitting device, wherein upon detection of a specified number of uses of the phototherapy device, the phototherapy device is instructed to prevent further operation of the phototherapy device. In certain embodiments, the phototherapy device is configured to produce a disabling signal adapted to irreversibly disable the power supply circuit. In certain embodiments, the power supply circuit comprises at least one fusible link arranged in electrical communication with the at least one light emitting device, and the disabling signal is adapted to open the at least one fusible link to prevent current from being supplied to the at least one light emitting device.

In certain embodiments, the at least one light emitting device consists of a non-coherent light emitting device. In certain embodiments, the at least one light emitting device provides a fluence of at least 1 joule per square centimeter when energized to emit light. In certain embodiments, the at least one light emitting device comprises a first array of light emitting devices arranged to generate light having a first peak wavelength and a second array of light emitting devices arranged to generate light having a second peak wavelength, wherein the second peak wavelength differs from the first peak wavelength by at least 20 nm.

In certain embodiments, the first peak wavelength and the second peak wavelength are selected from one of the following combinations (a) to (f): (a) the first peak wavelength is in a range of from 615 nm to 635 nm and the second peak wavelength is in a range of from 650 nm to 670 nm; (b) the first peak wavelength is in a range of from 520 nm to 540 nm and the second peak wavelength is in a range of from 650 nm to 670 nm; (c) the first peak wavelength is in a range of from 410 nm to 430 nm and the second peak wavelength is in a range of from 620 nm to 640 nm; (d) the first peak wavelength is in a range of from 410 nm to 430 nm and the second peak wavelength is in a range of from 650 nm to 670 nm; (e) the first peak wavelength is in a range of from 410 nm to 430 nm and the second peak wavelength is in a range of from 495 nm to 515 nm; or (f) the first peak wavelength is in a range of from 410 nm to 430 nm and the second peak wavelength is in a range of from 520 nm to 540 nm.

In certain embodiments, the at least one light emitting device comprises a first array of light emitting devices arranged to generate light having a first peak wavelength and a second array of light emitting devices arranged to generate light having a second peak wavelength, and the second peak wavelength differs from the first peak wavelength by at least 50 nm.

In certain embodiments, the first array of light emitting devices provides a spectral output with a first peak wavelength value and a first full width at half maximum value, wherein the first peak wavelength value minus one half of the first full width at half maximum value is greater than 400 nm; and the second array of light emitting devices provides a spectral output with a second peak wavelength value and a second full width at half maximum value, wherein the second peak wavelength value minus one half of the second full width at half maximum value is greater than 450 nm.

In certain embodiments, the phototherapy device further includes a proximity sensor arranged to sense a condition indicative of placement of the phototherapy device proximate to the scalp of the patient, wherein at least one of initiation, termination, or modification of operation of the at least one light emitting device is responsive to an output signal of the proximity sensor.

In certain embodiments, the phototherapy device further includes a temperature sensor arranged to sense a temperature condition on or proximate to a portion of the phototherapy device, wherein at least one of initiation of operation, deviation of operation, or termination of operation of the at least one light emitting device is responsive to an output signal of the temperature sensor.

In certain embodiments, the phototherapy device further includes (a) a user-perceptible visible signaling element arranged to generate a visible signal, and/or (b) a user-perceptible audible signaling element arranged to generate an audible signal, wherein the visible signal and/or the audible signal is indicative of operating status of the phototherapy device, charging status of the phototherapy device, or count of operating cycles of the phototherapy device.

In certain embodiments, the plurality of standoffs is integrated with the at least one light-transmissive layer. In certain embodiments, the plurality of standoffs is attached to the at least one light-transmissive layer.

In certain embodiments, the phototherapy device is embodied in a wearable cap arranged to be worn on a head of a patient, wherein an outermost surface of the wearable cap comprises the fabric covering.

In certain embodiments, a distance from a proximal end of at least some standoffs of the plurality of standoffs to the proximal surface of the FPCB exceeds a thickness of the at least one light-transmissive layer. In certain embodiments, the plurality of standoffs is positioned between the FPCB and the at least one light-transmissive layer. In certain embodiments, the at least one light-transmissive layer comprises a flexible lenticular lens.

In certain embodiments, a method for treating at least one dermatological disorder includes placing the phototherapy device on a head of a patient, and energizing the at least one light emitting device to impinge light emissions on at least a portion of a scalp of the patient.

In another aspect, the disclosure relates to a phototherapy device for delivering light emissions to a scalp of a patient. The phototherapy device includes a flexible substrate including a proximal surface supporting at least one array of light emitting devices, and a light-transmissive layer configured to transmit at least some light emissions generated by the at least one array of light emitting devices. The device also includes a plurality of standoffs positioned between the flexible substrate and the scalp of the patient. The device further includes an energy storage element, driver circuitry arranged in electrical communication with the energy storage element and configured to drive the at least one array of light emitting devices, and a fabric covering arranged to cover the flexible substrate. The flexible substrate and the fabric covering are arranged to accommodate outward expansion and inward contraction to permit the phototherapy device to be adjustably fitted to a head of the patient.

In certain embodiments, a distance from a proximal end of at least some standoffs of the plurality of standoffs to the proximal surface of the flexible substrate exceeds a thickness of the light-transmissive layer. In certain embodiments, the plurality of standoffs is positioned between the flexible substrate and the light-transmissive layer. In certain embodiments, the light-transmissive layer comprises a flexible lenticular lens.

In certain embodiments, the flexible substrate comprises a plurality of interconnected panels and comprises a plurality of bending regions defined in and between at least some panels of the plurality of interconnected panels.

In certain embodiments, the flexible substrate comprises a flexible printed circuit board (FPCB). In certain embodiments, light emitting devices of the at least one array of light emitting devices comprises an emitter height, and the phototherapy device comprises a plurality of standoffs disposed on the FPCB and/or the light-transmissive layer and being raised relative to the proximal surface, wherein at least some standoffs of the plurality of standoffs comprise a standoff height that exceeds the emitter height.

In certain embodiments, gaps are provided between portions of adjacent panels of the plurality of interconnected panels to accommodate outward expansion and inward contraction, and to enable dissipation of heat generated by the at least one array of light emitting devices.

In certain embodiments, the phototherapy device further includes a fabric cap defining an aperture configured to receive an electronics housing containing at least a portion of the driver circuitry. In certain embodiments, the energy storage element comprises a battery, and the battery is fixed to the electronics housing or retained by a battery holder pivotally coupled to the electronics housing.

In certain embodiments, upon detection of a specified number of uses of the phototherapy device, the phototherapy device is configured to produce a disabling signal adapted to irreversibly disable the phototherapy device to prevent further operation of the phototherapy device. In certain embodiments, the disabling signal comprises a voltage spike and/or a current spike.

In certain embodiments, the phototherapy device further includes a power supply circuit arranged to provide at least one conditioned power signal for use by a microcontroller of the phototherapy device and/or the at least one array of light emitting devices, wherein the disabling signal is sent to prevent further operation of the phototherapy device.

In certain embodiments, the phototherapy device further includes at least one fusible link arranged in electrical communication with the at least one array of light emitting devices, wherein the disabling signal is adapted to open the at least one fusible link to prevent current from being supplied to the at least one array of light emitting devices.

In certain embodiments, the at least one array of light emitting devices consists of non-coherent solid state light emitting devices. In certain embodiments, the at least one array of solid state light emitting devices provides a fluence of at least 1 joule per square centimeter. In certain embodiments, the at least one array of solid state light emitting devices comprises a first array of solid state light emitting devices arranged to generate light having a first peak wavelength and a second array of solid state light emitting devices arranged to generate light having a second peak wavelength, and the second peak wavelength differs from the first peak wavelength by at least 20 nm.

In certain embodiments, the first peak wavelength and the second peak wavelength are selected from one of the following combinations (a) to (f): (a) the first peak wavelength is in a range of from 615 nm to 635 nm and the second peak wavelength is in a range of from 650 nm to 670 nm; (b) the first peak wavelength is in a range of from 520 nm to 540 nm and the second peak wavelength is in a range of from 650 nm to 670 nm; (c) the first peak wavelength is in a range of from 410 nm to 430 nm and the second peak wavelength is in a range of from 620 nm to 640 nm; (d) the first peak wavelength is in a range of from 410 nm to 430 nm and the second peak wavelength is in a range of from 650 nm to 670 nm; (e) the first peak wavelength is in a range of from 410 nm to 430 nm and the second peak wavelength is in a range of from 495 nm to 515 nm; or (f) the first peak wavelength is in a range of from 410 nm to 430 nm and the second peak wavelength is in a range of from 520 nm to 540 nm.

In certain embodiments, the at least one array of solid state light emitting devices comprises a first array of solid state light emitting devices arranged to generate light having a first peak wavelength and a second array of solid state light emitting devices arranged to generate light having a second peak wavelength, and the second peak wavelength differs from the first peak wavelength by at least 50 nm.

In certain embodiments, the first array of solid state light emitting devices provides a spectral output with a first peak wavelength value and a first full width at half maximum value, wherein the first peak wavelength value minus one half of the first full width at half maximum value is greater than 400 nm; and the second array of solid state light emitting devices provides a spectral output with a second peak wavelength value and a second full width at half maximum value, wherein the second peak wavelength value minus one half of the second full width at half maximum value is greater than 450 nm.

In certain embodiments, the phototherapy device further includes an optical sensor arranged to sense a condition indicative of placement of the phototherapy device proximate to the scalp of the patient, wherein initiation, termination, and/or modification of operation of the at least one array of light emitting devices is responsive to an output signal of the optical sensor.

In certain embodiments, the phototherapy device further includes a temperature sensor arranged to sense a temperature condition on or proximate to a portion of the phototherapy device, wherein initiation of operation, modification of operation, and/or termination of operation of the at least one array of light emitting devices is responsive to an output signal of the temperature sensor.

In certain embodiments, the phototherapy device further includes (a) a user-perceptible visible signaling element arranged to generate a visible signal and/or (b) a user-perceptible audible signaling element arranged to generate an audible signal, wherein the visible signal and/or the audible signal is indicative of operating status of the phototherapy device, charging status of the phototherapy device, or count of operating cycles of the phototherapy device.

In certain embodiments, the phototherapy device further includes (a) a user-perceptible visible signaling element arranged to generate a visible signal and/or (b) a user-perceptible audible signaling element arranged to generate an audible signal, wherein the visible signal and/or the audible signal is indicative of count of operating cycles of the phototherapy device.

In certain embodiments, the phototherapy device is embodied in a wearable cap arranged to be worn on the head of the patient, wherein an outermost surface of the wearable cap comprises the fabric covering.

In certain embodiments, a method for treating at least one dermatological disorder includes placing the phototherapy device on the head of the patient, and energizing the at least one array of light emitting devices to impinge light energy on at least a portion of a scalp of the patient.

In another aspect, the disclosure relates to a method for treating at least one dermatological disorder, the method comprising placing a phototherapy device as disclosed herein on the head of a patient, and energizing the at least one array of light emitting devices to impinge light energy on at least a portion of a scalp of the patient.

In another aspect, the disclosure relates to a phototherapy device for delivering light emissions to a scalp of a patient. The device comprises a flexible lens comprising a proximal lens surface and a distal lens surface, a flexible printed circuit board (FPCB) including at least one light emitting device on a proximal surface thereof, and a plurality of standoffs positioned between the distal lens surface and the FPCB to maintain a minimum distance between the at least one light emitting device and the distal lens surface. The phototherapy device is configured to transmit light emissions generated by the at least one light emitting device through the flexible lens to the scalp of the patient.

In certain embodiments, a distance from a proximal end of each standoff of the plurality of standoffs to the proximal surface of the flexible lens exceeds a thickness of the flexible lens. In certain embodiments, the light-transmissive layer comprises a flexible lenticular lens.

In certain embodiments, the phototherapy device further includes a communication module configured to electronically communicate with an electronic device external to the phototherapy device.

In certain embodiments, light emissions of the at least one light emitting device are within a range of about from 410 nm to 455 nm. In certain embodiments, light emissions of the at least one light emitting device are within a range of about from 620 nm to 700 nm, or from 620 nm to 900 nm. In certain embodiments, the light emissions are configured to treat or prevent hair loss of the patient.

In certain embodiments, a method for treating at least one dermatological disorder includes placing the phototherapy device on a head of the patient, and energizing the at least one light emitting device to deliver light emissions to at least a portion of the scalp of the patient.

In certain embodiments, the phototherapy device further includes driver circuitry configured to energize the at least one light emitting device to generate light emissions. In certain embodiments, the at least one light emitting device comprises a plurality of light emitting devices.

In certain embodiments, the phototherapy device further includes a fabric cap, wherein the FPCB is positioned between the fabric cap and the flexible lens, and the FPCB comprises expansion joints to permit adjustment of an opening circumference of the fabric cap. In certain embodiments, the fabric cap defines an aperture configured to receive an electronics housing containing at least a portion of the driver circuitry. In certain embodiments, the FPCB is arranged to accommodate outward expansion and inward contraction.

In certain embodiments, the phototherapy device further includes an energy storage device electrically coupled to the driver circuitry, wherein the energy storage device comprises a battery, and the battery is retained by a battery holder coupled to the electronics housing.

In certain embodiments, the phototherapy device further includes a power supply circuit arranged to provide at least one conditioned power signal for use by at least one of a microcontroller of the phototherapy device or the at least one light emitting device, wherein the disabling signal is adapted to irreversibly disable the power supply circuit.

In certain embodiments, the plurality of standoffs is integrated with the flexible lens. In certain embodiments, the plurality of standoffs is attached to the flexible lens.

In certain embodiments, the phototherapy device includes a substrate comprising a plurality of interconnected panels and a plurality of bending regions defined in and between multiple panels of the plurality of interconnected panels.

In certain embodiments, upon detection of a specified number of uses of the phototherapy device, the phototherapy device is configured to produce a disabling signal adapted to irreversibly disable the phototherapy device to prevent further operation of the phototherapy device. In certain embodiments, the disabling signal comprises a voltage spike and/or a current spike.

In certain embodiments, the phototherapy device further includes at least one fusible link arranged in electrical communication with the at least one light emitting device (e.g. at least one array of light emitting devices), wherein the disabling signal is adapted to open the at least one fusible link to prevent current from being supplied to the at least one light emitting device.

In certain embodiments, the phototherapy device further includes an optical sensor arranged to sense a condition indicative of placement of the phototherapy device proximate to the scalp of the patient, wherein at least one of initiation, termination, or modification of operation of the at least one light emitting device (e.g. at least one array of light emitting devices) is responsive to an output signal of the optical sensor.

In certain embodiments, the phototherapy device further includes a temperature sensor arranged to sense a temperature condition on or proximate to a portion of the phototherapy device, wherein at least one of initiation of operation, modification of operation, or termination of operation of the at least one light emitting device (e.g. at least one array of light emitting devices) is responsive to an output signal of the temperature sensor.

In certain embodiments, the flexible lens comprises a flexible lenticular lens. In certain embodiments, the plurality of standoffs is integrally attached to the flexible lenticular lens. In certain embodiments, the flexible lens and the FPCB are adjustable in size and/or shape to accommodate various head sizes. In certain embodiments, the flexible lenticular lens and the plurality of standoffs are formed by molding.

In another aspect, the disclosure relates to a phototherapy device for delivering light energy to a scalp of a patient. The phototherapy device comprises a fabric cap, a flexible lenticular lens including a plurality of standoffs extending from a distal surface thereof, and a flexible printed circuit board (FPCB) positioned between the flexible lenticular lens and the fabric cap, the FPCB including a plurality of interconnected panels defining a concavity, and at least one light emitting device arranged on a proximal surface of the FPCB and configured to generate non-coherent light. The plurality of standoffs is configured to maintain separation of a minimum distance between the at least one light emitting device and the distal surface of the flexible lenticular lens. The phototherapy device is configured to be worn on a head of the patient to cover at least a portion of a cranial vertex of the patient to transmit at least a portion of the non-coherent light generated by the at least one light emitting device to impinge on the scalp of the patient. In another aspect, the disclosure relates to a method of delivering light energy to a scalp of a patient. The method comprises positioning a phototherapy device over a head of the patient, the phototherapy device including a flexible lens including a distal lens surface, a flexible printed circuit board (FPCB) at least partially covering the flexible lens and supporting at least one light emitting device, and a plurality of standoffs positioned between the distal lens surface and the FPCB to maintain a minimum distance between the at least one light emitting device and the distal lens surface; adjusting the size and/or shape of the phototherapy device to fit the head of the patient; generating light emissions from the at least one light emitting device mounted to the FPCB; and transmitting at least a portion of the generated light emissions through at least one light-transmissive portion of the flexible lens to impinge on the scalp of the patient.

In another aspect, the disclosure relates to a method of assembling a phototherapy device. The method comprises arranging a flexible printed circuit board (FPCB) over at least a portion of a flexible lens, the FPCB including at least one light emitting device mounted thereto, wherein a plurality of standoffs is positioned between a distal lens surface and the FPCB to maintain a minimum distance between the at least one light emitting device and the distal lens surface, and arranging a fabric cap over at least a portion of the FPCB, with the FPCB secured between the fabric cap and the flexible lens.

In another aspect, the disclosure relates to a capacitor. The capacitor comprises a first flexible circuit board element comprising a first conductive material layer and a first dielectric material layer, a second flexible circuit board element comprising a second conductive material layer and a second dielectric material layer, and at least one solid spacer joined between the first flexible circuit board element and the second flexible circuit board element.

In certain embodiments, the at least one solid spacer has a dielectric constant value in a range of from about 2 to about 5. In certain embodiments, the at least one solid spacer is adhered between the first flexible circuit board element and the second flexible circuit board element.

In certain embodiments, the first flexible circuit board element comprises a continuous extension of the second flexible circuit board element, with a recurved flexure region arranged between the first flexible circuit board element and the second flexible circuit board element. In certain embodiments, the first conductive material layer has a larger lateral extent than the second conductive material layer.

In certain embodiments, the at least one solid spacer, the first dielectric material layer, and the second dielectric material layer maintain a distance between the first conductive material layer and the second conductive material layer in a range of from about 0.2 mm to about 2 mm. In certain embodiments, the distance is in a range of from about 0.3 mm to about 1.9 mm.

In certain embodiments, a proximity sensor comprises the capacitor.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Other aspects, features and embodiments of the invention will be more fully apparent from the ensuing disclosure and the appended claims.

DETAILED DESCRIPTION

Figure 1:
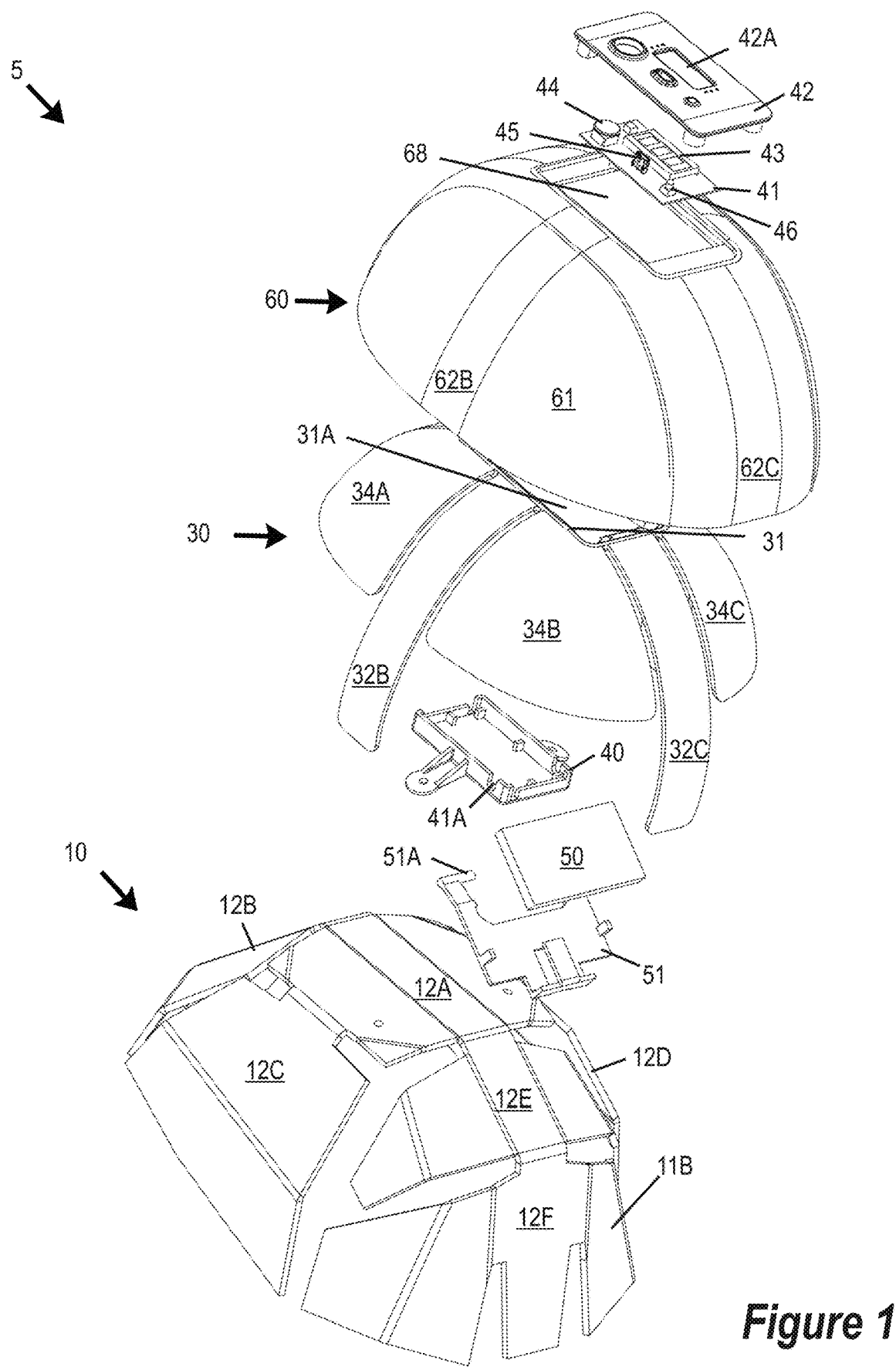
FIG. 1 is an exploded view of a light emitting device embodied in a wearable cap for delivering light emissions to a scalp of a patient, the device including multiple light emitters and standoffs supported by a FPCB arranged in a concave configuration, a concave shaping member configured to receive the FPCB and configured to support a battery and control module, and a fabric covering arranged to cover the support member and flexible substrate.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

Aspects of the disclosure relate to wearable devices for delivering light energy to a scalp of a patient, and methods of making and using such devices.

Various embodiments disclosed herein include a flexible printed circuit board (FPCB) supporting at least one light emitting device. In certain embodiments, a FPCB may include a polyimide-containing layer and at least one layer of copper or another electrically conductive material. In certain embodiments, a light-transmissive layer (e.g., an encapsulant or lens) may be arranged to cover and/or arranged in contact with at least a portion of a FPCB and any light emitter(s) supported thereon. A preferred encapsulant material is silicone, which may be applied by any suitable means such as molding, dipping, spraying, dispensing, printing, or the like. In certain embodiments, substantially all surfaces (e.g., front and back surfaces) of a FPCB may be covered with encapsulant material. In certain embodiments, the total thickness of an encapsulated flexible LED including embedded light emitters may be in a range of 1 mm to 5 mm, or in a range of from 1 mm to 3 mm, not including standoffs. In certain embodiments, the FPCB comprises a flexible polymer film, polyester (PET), polyimide (PI), polyethylene naphthalate (PEN), polyetherimide (PEI), fluropolymers (FEP), copolymers, etc.

In certain embodiments, at least one standoff is configured to be arranged between the FPCB and the scalp of the patient, with the at least one standoff including a standoff height that exceeds a height of emitters supported by the FPCB. Preferably, the at least one standoff comprises a light-transmissive material such as silicone, PET, PET-G, etc.

In certain embodiments, steps of forming an encapsulated FPCB with standoffs may include defining electrical traces on the FPCB; mounting, forming or otherwise affixing one or more light emitting elements on the FPCB, forming standoffs or standoff portions; and encapsulating various structures including the light emitting elements, the FPCB, and optionally encapsulating standoffs or standoff portions. In certain embodiments, the order of the preceding steps may be altered, and in certain embodiments, portions or the entirety of at least some standoffs may be devoid of encapsulant.

In certain embodiments, standoffs or standoff portions may be molded, placed, formed, printed, adhered, or otherwise applied to a face of a FPCB prior to encapsulation, and the standoffs or standoff portions may thereafter be partially or fully encapsulated together with one or more light emitting elements and one or more portions of the FPCB.

In certain embodiments, standoffs or standoff portions may be placed, formed, printed, adhered, or otherwise applied to a face of a FPCB after the FPCB and light emitting elements have been encapsulated.

In certain embodiments, standoffs or standoff portions may be formed concurrently with an encapsulation process, such as by molding, printing, spraying, or other deposition methods.

In certain embodiments, crosslinkable materials may be selectively applied or formed along regions of a FPCB, and such materials may be activated by appropriate means (e.g., heat, photonic energy, chemical activation, or the like) to form standoffs or standoff portions, whether before, during, or after an encapsulation step.

In certain embodiments, standoff height, standoff shape, light emitting element spacing, and light element optical distribution may be selected to permit adjacent light emitting elements to provide an overlapping beam pattern on a scalp of a patient.

In certain embodiments, an array of multiple standoffs may be formed on, in, or over an encapsulant material. In certain embodiments, each standoff within an array has substantially the same size, shape, and/or durometer. In other embodiments, different standoffs within an array may include different sizes, shapes, and/or durometers.

In certain embodiments, one or more standoffs may include suitable shapes and/or materials to provide light focusing utility, light diffusing utility, and/or light scattering utility. In certain embodiments, one or more standoffs may include one or more wavelength conversion materials (e.g., phosphors, quantum dots, fluorophores, or the like) and provide wavelength conversion utility. In certain embodiments, one or more standoffs may include suitable shapes and/or materials to provide light reflection utility.

In certain embodiments, one or more standoffs may be placed apart from one or more light emitting elements. In other embodiments, one or more standoffs may be intentionally placed on or over one or more light emitting elements, with the standoff(s) serving to transmit, shape, and/or otherwise affect light received from one or more light emitting elements.

Various types of light emitting elements may be used with a phototherapy device for delivering light energy to a scalp of a patient. In certain embodiments, emissions of a phototherapy device may consist of non-coherent light (e.g., characteristic of light emitting diode emissions). In certain embodiments, emissions of a phototherapy device may consist of coherent light (e.g., characteristic of laser emissions). In certain embodiments, emissions of a phototherapy device may include a combination of coherent light and non-coherent light. In certain embodiments, a phototherapy device is devoid of any laser diodes arranged to impinge light on a patient's scalp.

In certain embodiments, a phototherapy device for delivering light energy to a scalp of a patient may include one or more solid state light emitting devices. Examples of solid state light emitting devices include (but are not limited to) light emitting diodes, lasers, thin film electroluminescent devices, powdered electroluminescent devices, field induced polymer electroluminescent devices, and polymer light-emitting electrochemical cells.

In certain embodiments, multiple emitters of different peak wavelengths (e.g., having peak wavelengths differing by at least about 10 nm, at least about 20 nm, at least about 30 nm, at least about 50 nm, at least about 75 nm, at least about 100 nm, or another threshold specified herein) may be provided.

In certain embodiments, light of different peak wavelengths may be generated by different emitters contained in a single (e.g., solid state) emitter package, wherein close spacing between adjacent emitters may provide integral color mixing. In certain embodiments, one or more arrays of light emitting devices may be provided. In certain embodiments, a first array of light emitting devices may be configured to provide light of a first peak wavelength, and a second array of light emitting devices may be configured to provide light of second peak wavelength. In certain embodiments, an array of multi-emitter packages may be provided, wherein emitters within a single package may provide the same or different peak wavelengths. In certain embodiments, an array of solid state emitter packages may embody packages further including second, third, fourth, and/or fifth solid state emitters, such that a single array of solid state emitter packages may embody two, three, four, or five arrays of solid state emitters, wherein each array is arranged to generate emissions with a different peak wavelength.

In certain embodiments, a phototherapy device for delivering light energy to a scalp of a patient may include one or more light emitting devices devoid of a wavelength conversion material. In other embodiments, one or more light emitting devices may be arranged to stimulate a wavelength conversion material, such as a phosphor material, a fluorescent dye material, a quantum dot material, and a fluorophore material.

In certain embodiments, one or more light emitting devices may be arranged to provide substantially monochromatic light. In certain embodiments, one or more light emitting devices may include a spectral output having a full width at half maximum value of less than 25 nm (or less than 20 nm, or less than 15 nm, or in a range of from 5 nm to 25 nm, or in a range of from 10 nm to 25 nm, or in a range of from 15 nm to 25 nm).

In certain embodiments, one or more light emitting devices may be arranged to provide emissions having a peak wavelength in a range of from 400 nm to 900 nm, or in a range of from 500 nm to 900 nm, or in a range of from 500 nm to 800 nm, or in a range of from 600 nm to 700 nm, or in a range of from 620 nm to 670 nm.

In certain embodiments, at least one light emitting device may be arranged to provide emissions having a peak wavelength in a range of from 620 nm to 645 nm (or from 615 nm to 635 nm), and at least one emitting device may be arranged to provide emissions having a peak wavelength in a range of from 645 nm to 670 nm (or from 650 nm to 670 nm). In certain embodiments, at least one first light emitting device may be arranged to provide emissions having a peak wavelength of about 630 nm, and at least one second light emitting device may be arranged to provide emissions having a peak wavelength of about 660 nm. Such wavelengths may be useful to provide anti-inflammatory effects and/or to promote vasodilation. Anti-inflammatory effects may be useful to promote wound healing, to reduce acne blemishes, to promote facial aesthetics, and/or to treat atopic dermatitis and other topical dermatological disorders. Vasodilation may also be beneficial to treat androgenic alopecia or other topical dermatological disorders.

In certain embodiments, at least one light emitting device (or multiple light emitting devices) may be configured to produce light in a wavelength range and flux that may alter the presence, concentration, or growth of bacteria or other microbes in or on living mammalian tissue receiving the light. UV light and near-UV light (e.g., having peak wavelengths from 400 nm to 435 nm, or more preferably from 410 nm to 430 nm) in particular may affect microbial growth. Effects on microbial growth may depend on the wavelength range and dose. In certain embodiments, emitted light may include near-UV light having a peak wavelength in a range of from 410 nm to 430 nm to provide a bacteriostatic effect (e.g., with pulsed light having a radiant flux of <9 mW/cm$^2$), provide a bactericidal effect (e.g., with substantially steady state light having a radiant flux in a range of from 9 mW/cm$^2$ to 17 mW/cm$^2$), or provide an antimicrobial effect (e.g., with substantially steady state light having a radiant flux in a range of greater than 17 mW/cm$^2$, such as in a range of from 18 mW/cm$^2$ to 60 mW/cm$^2$). In certain embodiments, emitted light in a near-UV range (e.g., from 400 nm to 420 nm, or from 410 nm to 420 nm) may also affect microbial growth (whether in a bacteriostatic range, bactericidal range, or an antimicrobial range) for uses such as wound healing, reduction of acne blemishes, or treatment of atopic dermatitis.

In certain embodiments, at least one light emitting device (or multiple light emitting devices) may be configured to produce light in a wavelength range and flux that may trigger the release of nitric oxide from endogenous stores (e.g., at least one of nitrosoglutathione, nitrosoalbumin, nitrosohemoglobin, nitrosothiols, nitrosamines, and metal nitrosyl complexes). In certain embodiments, light having a peak wavelength in a range of from 400 nm to 435 nm, or from 410 nm to 430 nm, or from 430 nm to 490 nm, or from 510 nm to 550 nm, or from 520 nm to 540 nm, may be used for this purpose.

In certain embodiments, light having peak wavelengths of any one, two, three, or more of the following values may be used: about 415 nm, about 505 nm, about 530 nm, about 630 nm, and/or 660 nm.

In certain embodiments, any suitable combination of peak wavelengths disclosed herein may be used in combination for desired therapeutic effects (e.g., vasodilation, inflammation reduction, enzymatic, nitric oxide generation, nitric oxide release, and antimicrobial functions). In certain embodiments, a combination of wavelengths may be provided during the same time window, during overlapping but non-coincident time windows, or during non-overlapping time windows.

In certain embodiments, at least one first light emitter and at least one second light emitter (which may be embodied in a first array of light emitters and a second array of light emitters) may be arranged to provide different peak wavelengths selected from one of the following combinations (a) to (f): (a) the first peak wavelength is in a range of from 620 nm to 640 nm (or from 615 nm to 635 nm) and the second peak wavelength is in a range of from 650 nm to 670 nm; (b) the first peak wavelength is in a range of from 520 nm to 540 nm and the second peak wavelength is in a range of from 650 nm to 670 nm; (c) the first peak wavelength is in a range of from 400 nm to 420 nm (or from 410 nm to 430 nm) and the second peak wavelength is in a range of from 620 nm to 640 nm; (d) the first peak wavelength is in a range of from 400 nm to 420 nm (or from 410 nm to 430 nm) and the second peak wavelength is in a range of from 650 nm to 670 nm; (e) the first peak wavelength is in a range of from 400 nm to 420 nm (or from 410 nm to 430 nm) and the second peak wavelength is in a range of from 495 nm to 515 nm; and (f) the first peak wavelength is in a range of from 400 nm to 420 nm (or from 410 nm to 430 nm) and the second peak wavelength is in a range of from 520 nm to 540 nm.

In certain embodiments, a first array of light emitting devices provides a spectral output with a first peak wavelength value and a first full width at half maximum value, wherein the first peak wavelength value minus one half of the first full width at half maximum value is greater than 400 nm. Additionally, a second array of light emitting devices provides a spectral output with a second peak wavelength value and a second full width at half maximum value, wherein the second peak wavelength value minus one half of the second full width at half maximum value is greater than 450 nm.

In certain embodiments, one or more light emitting devices may provide a fluence of at least 1 joule per square centimeter, at least 3 joules per square centimeter, or at least 5 joules per square centimeter when energized to emit light. In certain embodiments, one or more light emitting devices may provide a radiant flux in a range of from 5 mW/cm$^2$ to 60 mW/cm$^2$.

In certain embodiments, one or more light emitting devices may be arranged to provide substantially steady state light. In certain embodiments, one or more light emitting devices may be arranged to provide multiple discrete pulses of light.

In certain embodiments, a device for delivering light energy to a scalp of a patient may include a FPCB with multiple interconnected panels and a plurality of bending regions defined in and between the multiple panels to allow the FPCB to provide a concave shape to cover at least a portion of a cranial vertex of a patient. In certain embodiments, openings are provided between portions of adjacent panels to permit transport of heat and fluids (e.g., perspiration). In certain embodiments, a fabric covering may be arranged to cover the FPCB, with the fabric covering preferably being breathable to permit transport of heat and fluid transport (e.g., evaporation of sweat). In certain embodiments, the fabric covering may include an adjustable closure arranged to permit an opening circumference of the fabric covering to be adjusted. If the FPCB is contained within the fabric covering, then adjustment of the closure may selectively compress a portion of the FPCB and therefore also permit an opening circumference of the FPCB to be adjusted. In certain embodiments, the FPCB and the fabric covering are arranged to accommodate outward expansion and inward contraction to permit standoffs of the FPCB to contact the scalp of the patient.

In certain embodiments, a flexible shaping member having a generally concave interior may be arranged to receive a FPCB. In certain embodiments, a flexible shaping member may be provided between a FPCB and a fabric covering. In certain embodiments, the FPCB and the shaping member may be arranged to accommodate outward expansion and inward contraction to permit the plurality of standoffs to contact the scalp of the patient.

In certain embodiments, a flexible shaping member includes a central frame and a plurality of ribs attached to the frame. The plurality of ribs may include at least one front rib, at least one rear rib, and at least two lateral ribs, wherein each rib of the plurality of ribs projects generally outwardly from the central frame to define an outer portion of the generally concave interior. In certain embodiments, a fabric covering may include multiple pockets arranged to receive the plurality of ribs to retain the fabric covering in a position fully covering the flexible shaping member and the FPCB. In certain embodiments, the fabric covering comprises an outermost surface of a wearable cap arranged to be worn on the head of a patient.

In certain embodiments, a flexible shaping member may include, in addition to a plurality of ribs, a plurality of curved panels projecting generally outwardly and downwardly from the central frame to substantially conform to a portion of the cranial vertex, wherein each curved panel of the plurality of curved panels is arranged between two different ribs of the plurality of ribs. In certain embodiments, gaps may be provided between portions of adjacent ribs and curved panels to accommodate outward expansion and inward contraction, and to enable dissipation of heat generated by the at least one light emitting device associated with the FPCB retained within the flexible shaping member. In certain embodiments, a flexible shaping member may be fabricated from a suitable polymeric material.

In certain embodiments, a central frame of a flexible shaping member includes an aperture or opening configured to receive an electronics housing. In certain embodiments, the electronics housing may include driver circuitry (or at least a portion of driver circuitry) configured to energize at least one light emitting device for impingement of light on the scalp of a patient. In certain embodiments, the electronics housing may include one or more user interface, sensory interface, charging interface, data interface, signal input, signal output, and/or display elements. In certain embodiments, an energy storage device (e.g., a battery) may be retained by a battery holder pivotally (or otherwise movably) coupled to the electronics housing. Such movable coupling may permit relative movement between the battery holder and electronics housing to permit the phototherapy device to accommodate a variety of patients having different head sizes and shapes.

In certain embodiments, operation of a device as disclosed herein may be responsive to one or more signals generated by one or more sensors or other elements. Various types of sensors are contemplated, including temperature sensors, photosensors, image sensors, proximity sensors, pressure sensors, chemical sensors, biosensors, accelerometers, moisture sensors, oximeters, current sensors, voltage sensors, and the like. Other elements that may affect impingement of light and/or operation of a device as disclosed herein include a timer, a cycle counter, a manually operated control element, a wireless transmitter and/or receiver (as may be embodied in a transceiver), a laptop or tablet computer, a mobile phone, or another portable digital device. Wired and/or wireless communication between a device as disclosed herein and one or more signal generating or signal receiving elements may be provided.

In certain embodiments, a light emitting device as disclosed herein may be configured to prevent unauthorized usage beyond an authorized number of treatment cycles. In certain embodiments, a number of treatment cycles of the device may be incremented and stored in a counter or other memory element. In certain embodiments, when the number of treatment cycles reaches a predetermined limit, operation of a device may be reversibly or irreversibly disabled. In certain embodiments, when the number of treatment cycles reaches a predetermined limit, a signal may be communicated to a user to notify the user that a predetermined limit of a number of treatment cycles has been reached, and a user may be prompted to either (i) purchase a new device or component thereof, or (ii) purchase the ability to continue using the device for a specified number of additional cycles or for a specified additional time period. In certain embodiments, one or more signals relating to cycle usage and/or enabling a user to purchase additional usage may be communicated via wired or wireless means. In certain embodiments, a user may download an application for use on a personal computer, a tablet computer, a mobile phone, or another portable digital device, and the application may provide cycle usage information and/or permit the user to purchase additional cycles or purchase additional usage time to continue using the device.

In certain embodiments, upon detection of a specified number of uses of the device, a light emitting device may be configured to produce a disabling signal adapted to irreversibly disable the device to prevent further operation of the device. In certain embodiments, the disabling signal may include at least one of a voltage spike and a current spike arranged to damage at least one circuit element. In certain embodiments, a light emitting device includes a power supply circuit arranged to provide at least one conditioned power signal for use by a microcontroller of the device and/or the at least one light emitting device, and a disabling signal may be adapted to irreversibly disable at least one element of the power supply circuit. In certain embodiments, at least one fusible link may be arranged in electrical communication with the at least one light emitting device, and a disabling signal may be adapted to open the at least one fusible link to prevent current from being supplied to the at least one light emitting device. In certain embodiments, at least one fusible link may be arranged in electrical communication with at least one light emitter and/or a light emitter driver circuit.

In certain embodiments, impingement of light on living tissue and/or operation of a device as disclosed herein may be responsive to one or more temperature signals. For example, a temperature condition may be sensed on or proximate to a FPCB; at least one signal indicative of the temperature condition may be generated; and operation of a device for delivering light energy to a scalp of a patient may be controlled responsive to the at least one signal. Such control may include initiation of operation, deviation (or alteration) of operation, or termination of operation of light emitting elements. In certain embodiments, thermal foldback protection may be provided at a threshold temperature (e.g., >42° Celsius) to prevent a user from experiencing burns or discomfort. In certain embodiments, thermal foldback protection may trigger a light emitting device to terminate operation, reduce current, or change an operating state in response to receipt of a signal indicating an excess temperature condition.

In certain embodiments, a proximity sensor may be arranged proximate to a portion of a FPCB to determine when a FPCB is proximate to a surface (e.g., scalp) to be illuminated and used for safety of a patient by reducing flux when not proximate to the surface.

In certain embodiments, a device for delivering light energy to a scalp of a patient may include a user-perceptible visible signaling element (e.g., one or more lights, a LED display, an alphanumeric display, mobile app, or the like) arranged to generate a visible signal and/or a user-perceptible audible signaling element (e.g., a speaker, a buzzer, an alarm generator, or the like) arranged to generate an audible signal. In certain embodiments, at least one of the visible signal and the audible signal is indicative of operating status or charging status of the device. In certain embodiments, at least one of the visible signal and the audible signal is indicative of count of operating cycles of the device.

In certain embodiments, a device for delivering light energy to a scalp of a patient as disclosed herein may include a memory element to store information indicative of one or more sensor signals. Such information may be used for detecting device usage, assessing patient status, assessing patient improvement, and assessing function of the device. In certain embodiments, information indicative of one or more sensor signals may be transmitted via wired or wireless means (e.g., via Bluetooth, WiFi, Zigbee, or another suitable protocol) to a mobile phone, a computer, a data logging device, or another suitable device that may optionally be connected to a local network, a wide-area network, a telephonic network, or other communication network. In certain embodiments, a data port (e.g., micro USB or other type) may be provided to permit extraction or interrogation of information contained in a memory.

Details of illustrative devices for delivering light energy to a scalp of a patient are described hereinafter.

FIG. 1 is an exploded view of a light emitting device 5 embodied in a wearable cap for delivering light energy to a scalp of a patient. The device 5 includes multiple light emitters and standoffs supported by a FPCB 10 including multiple interconnected panels 12A-12F (e.g., multiple interconnected elements) arranged in a concave configuration. A concave shaping member 30 (including a frame 31, ribs 32A-32D, and curved panels 34A-34D) is configured to receive the FPCB 10. A fabric covering 60 is configured to cover the concave shaping member 30 and the FPCB 10 contained therein. A battery 50 and a battery holder 51 are arranged between the FPCB 10 and the concave shaping member 30. An electronics housing 40 is arranged to be received within an opening 31A defined in the frame 31 of the concave shaping member 30. Pivotal coupling elements 41A, 51A (e.g., cylindrical tabs) are arranged to pivotally couple the battery holder 51 to the electronics housing 40. An electronics board 41 is insertable into the electronics housing 40, which is enclosed with a cover 42. Arranged on the electronics board 41 are a cycle counter 43, a control button 44, a charging/data port 45, and a status lamp 46. The various elements associated with the electronics housing 40 and the electronics board 41 may be referred to generally as a "control module." Windows 42A defined in the cover 42 provide access to the cycle counter 43, the control button 44, the charging/data port 45, and the status lamp 46. The fabric covering 60 includes a fabric body 61 and multiple internal pockets 62A-62D arranged to receive portions of the ribs 32A-32D. An opening 68 at the top of the fabric covering 60 is arranged to receive the cover 42.

Figure 2A:
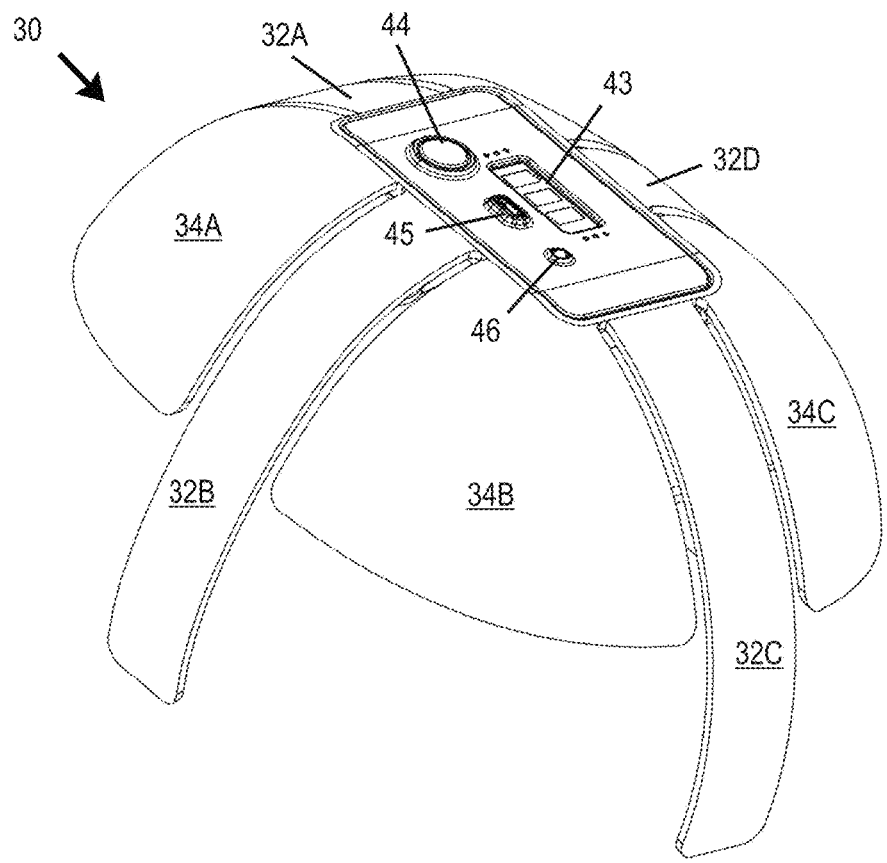
FIG. 2A is an upper perspective view of the concave shaping member together in combination with the control module (with battery) of FIG. 1.
Figure 2B:
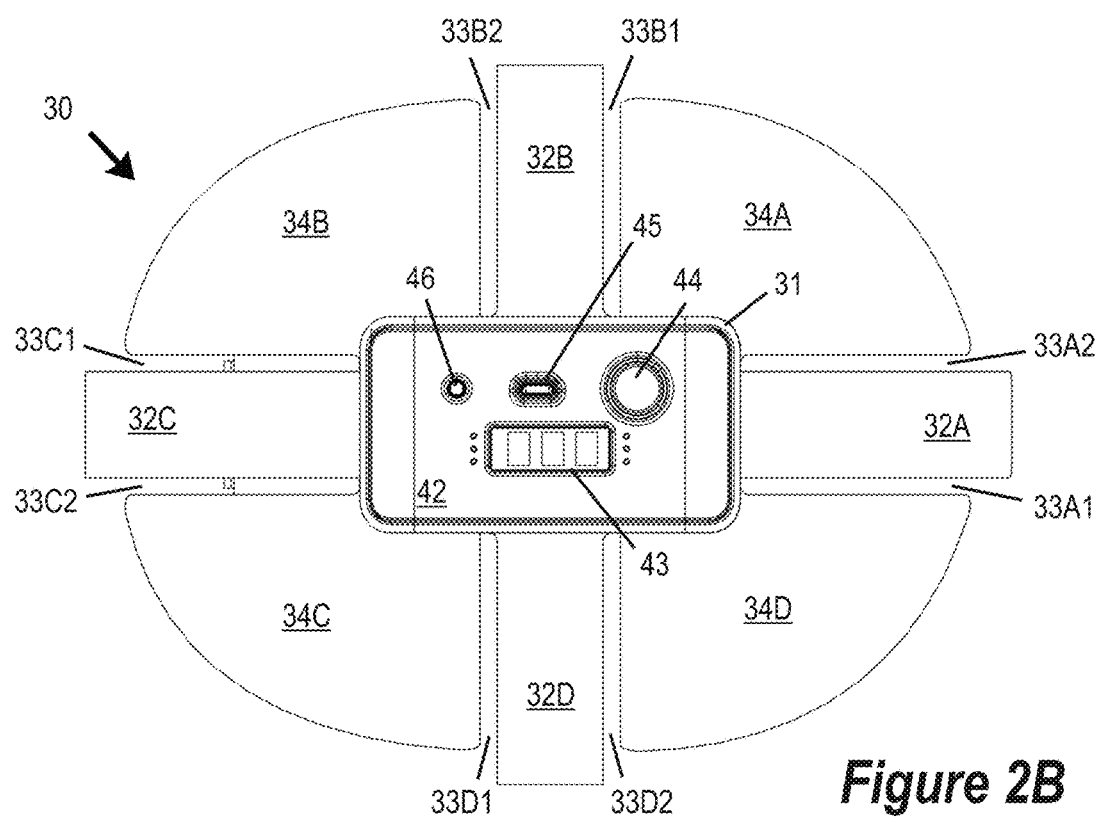
FIG. 2B is a top plan view of the concave shaping member and control module of FIG. 2A.
Figure 2C:
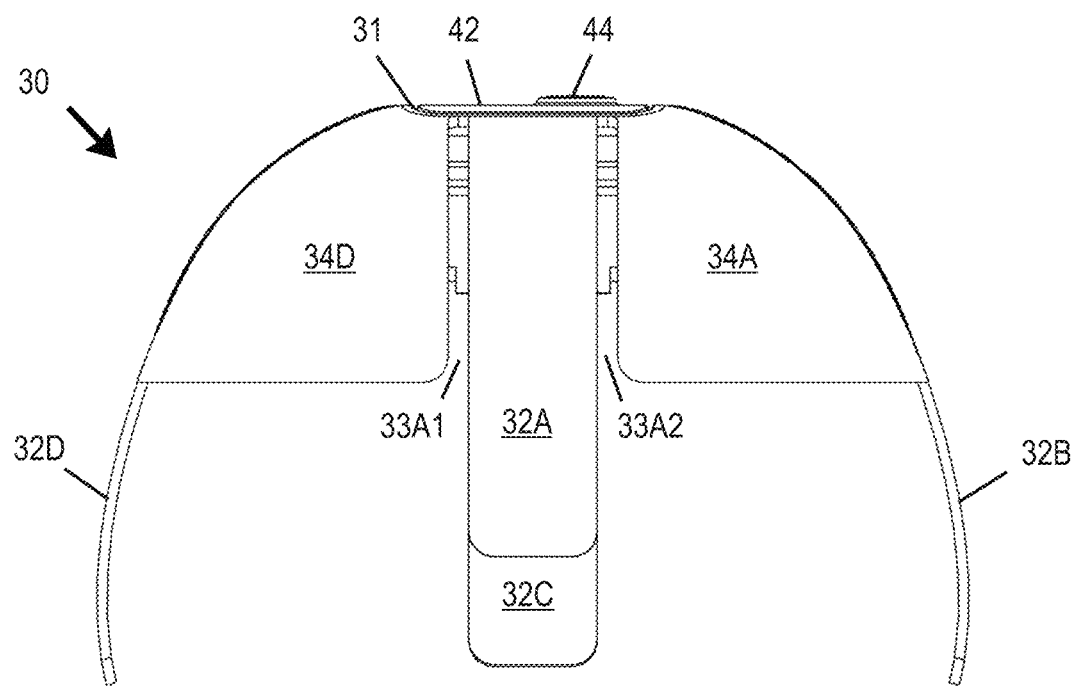
FIG. 2C is a front elevation view of the concave shaping member and control module of FIGS. 2A and 2B.
Figure 2D:
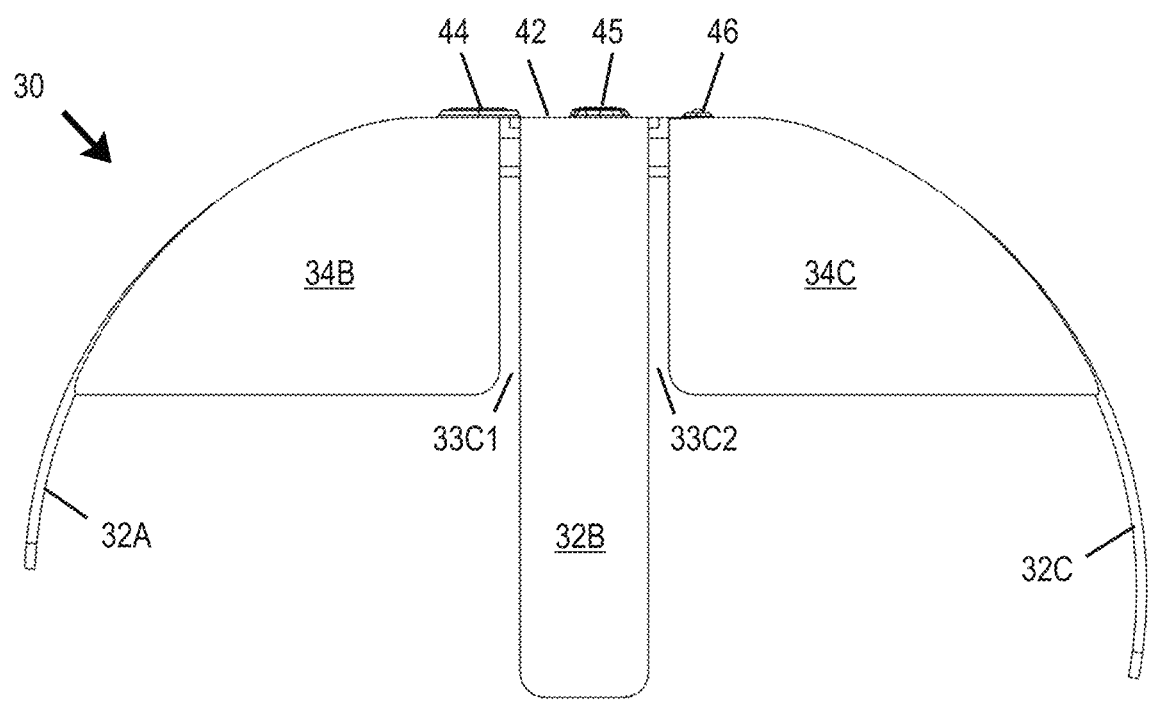
FIG. 2D is a left side elevation view of the concave shaping member and control module of FIGS. 2A-2C.
Figure 2E:
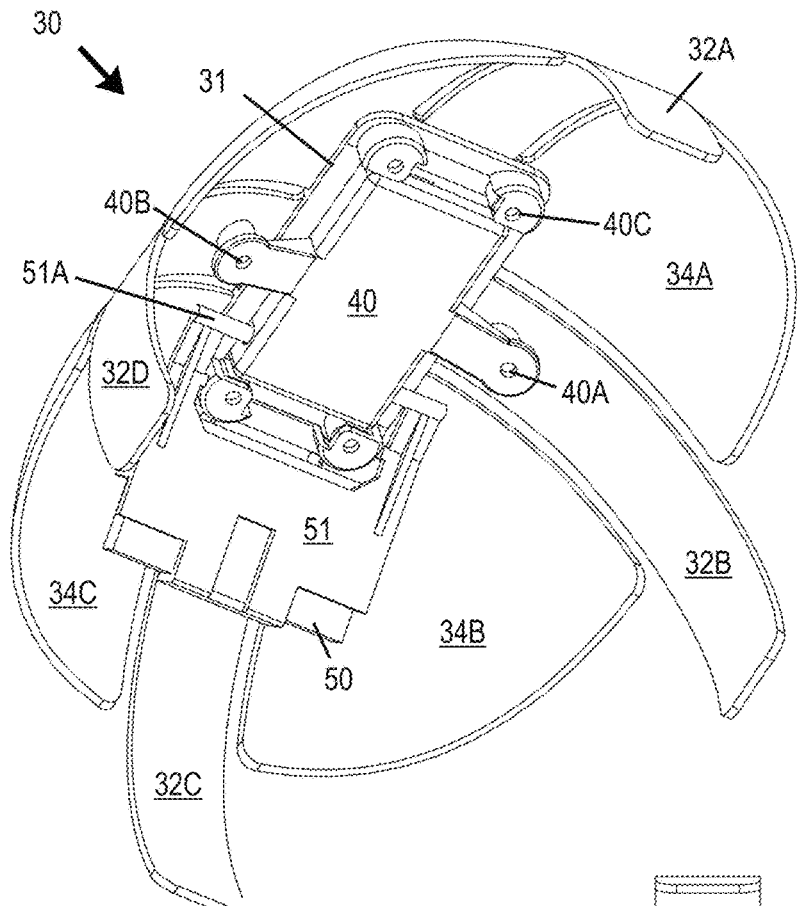
FIG. 2E is a lower perspective view of the concave shaping member and control module of FIGS. 2A-2D.
Figure 2F:
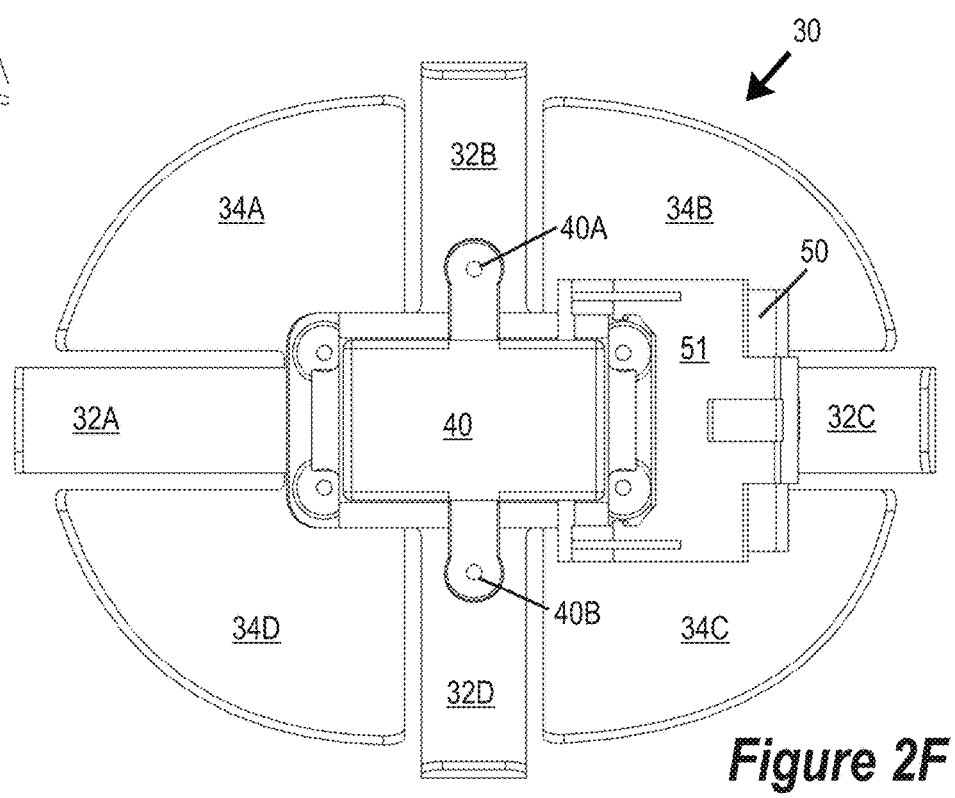
FIG. 2F is a bottom plan view of the concave shaping member and control module (with battery) of FIGS. 2A-2E.

Further views of the concave shaping member 30, the electronics housing 40, and the battery holder 51 are provided in FIGS. 2A-2F. FIG. 2A is an upper perspective view, FIG. 2B is a top plan view, FIG. 2C is a front elevation view, FIG. 2D is a left side elevation view, FIG. 2E is a lower perspective view, and FIG. 2F is a bottom plan view. As shown in FIG. 2A, ribs 32A-32D and curved panels 34A-34D project generally outwardly and downwardly from the frame 31. The curved panels 34A-34D preferably do not extend downward as far as the ribs 32A-32D. The top plan view provided in FIG. 2B shows that the concave shaping member 30 has a generally oval shape when viewed from above. In certain embodiments, the ribs 32A-32D, curved panels 34A-34D, and frame 31 may be fabricated of one or more pieces of material via a suitable method such as molding. As shown in FIGS. 2B-2D, gaps 33A1 to 33D2 are provided between portions of adjacent ribs 32A-32D and curved panels 34A-34D to accommodate outward expansion and inward contraction, and to enable transfer of heat and/or fluid (e.g., evaporation of sweat). The cover 42 may be substantially flush or nearly flush with a top edge of the central frame 31. As shown in FIGS. 2C and 2D, the front rib 32A may be shorter than the lateral ribs 32B, 32D and the rear rib 32C.

As shown in FIGS. 2E and 2F, the electronics housing 40 may include medial holes 40A, 40B to accommodate fasteners (not shown) for receiving the FPCB 10. The electronics housing 40 further includes corner holes 40C arranged to receive additional fasteners (not shown) for attaching the cover 42 to the electronics housing 40. Pivotal coupling between the battery holder 51 and the electronics housing 40 via pivotal coupling elements 51A is shown in FIG. 2E. As shown in FIGS. 2E and 2F, the battery holder 51 is located generally below the rear rib 32C and two rear curved panels 34B, 34C, with the battery 50 having a thin low profile shape. In one embodiment, the battery 50 is preferably a flexible battery providing at least 3.7V and at least 1000 mAh.

Various views of the FPCB 10 or portions thereof in a flat configuration are shown in FIGS. 3A-3D.

Figure 3A:
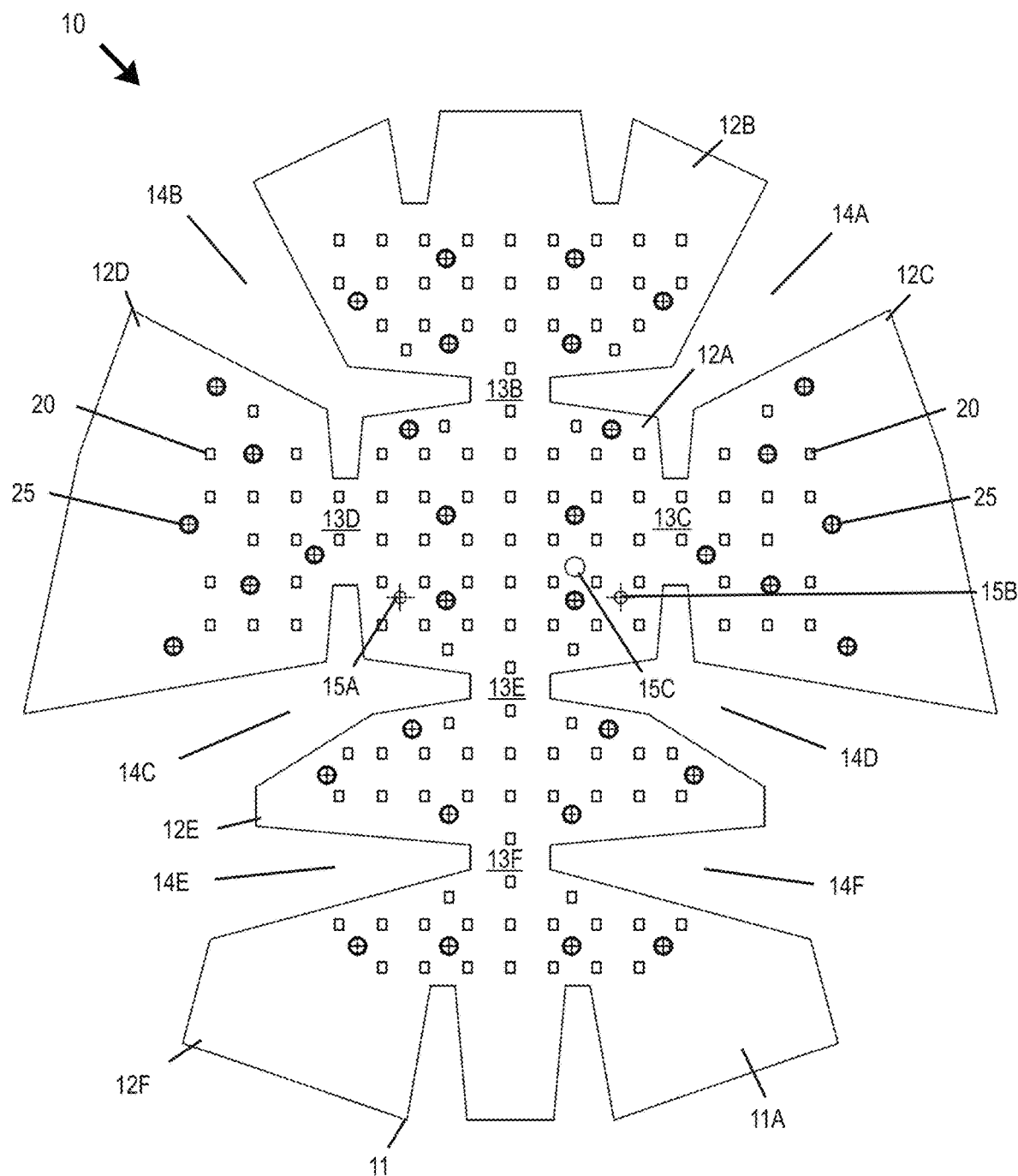
FIG. 3A is a bottom plan view of the FPCB illustrated in FIG. 1 with light emitters and standoffs arranged thereon, prior to shaping of the FPCB into a concave configuration.

FIG. 3A is a bottom plan view of the FPCB 10 with light emitters 20 and standoffs 25 arranged thereon. The FPCB 10 includes a polyimide substrate 11, an inner surface 11A, and an outer surface 11B (shown in FIGS. 1, 3E, 3G, and 3H). Preferably, the FPCB 10 is encapsulated along front and back surfaces with a suitable light-transmissive material such as PETG or silicone (not shown). In one embodiment, the light emitters 20 include a total of 280 light emitting diodes arranged as 56 strings of 5 LEDs, with a string voltage of 11V, a current limit of 5 mA, and a power consumption of 3.08 watts. FIG. 3A illustrates thirty-six standoffs 25 extending from the inner surface 11A of the FPCB 10. The FPCB 10 includes six interconnected panels 12A-12F, with the panels 12A-12F being connected to one another via narrowed tab regions 13B-13F. Gaps 14A-14F are provided between various panels 12A-12F, with such gaps 14A-14F (which are extended proximate to the narrowed tab regions 13B-13F) being useful to permit transport of heat and/or fluid (e.g., evaporation of sweat) between the panels 12A-12F. As shown in FIG. 3A, holes 15A, 15B are defined through the FPCB 10 to receive fasteners (not shown) for joining the FPCB 10 to corresponding holes 40A, 40B defined in the electronics housing 40. A further opening 15C may be provided for sensor communication between a proximity sensor (e.g., photosensor) and the interior of the FPCB 10 when shaped into a concave configuration.

Figure 3B:
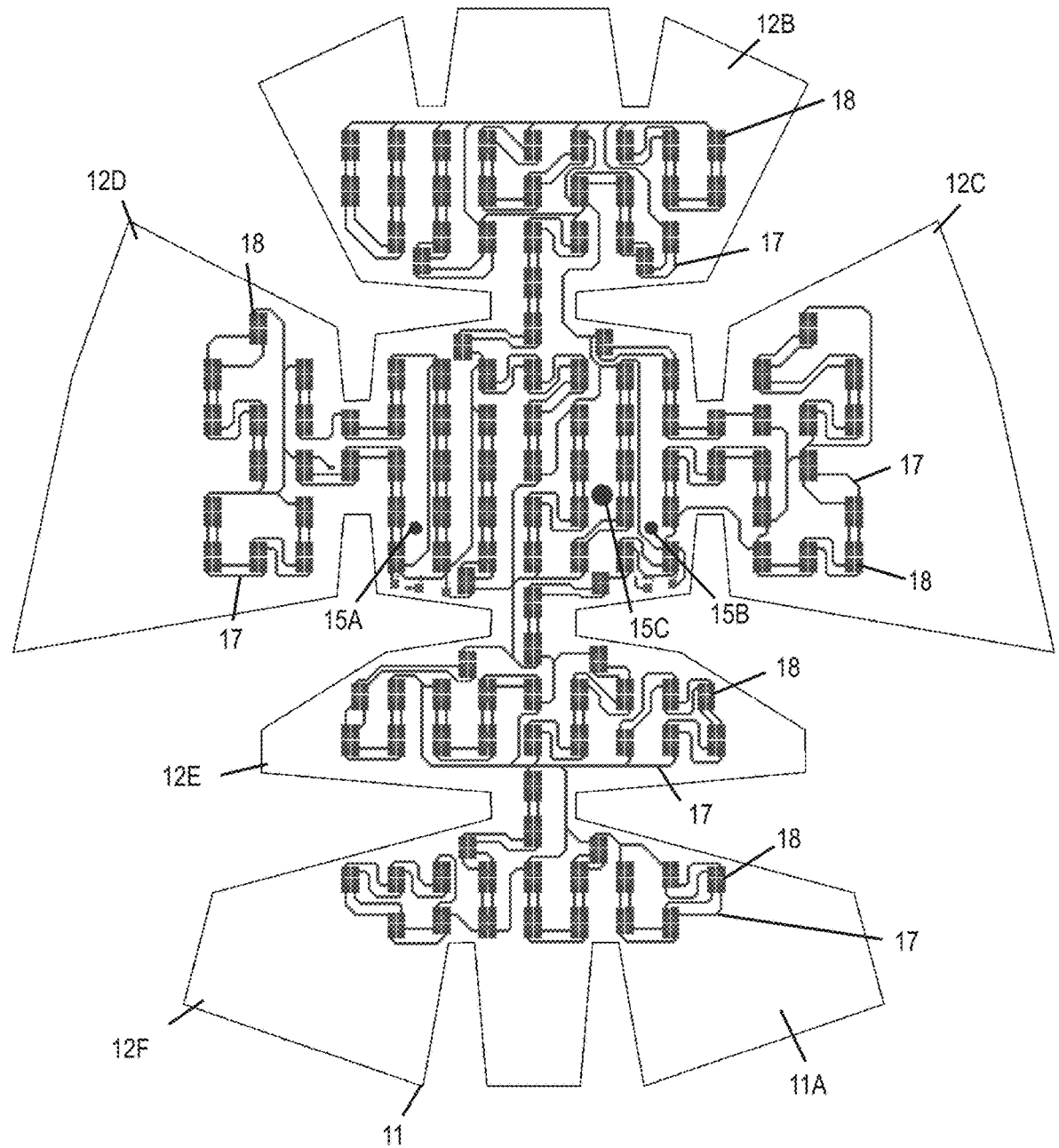
FIG. 3B is a bottom plan view of the FPCB of FIG. 3A with electrical traces and emitter mounting areas arranged thereon, prior to mounting of light emitters and formation of standoffs, and prior to shaping of the FPCB.
Figure 3C:
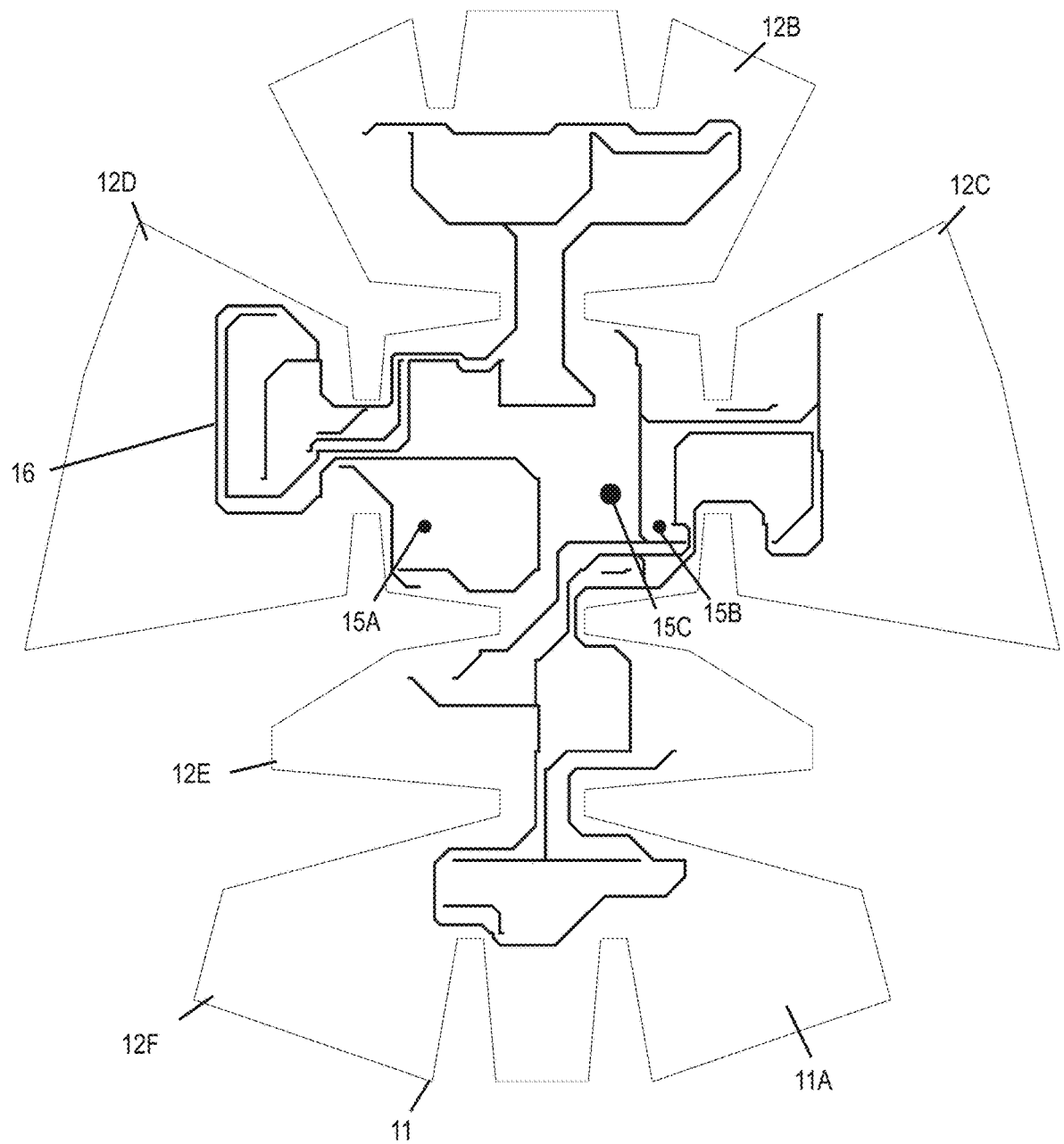
FIG. 3C is a cross-sectional view of the FPCB of FIGS. 3A and 3B viewed from the bottom, showing electrical traces along the top side of the FPCB.

FIG. 3B is a bottom plan view of the substrate 11 of the FPCB 10, showing electrical traces 17 and emitter mounting areas 18 arranged thereon, prior to mounting of light emitters and prior to formation of standoffs, and prior to shaping of the substrate 11 into a concave configuration. As shown in FIG. 3B, each emitter mounting area 18 includes two anodes and two cathodes to enable mounting of a multi-LED solid state emitter package including LEDs of different peak wavelengths. Presence of multiple anodes and cathodes at each emitter mounting area 18 permits LEDs of different peak wavelengths to be controlled differently. FIG. 3C is a cross-sectional view of the FPCB 10 viewed from the bottom (e.g., as if the substrate 11 were transparent), showing electrical traces 16 along the top side of the substrate 11.

Figure 3D:
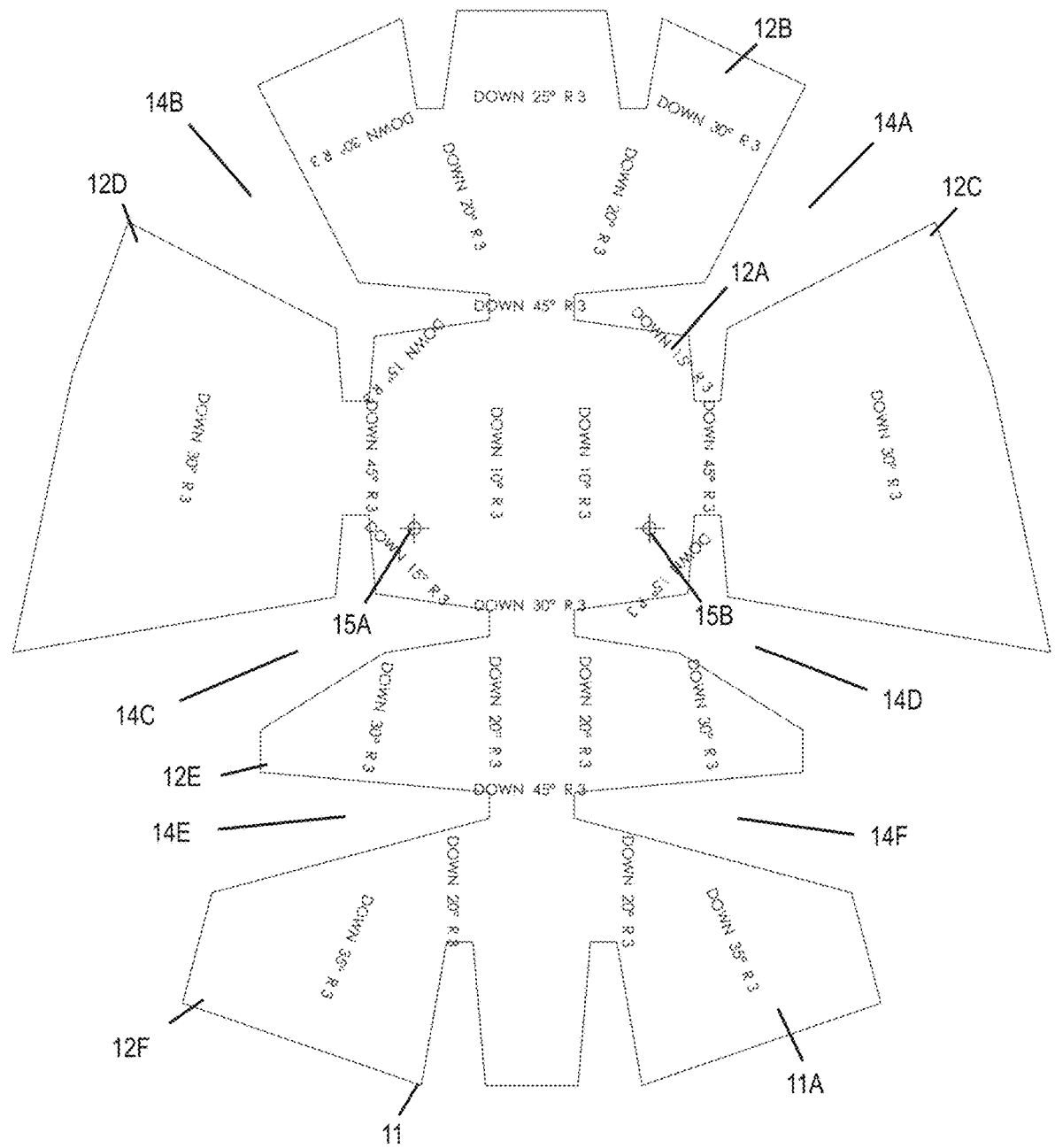
FIG. 3D is a bottom plan view of the FPCB outline of FIGS. 3A-3C, showing bending regions and bend angles useful for shaping the FPCB into a concave shape to fit around the scalp of a user.

FIG. 3D is a bottom plan view of the FPCB 10 outline, showing bending regions and bend angles useful for shaping the substrate 11 into a concave shape to fit around the scalp of a user. As shown in FIG. 3D, bending regions are provided between each panel 12A-12F, and each panel 12A-12F includes additional bending regions. The first panel 12A includes two longitudinal bending regions as well as corner bending regions. The second panel 12B includes five bending regions. The third and fourth panels 12C and 12D each include one bending region. The fifth panel 12E and the sixth panel 12F each include four bending regions.

Figure 3E:
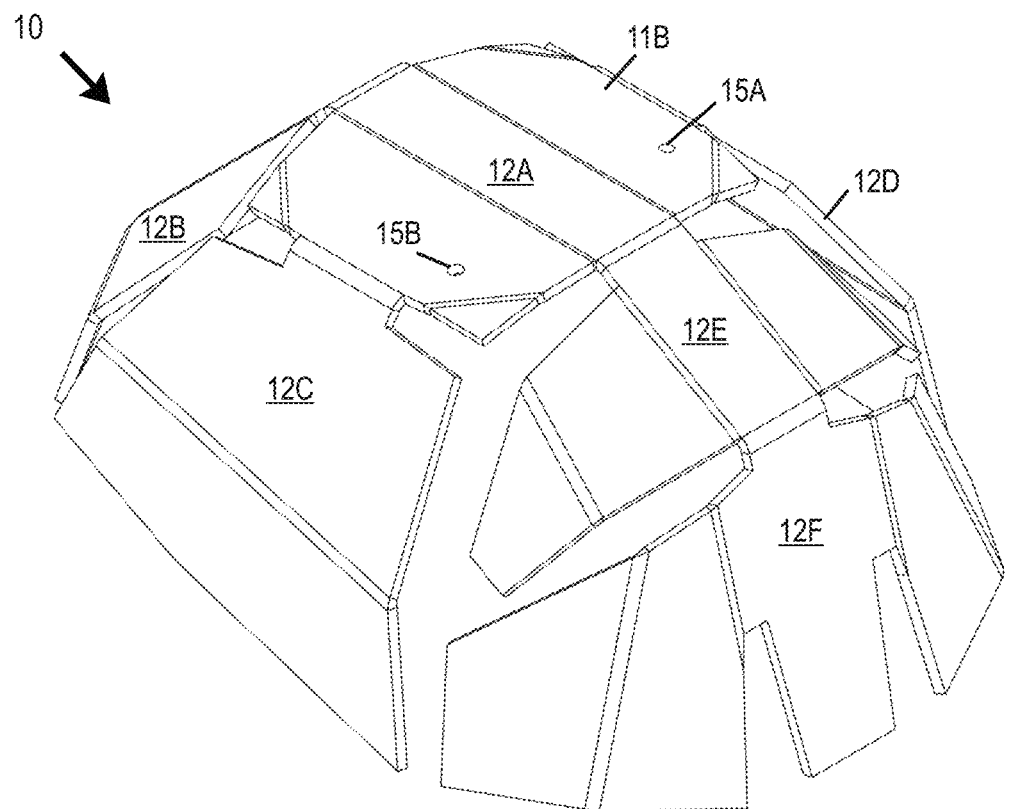
FIG. 3E is an upper perspective view of the FPCB of FIG. 3D following bending or shaping steps to form a concave shape suitable for fitting around the scalp of a user.
Figure 3F:
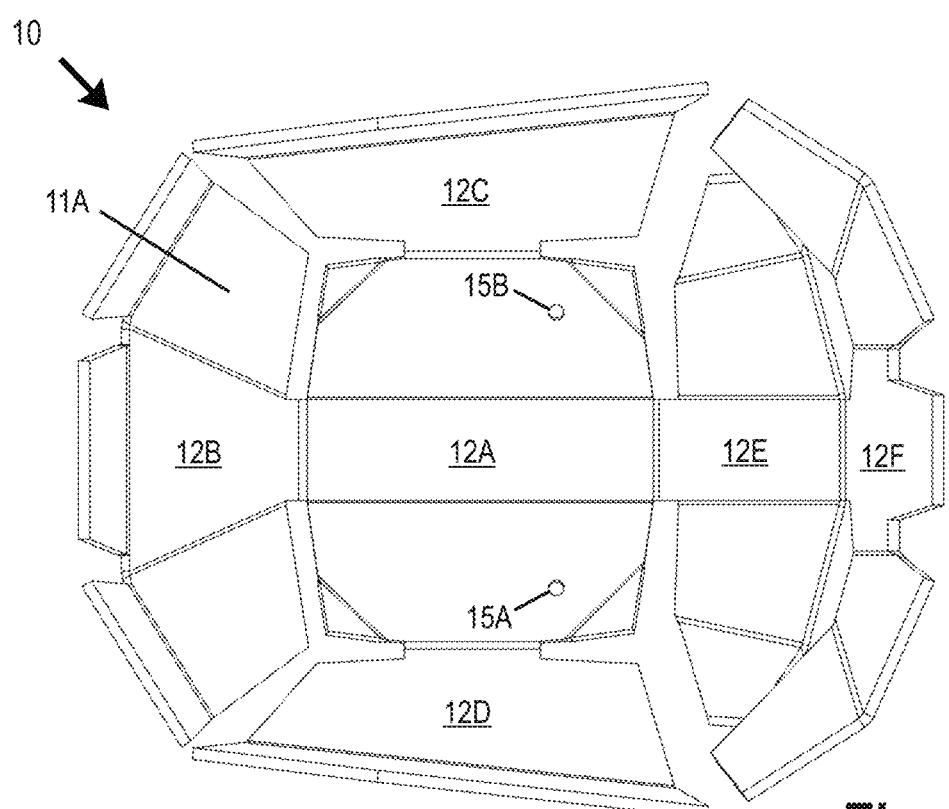
FIG. 3F is a lower plan view of the shaped FPCB of FIG. 3E, without presence of emitters, traces, emitter mounting regions or standoffs for ease of illustration.
Figure 3G:
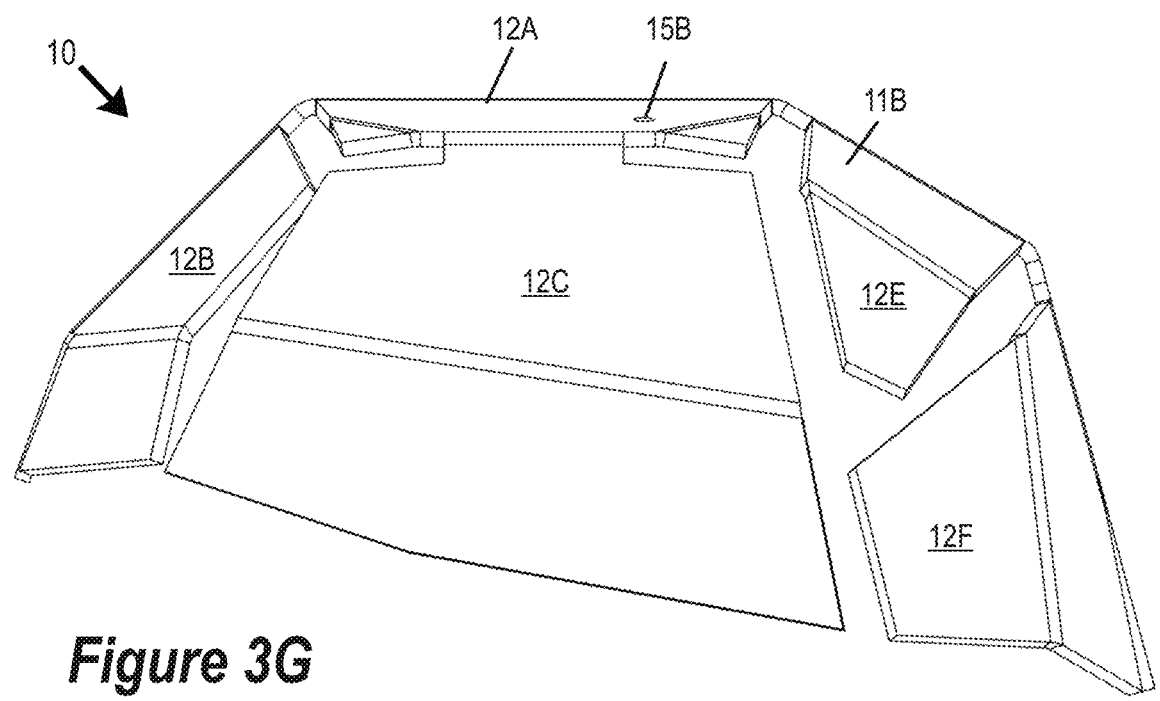
FIG. 3G is a left side elevation view of the shaped FPCB of FIGS. 3E and 3F.
Figure 3H:
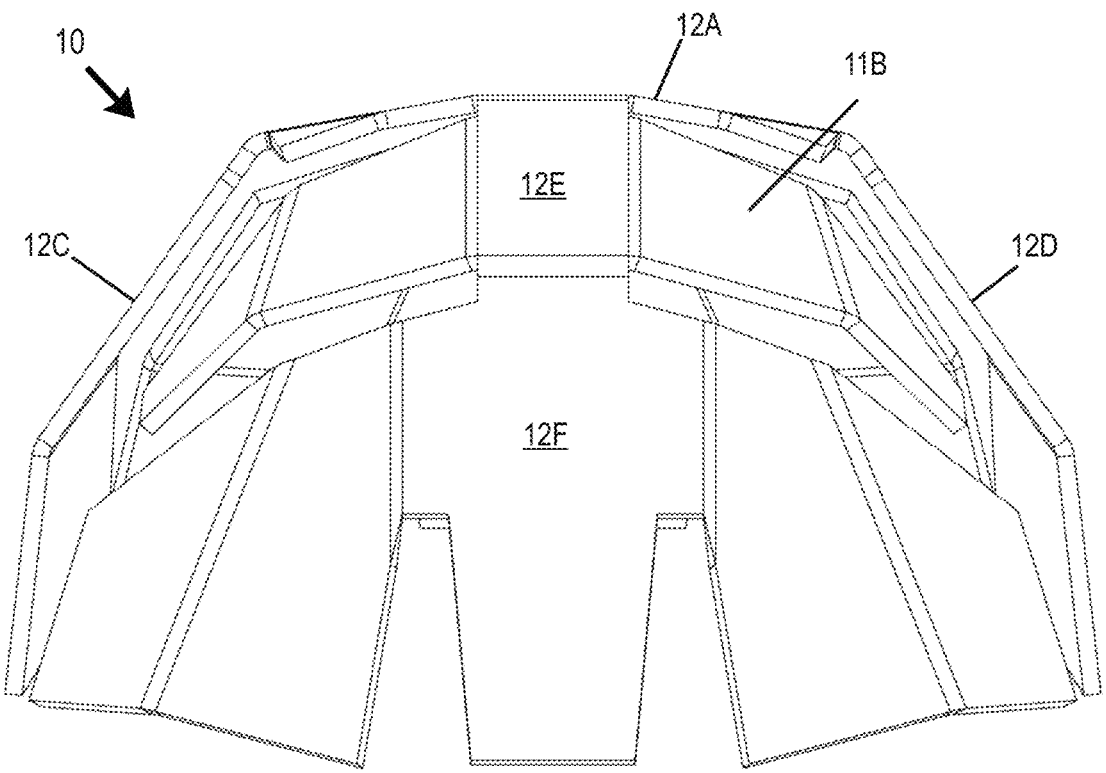
FIG. 3H is an upper front perspective view of the shaped FPCB of FIGS. 3E-3G.

FIGS. 3E-3H provide various views of the FPCB 10 in a concave configuration, including an upper perspective view (FIG. 3E), a lower plan view (FIG. 3F), a left side elevation view (FIG. 3G), and an upper front perspective view (FIG. 3H). FIGS. 3E, 3G, and 3H show an outer surface 11B of the shaped FPCB 10, whereas FIG. 3F shows the inner surface 11A. As is evident from the concave shape depicted in FIGS. 3E-3H, the first panel 12A is configured to cover a cranial crest of a user, the second panel 12B is configured to cover a portion of a user's forehead, the third and fourth panels 12C, 12D are configured to cover a user's temples, and the fifth and sixth panels 12E, 12F are arranged to cover rear portions of a user's head.

Figure 4A:
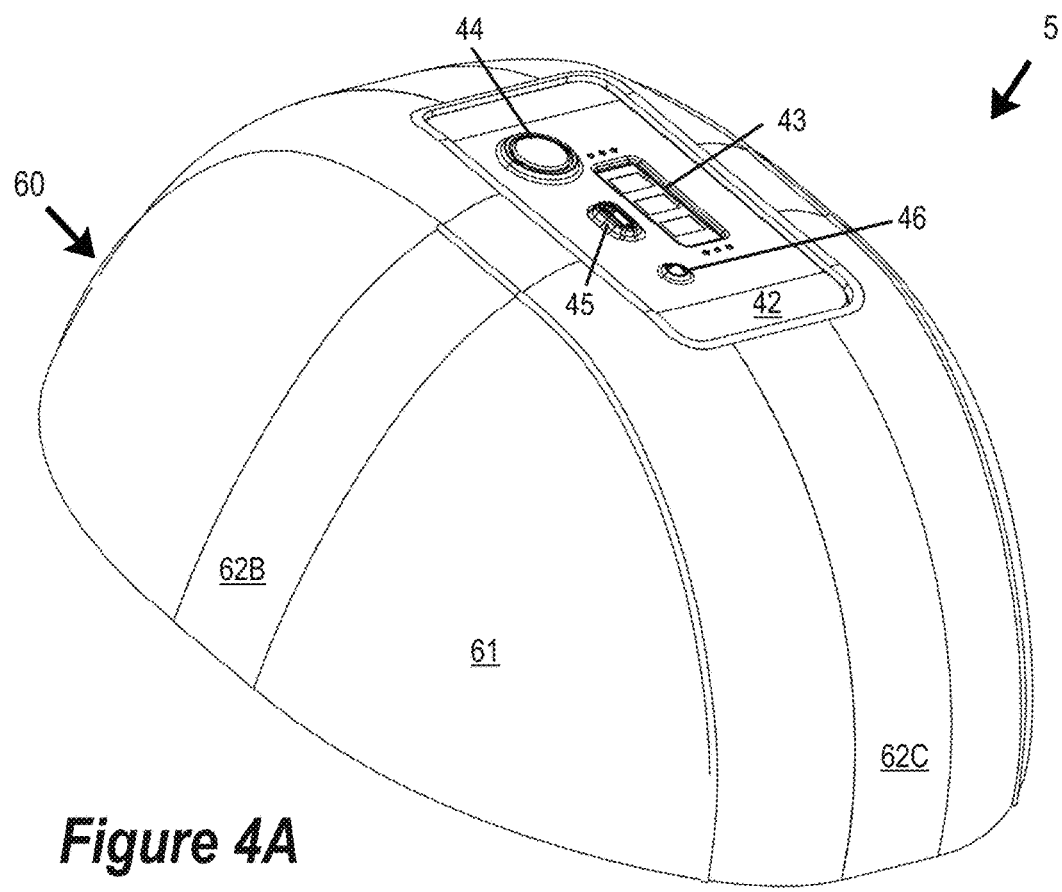
FIG. 4A is an upper perspective view of the assembled light emitting device of FIG. 1.
Figure 4B:
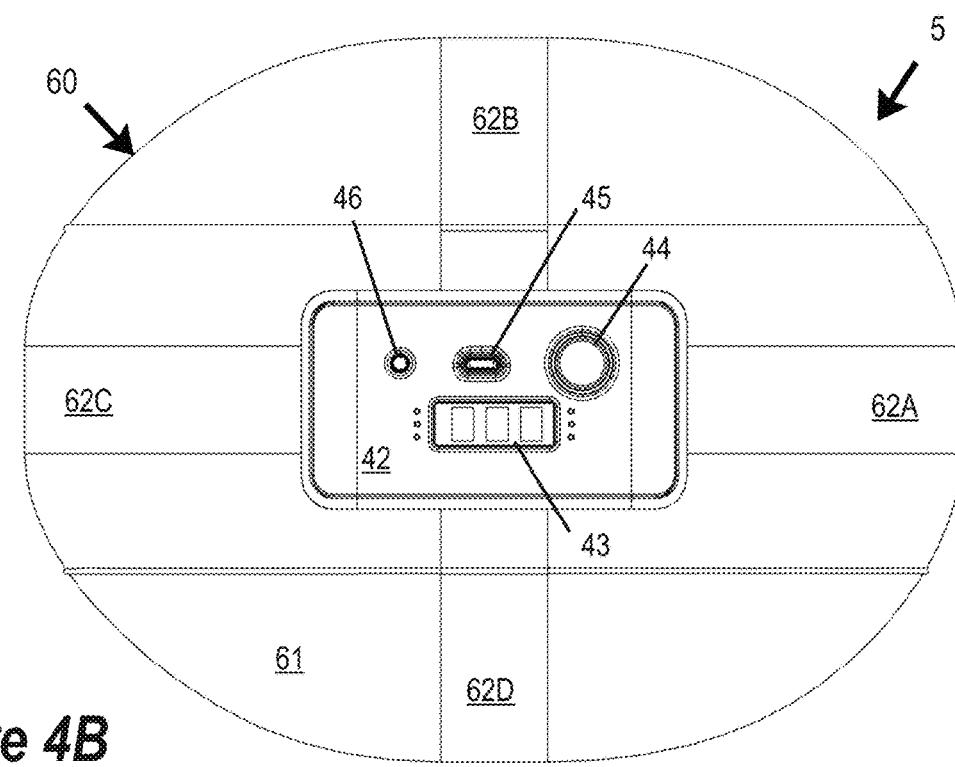
FIG. 4B is a top plan view of the assembled light emitting device of FIG. 4A.
Figure 4C:
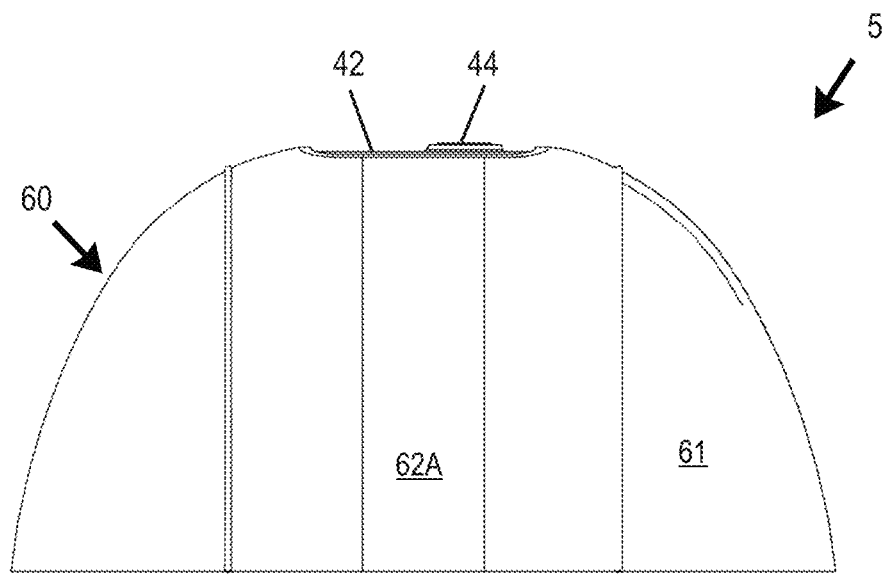
FIG. 4C is a front elevation view of the assembled light emitting device of FIGS. 4A and 4B.
Figure 4D:
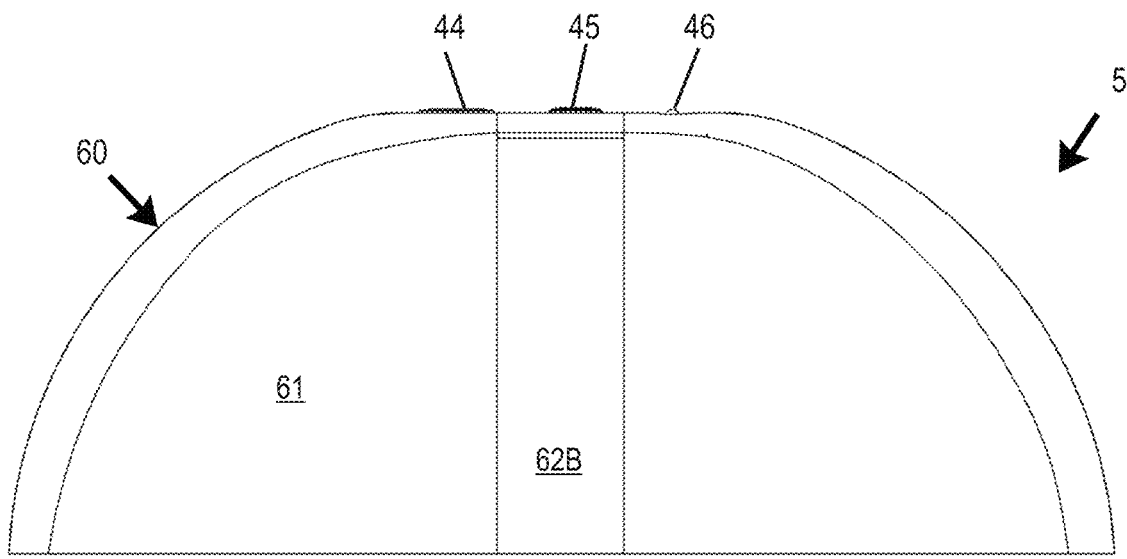
FIG. 4D is a left side elevation view of the assembled light emitting device of FIGS. 4A-4C.

FIGS. 4A-4D provide various views of the assembled device 5 of FIG. 1, including an upper perspective view (FIG. 4A), a top plan view (FIG. 4B), a front elevation view (FIG. 4C), and a left side elevation view (FIG. 4D). The majority of the outer surface of the device 5 includes the fabric covering 60, with an uppermost outer surface embodying the cover 42 for the electronics housing 40. The fabric covering 60 includes a fabric body 61 and multiple (internal) pockets 62A-62D that are arranged to receive portions of the ribs 32A-32D.

Figure 5A:
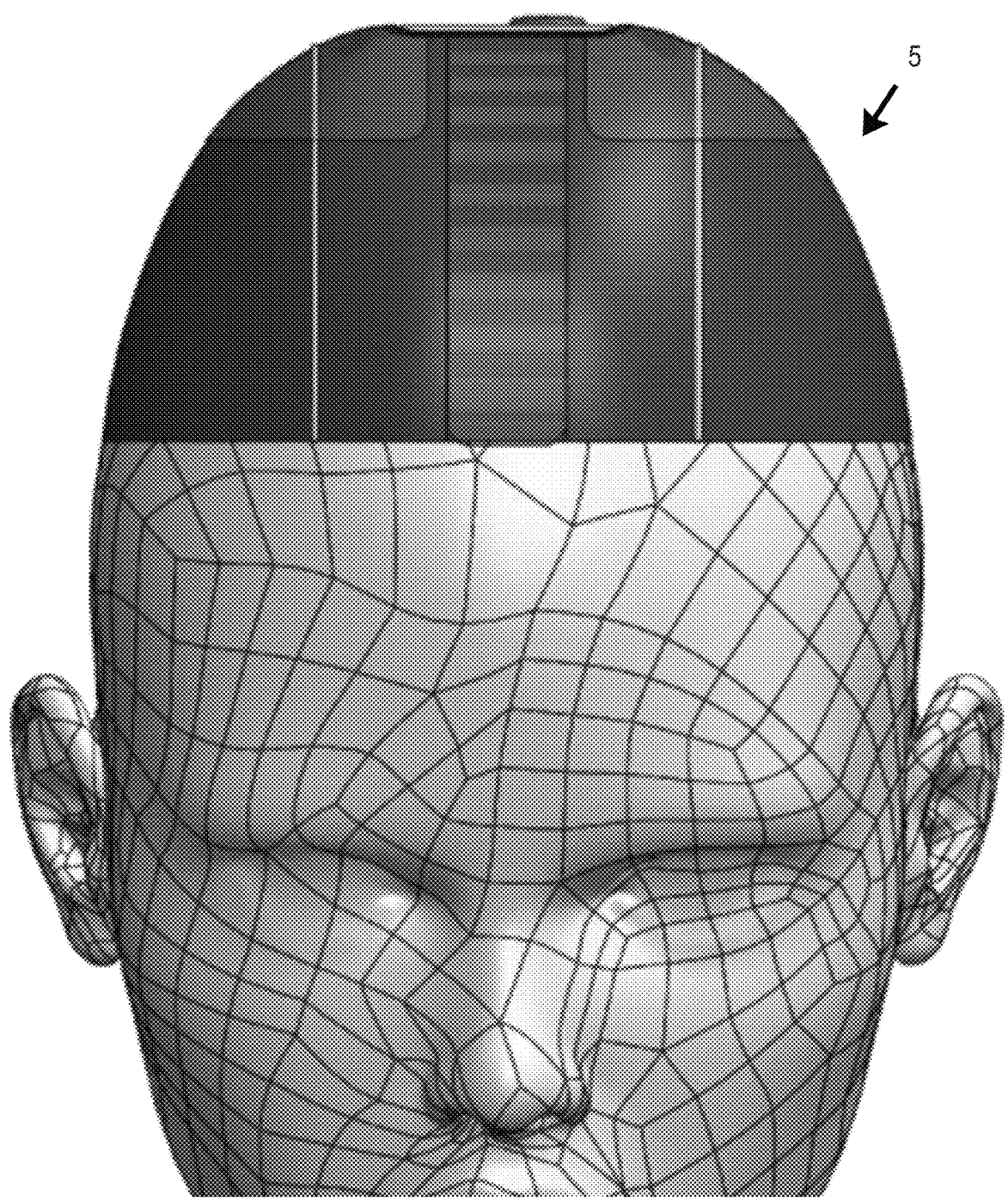
FIG. 5A is a front elevation view of the assembled light emitting device of FIGS. 4A-4D superimposed over a modeled human head.
Figure 5B:
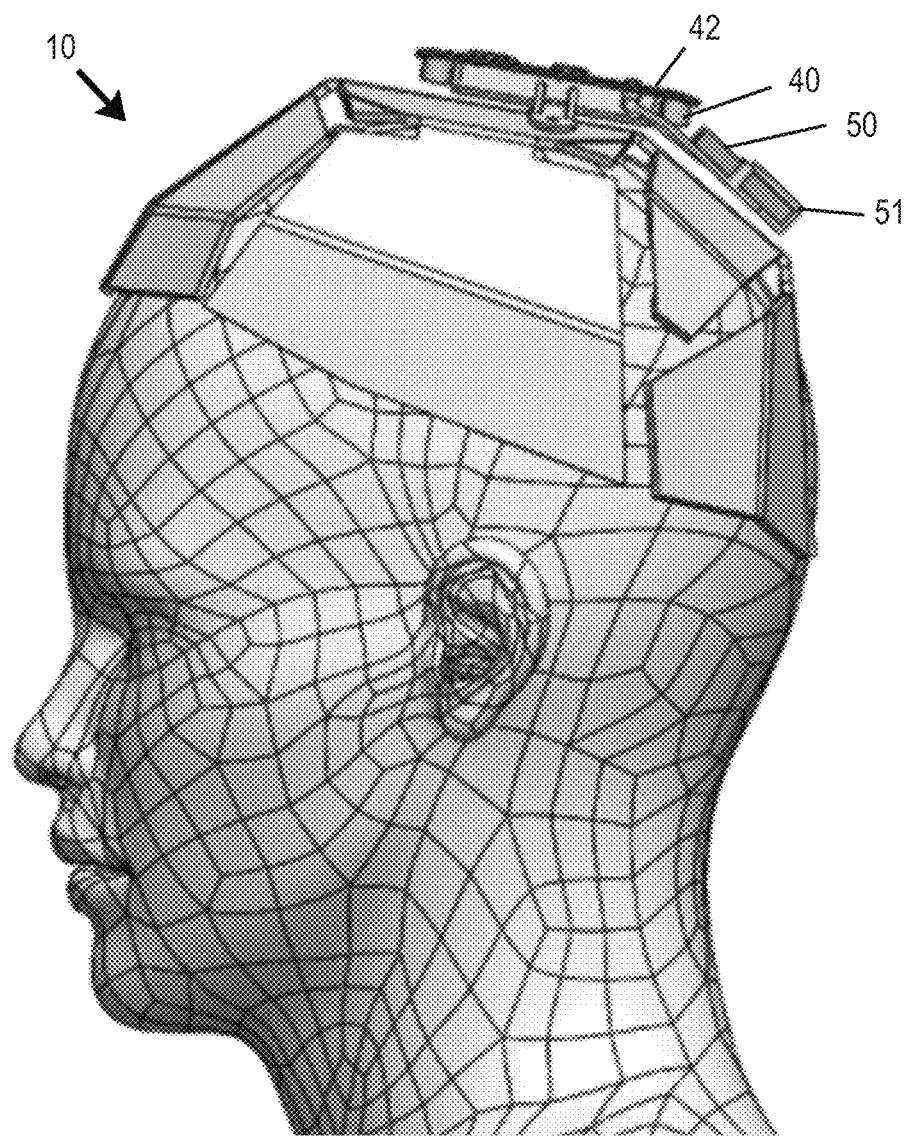
FIG. 5B is a side elevation view of a portion of the light emitting device of FIGS. 1, 4A-4D, and 5A, omitting the concave shaping member and the fabric covering.

FIG. 5A is a front elevation view of the assembled light emitting device of FIGS. 4A-4D superimposed over a modeled human head. As shown in FIG. 5A, the device 5 is embodied in a cap with a lower edge between a user's forehead and hairline, and above a user's ears. FIG. 5B is a side elevation view of a portion of the light emitting device of FIGS. 1, 4A-4D, and 5A, omitting the concave shaping member and the fabric covering to show intended placement of the FPCB 10, the electronics housing 40, the cover 42, the battery holder 51, and the battery 50 relative to a user's head. As shown in FIG. 5B, the FPCB 10 closely conforms to at least a portion of a cranial vertex of a patient.

Figure 6:
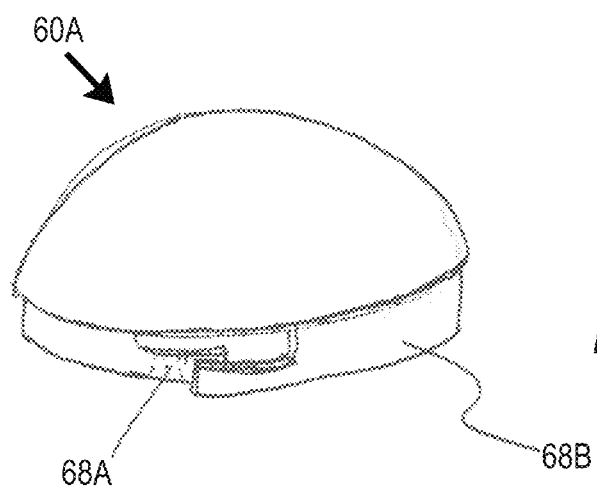
FIG. 6 is a schematic view of a fabric covering including an adjustable closure arranged to permit adjustment of an opening circumference of the fabric covering.

FIG. 6 is a schematic view of a fabric covering member 60A including an adjustable closure including portions 68A, 68B arranged to permit adjustment of an opening circumference of the fabric covering member 60A. In certain embodiments, the adjustable closure may include hook-and-loop tape, a snap closure, a selectively operable compression fitting, or fabric ends that may be tied into a knot.

FIGS. 7A-7F illustrate cross-sectional views of portions of flexible light emitting devices each including a standoff extending from an encapsulated FPCB supporting multiple light emitting elements, wherein the standoff in each case has a different shape and volume.

Figure 7A:
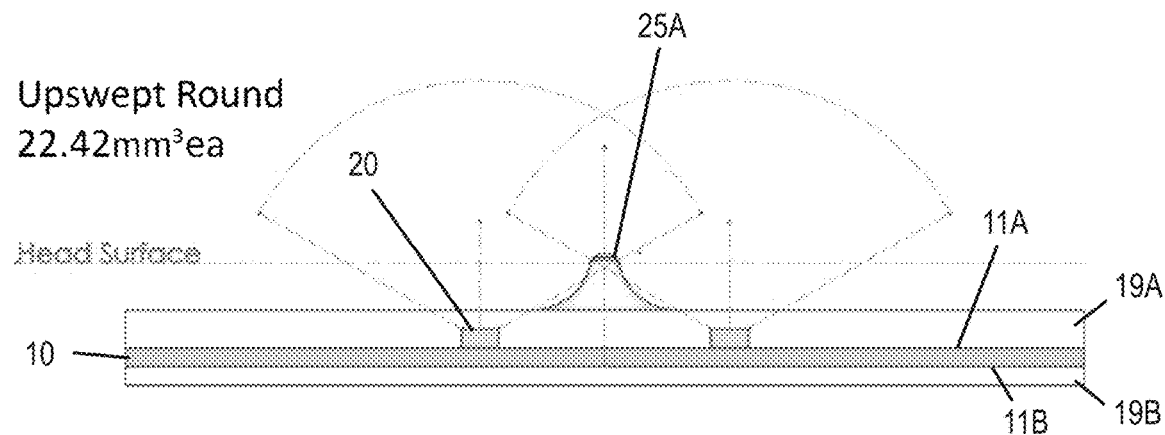
FIG. 7A is a side cross-sectional view of a portion of a first light emitting device including a standoff having an upswept round configuration extending from an encapsulated FPCB supporting multiple light emitting elements.

FIG. 7A is a side cross-sectional view of a portion of a first light emitting device including a standoff 25A having an upswept round configuration extending from a FPCB 10 supporting multiple light emitters 20. Emissions of multiple light emitters 20 overlap above the standoff 25A. Both inner and outer surfaces 11A, 11B of the FPCB 10 are covered with encapsulant material 19A, 19B. The standoff 25A has a volume of 22.42 cubic millimeters.

Figure 7B:
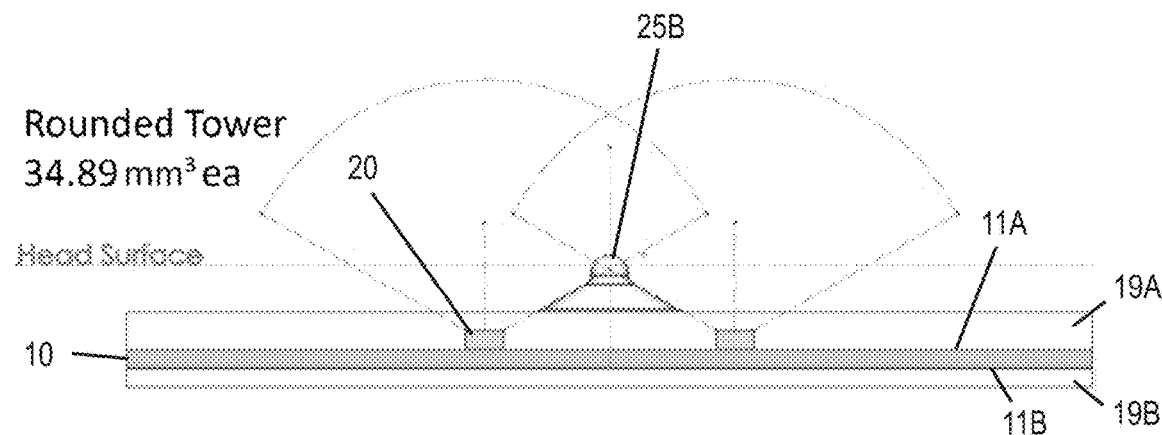
FIG. 7B is a side cross-sectional view of a portion of a second light emitting device including a standoff having a rounded tower configuration extending from an encapsulated FPCB supporting multiple light emitting elements.

FIG. 7B is a side cross-sectional view of a portion of a second light emitting device including a standoff 25B having a rounded tower configuration extending from a FPCB 10 supporting multiple light emitters 20. Emissions of multiple light emitters 20 overlap above the standoff 25B. Both inner and outer surfaces 11A, 11B of the FPCB 10 are covered with encapsulant material 19A, 19B. The standoff 25B has a volume of 34.89 cubic millimeters.

Figure 7C:
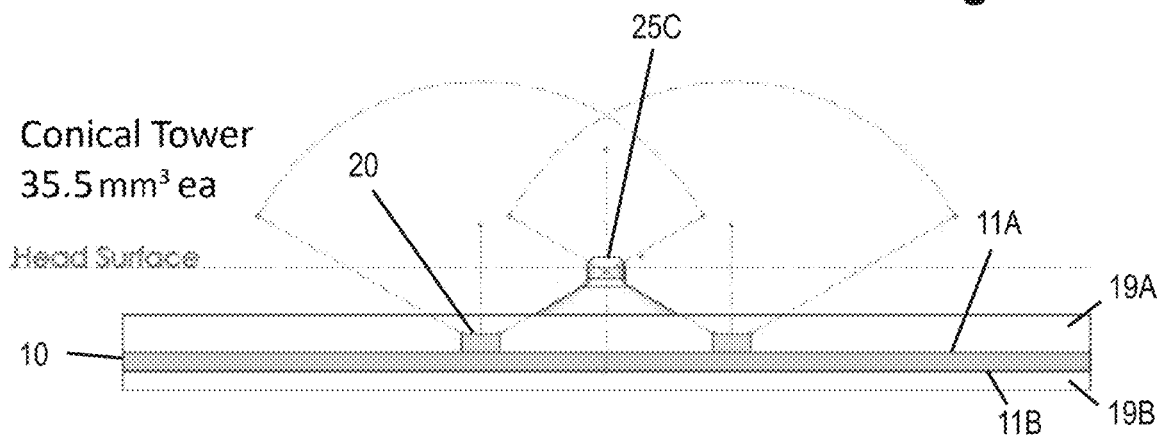
FIG. 7C is a side cross-sectional view of a portion of a third light emitting device including a standoff having a conical tower configuration extending from an encapsulated FPCB supporting multiple light emitting elements.

FIG. 7C is a side cross-sectional view of a portion of a third light emitting device including a standoff 25C having a conical tower configuration extending from a FPCB 10 supporting multiple light emitters 20. Emissions of multiple light emitters 20 overlap above the standoff 25C. Both inner and outer surfaces 11A, 11B of the FPCB 10 are covered with encapsulant material 19A, 19B. The standoff 25C has a volume of 35.5 cubic millimeters.

Figure 7D:
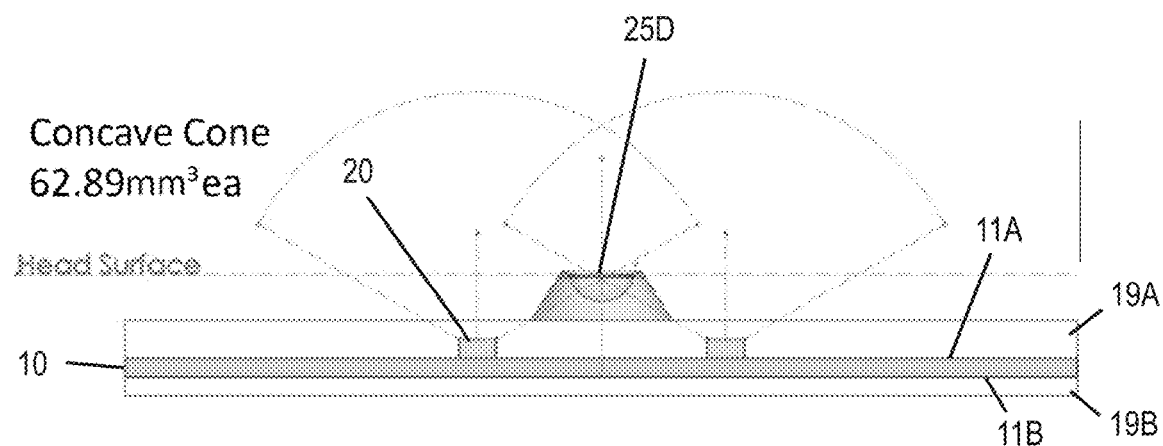
FIG. 7D is a side cross-sectional view of a portion of a fourth light emitting device including a standoff having a concave cone configuration extending from an encapsulated FPCB supporting multiple light emitting elements.

FIG. 7D is a side cross-sectional view of a portion of a fourth light emitting device including a standoff 25D having a concave cone configuration extending from a FPCB 10 supporting multiple light emitters 20. Emissions of multiple light emitters 20 overlap above the standoff 25D. Both inner and outer surfaces 11A, 11B of the FPCB 10 are covered with encapsulant material 19A, 19B. The standoff 25D has a volume of 62.89 cubic millimeters.

Figure 7E:
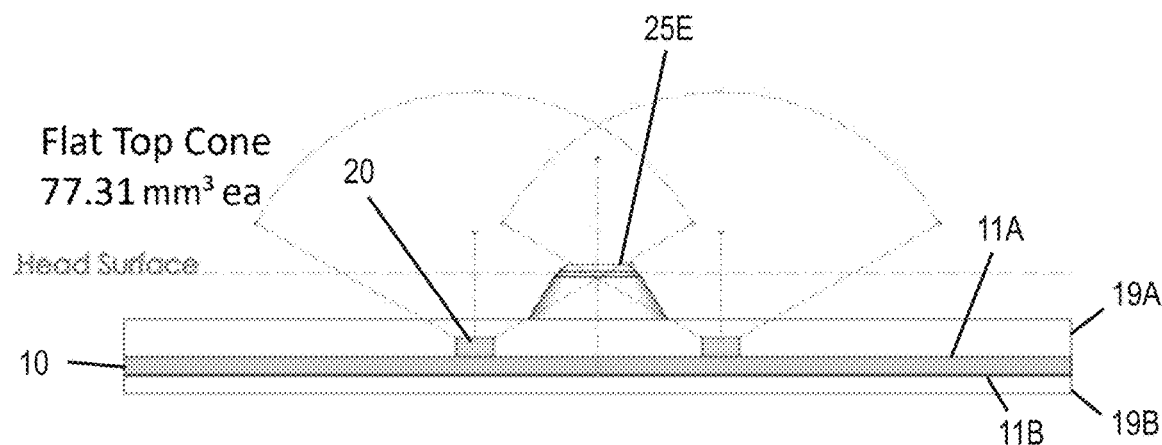
FIG. 7E is a side cross-sectional view of a portion of a fifth light emitting device including a standoff having a flat top cone configuration extending from an encapsulated FPCB supporting multiple light emitting elements.

FIG. 7E is a side cross-sectional view of a portion of a fifth light emitting device including a standoff 25E having a flat top cone configuration extending from a FPCB 10 supporting multiple light emitters 20. Emissions of multiple light emitters 20 overlap above the standoff 25E. Both inner and outer surfaces 11A, 11B of the FPCB 10 are covered with encapsulant material 19A, 19B. The standoff 25E has a volume of 77.31 cubic millimeters.

Figure 7F:
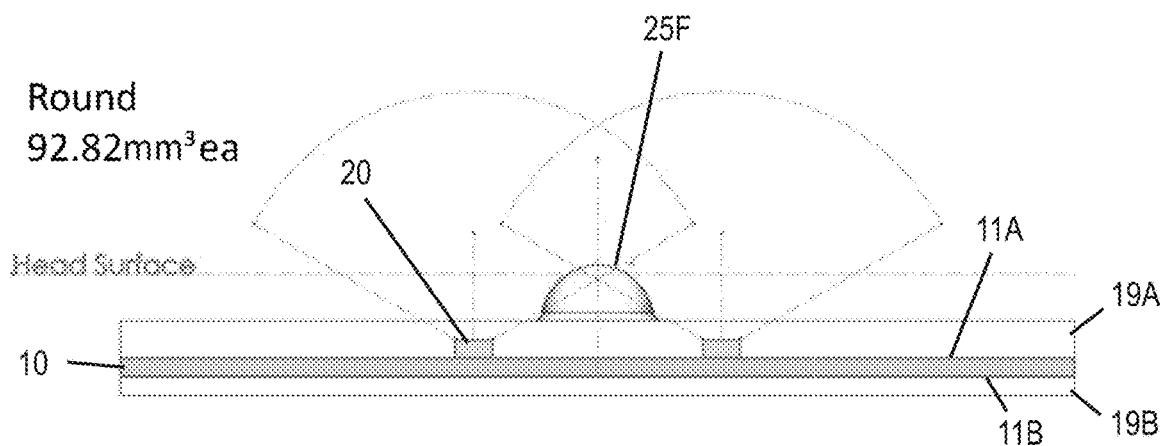
FIG. 7F is a side cross-sectional view of a portion of a sixth light emitting device including a standoff having a round configuration extending from an encapsulated FPCB supporting multiple light emitting elements.

FIG. 7F is a side cross-sectional view of a portion of a sixth light emitting device including a standoff 25F having a round configuration extending from a FPCB 10 supporting multiple light emitters 20. Emissions of multiple light emitters 20 overlap above the standoff 25F. Both inner and outer surfaces 11A, 11B of the FPCB 10 are covered with encapsulant material 19A, 19B. The standoff 25F has a volume of 92.82 cubic millimeters.

As shown in FIGS. 7A-7F, various standoff shapes and sizes may be used, depending on considerations such as user comfort, material volume, and light interaction and/or light blocking characteristics.

Figure 8:
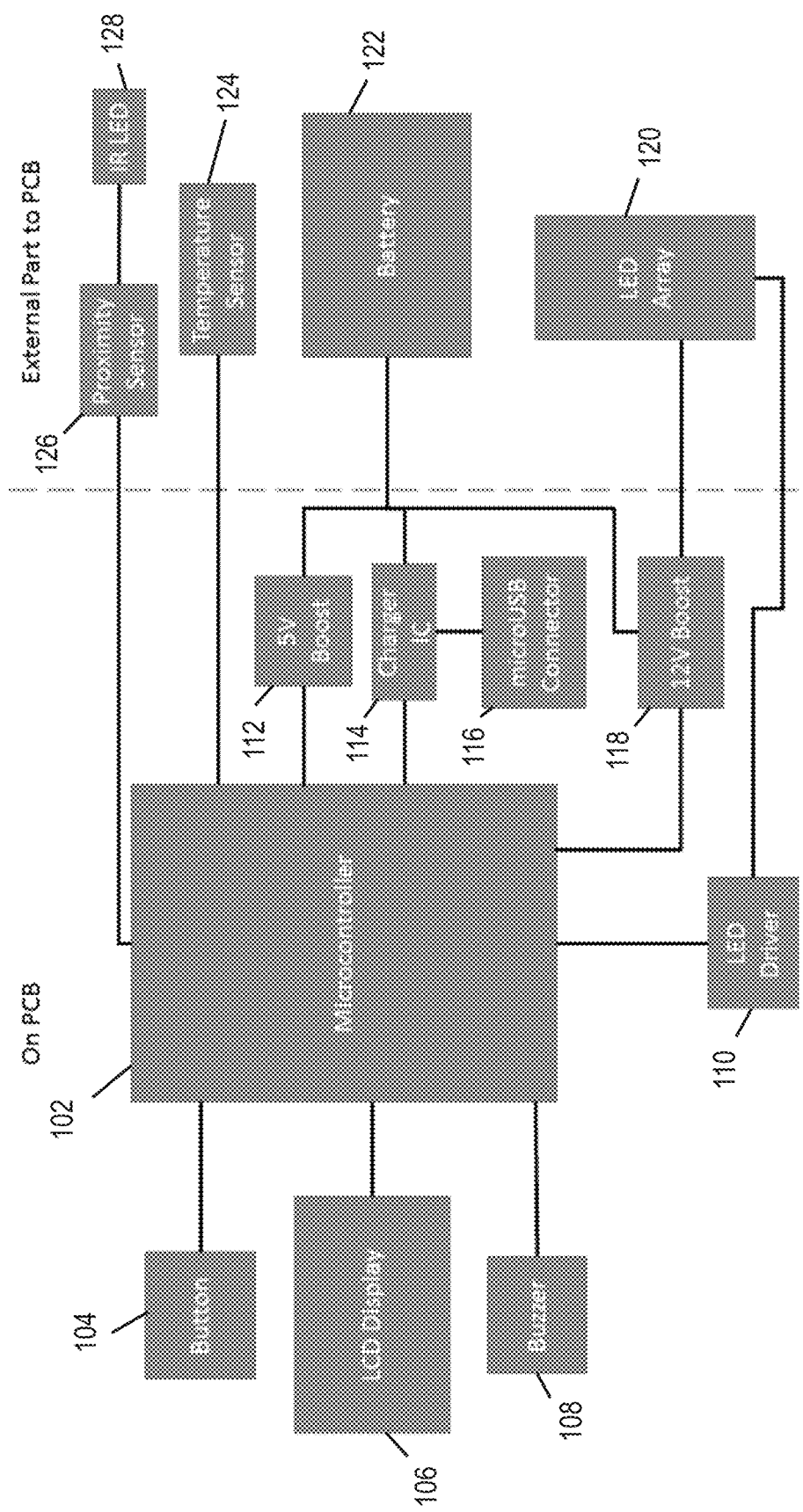
FIG. 8 is a schematic diagram showing interconnections between components of a light emitting device for delivering light energy to a scalp of a patient according to one embodiment.

FIG. 8 is a schematic diagram showing interconnections between components of a light emitting device for delivering light energy to a scalp of a patient according to one embodiment. A microcontroller 102 is arranged to receive power from a battery 122 (nominally 3.7V) via a 5V voltage boost circuit 112. The microcontroller 102 may be arranged to control a charging integrated circuit 114 arranged between a microUSB connector 116 and the battery 122, wherein the microUSB connector 116 may be used to receive current for charging the battery 122. In certain embodiments, the microUSB connector 116 may also be used for communicating data and/or instructions to or from the microcontroller 102 and/or an associated memory. The microcontroller 102 is also arranged to control a 12V boost circuit 118 for increasing voltage to one or more LED arrays 120. The microcontroller 102 further controls one or more LED driver circuits 110 arranged to drive the one or more LED arrays 120. The microcontroller 102 is also arranged to receive inputs from a user input button 104, a temperature sensor 124, and a proximity sensor 126 (which includes an infrared LED 128). The microcontroller 102 is further arranged to provide output signals to a LCD display 106 and a buzzer 108. Certain components are located off-board relative to a controller FPCB, as indicated by the vertical dashed line in FIG. 8. In operation of the light emitting device, a user may depress the button 104 to start operation. If the proximity sensor 126 detects that the device has been placed on a user's head, then the microcontroller 102 may trigger the one or more LED driver circuits 110 to energize the one or more LED arrays 120. Temperature during operation is monitored with the temperature sensor 124. If an excess temperature condition is detected, then the microcontroller 102 may take appropriate action to reduce current supplied by the one or more LED driver circuits 110 to the one or more LED arrays 120. Operation may continue until a timer (e.g., internal to the microcontroller 102) causes operation to terminate automatically. One or more indicator LEDs (not shown) may provide a visible signal indicative of charging status of the battery 122. Audible signals for commencement and termination of operation may be provided by the buzzer 108 or a suitable speaker. Information relating to usage cycles, usage time, or any other suitable parameter may be displayed by the LCD display 106.

Figure 9:
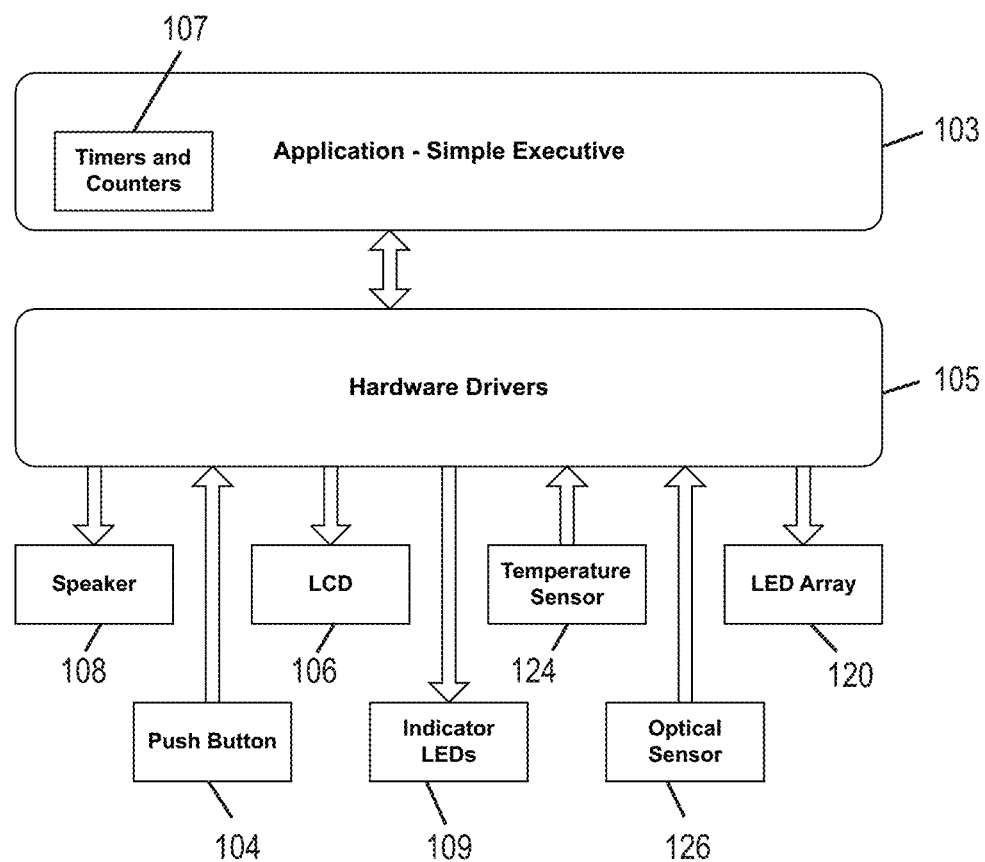
FIG. 9 is a schematic diagram depicting an interface between hardware drivers, functional components, and a software application suitable for operating a light emitting device for delivering light energy to a scalp of a patient according to one embodiment.

FIG. 9 is a schematic diagram depicting an interface between hardware drivers, functional components, and a software application suitable for operating a light emitting device for delivering light energy to a scalp of a patient, according to one embodiment. Application executive functions 103, including timers and counters 107, may be performed with one or more integrated circuits (such as the microcontroller 102 illustrated in FIG. 8). Hardware drivers 105 may be used to interface with various input and output elements, such as the one or more LED arrays 120, the speaker or buzzer 108, the LCD display 106, the temperature sensor 124, the user input button 104 (e.g., push button), indicator LEDs 109, and the optical sensor 126.

Figure 10A:
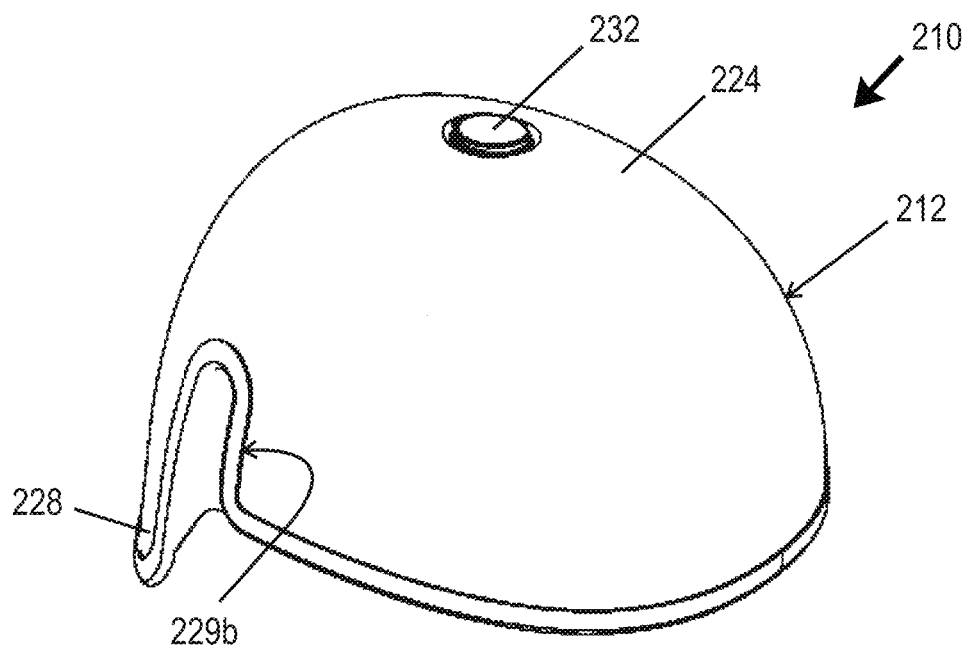
FIG. 10A is an upper perspective view of a light emitting device for phototherapy embodied in a wearable cap for delivering light energy to a scalp of a patient, the phototherapy device including a flexible cap, a flexible printed circuit board (FPCB) with at least one light emitting device (LED), a flexible lenticular lens, and a plurality of standoffs, according to one embodiment.
Figure 10B:
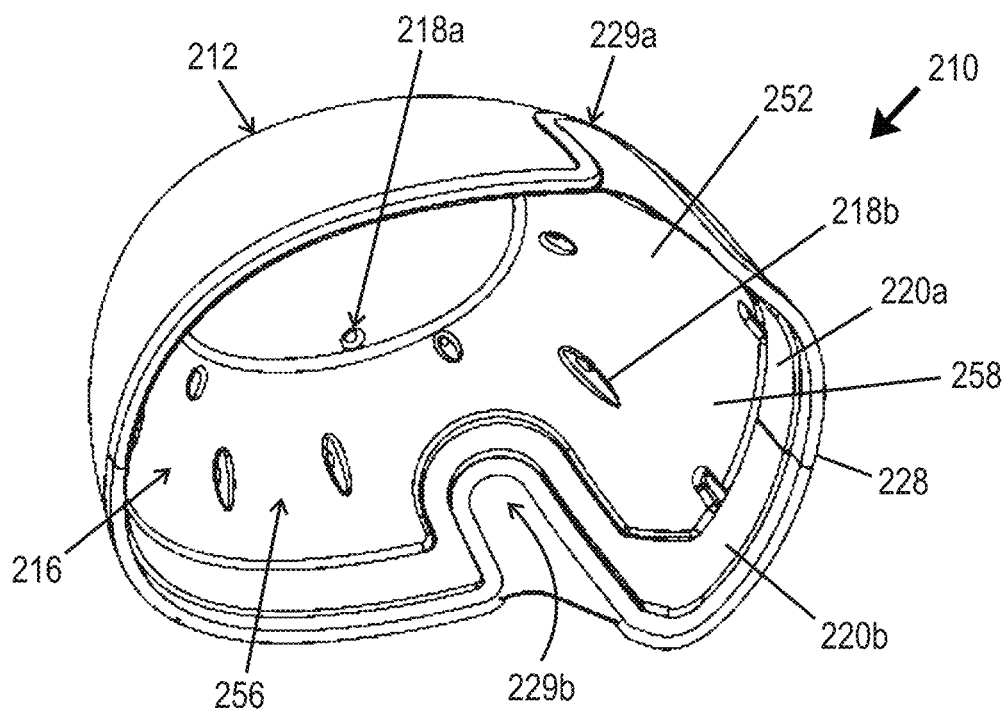
FIG. 10B is a lower perspective view of the phototherapy device of FIG. 10A.
Figure 10C:
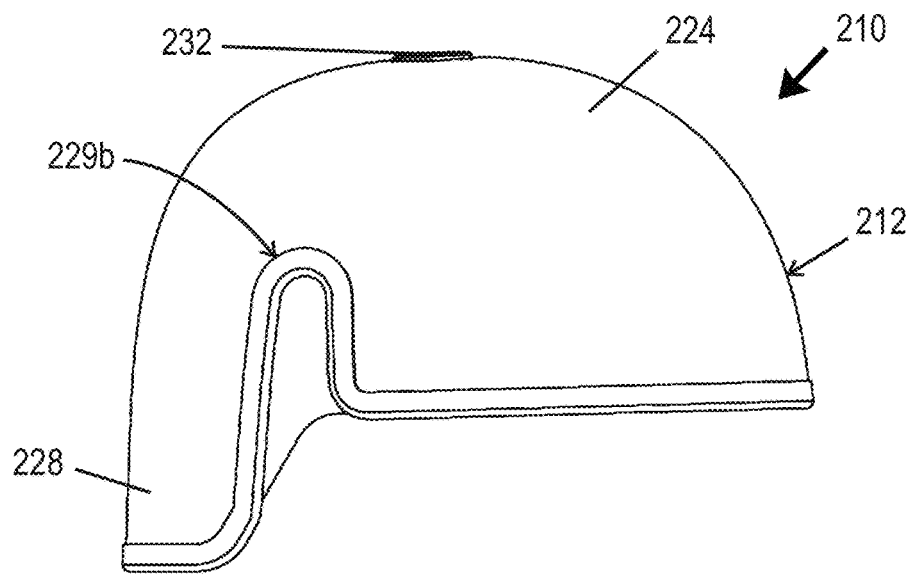
FIG. 10C is a right side elevation view of the phototherapy device of FIGS. 10A and 10B.
Figure 10D:
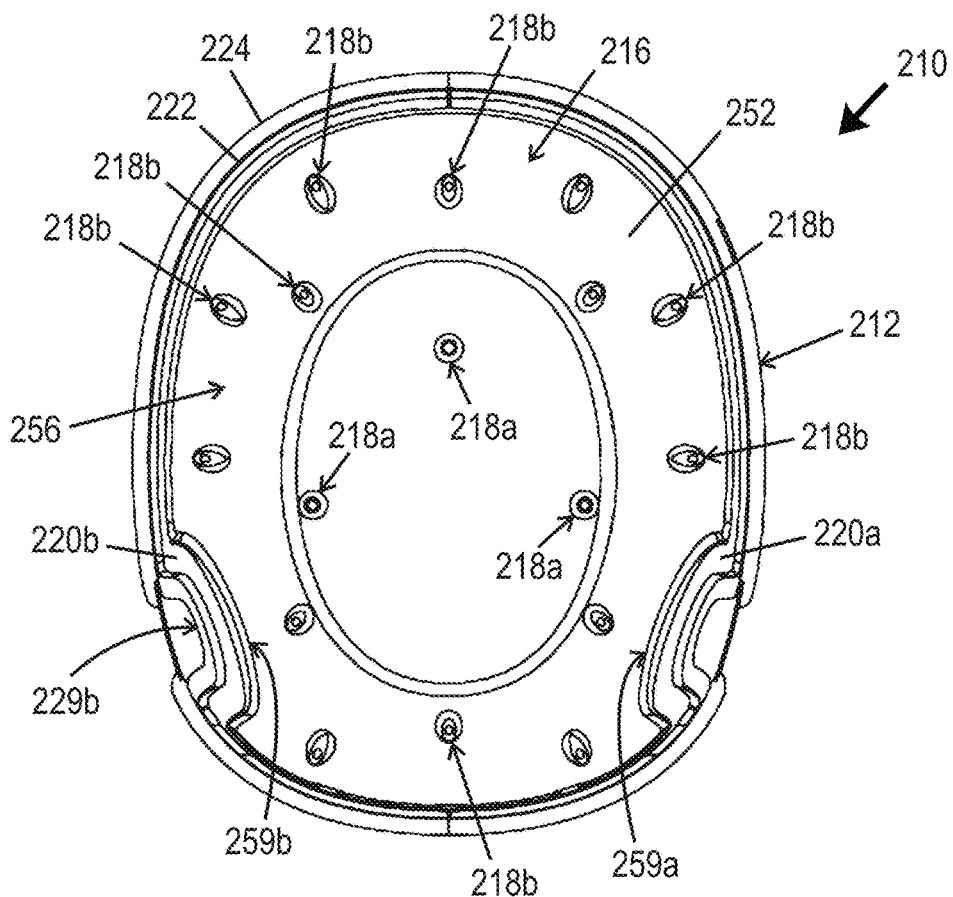
FIG. 10D is a bottom plan view of the phototherapy device of FIGS. 10A-10C.
Figure 10E:
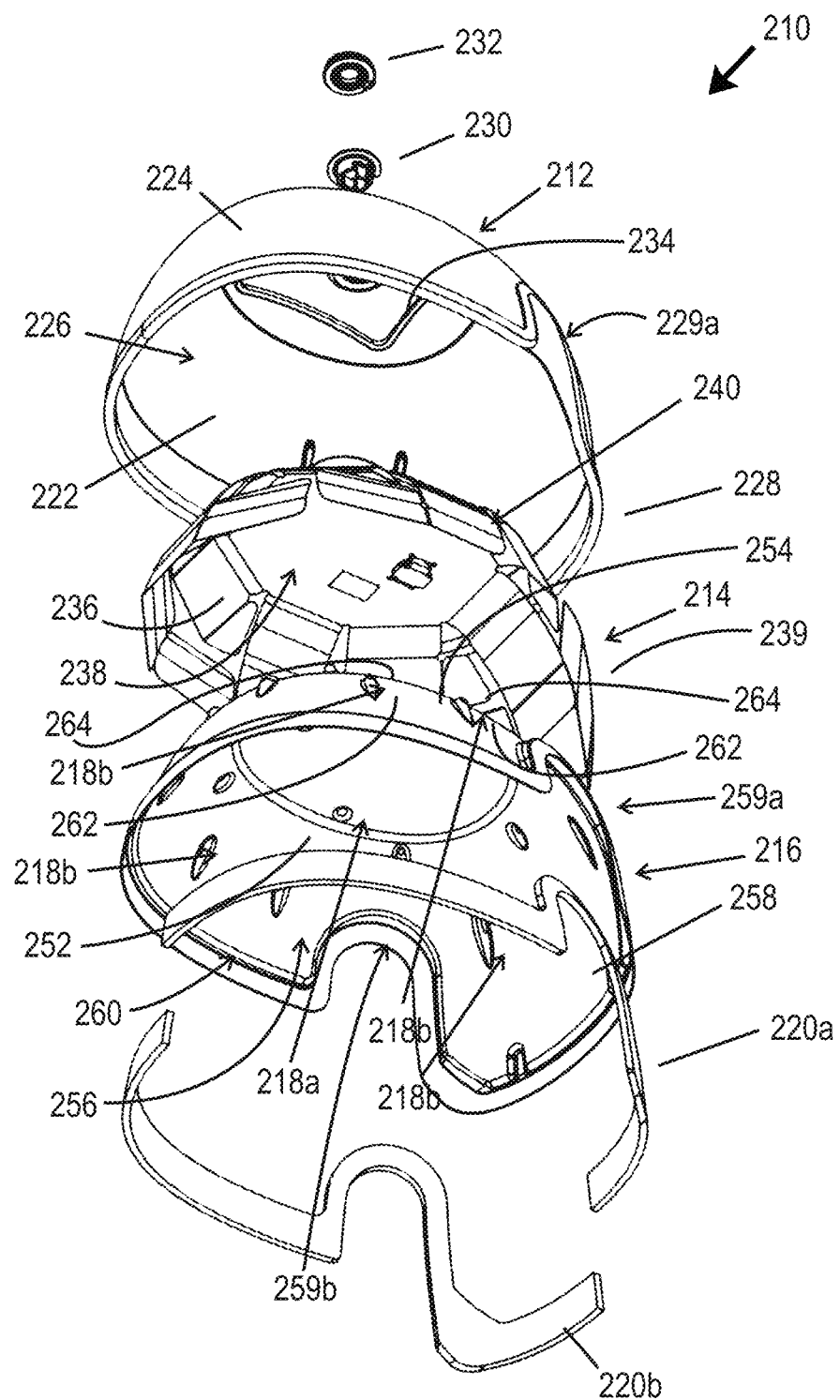
FIG. 10E is an exploded view of the phototherapy device of FIGS. 10A-10D.

FIGS. 10A-10E illustrate a phototherapy device for delivering light energy to a scalp of a patient according to another embodiment. More specifically, FIG. 10A is an upper perspective view, FIG. 10B is a lower perspective view, FIG. 10C is a right side elevation view, FIG. 10D is a bottom plan view, and FIG. 10E is an exploded view of the phototherapy device. As discussed in more detail below, the phototherapy device 210 may include a flexible cap 212, a flexible printed circuit board (FPCB) assembly 214, a flexible lenticular lens 216, a plurality of standoffs 218a, 218b, foam padding 220a, 220b, and a binding edge 221 (shown in FIGS. 13A and 13B).

The flexible cap 212 may comprise one or more different fabrics or materials (e.g., cotton, open or closed cell polyethylene foam, polyester, rayon, etc.), and may be formed in a variety of different shapes and sizes depending on the head dimensions of the patient. In certain embodiments, the flexible cap 212 comprises a stretchable material to accommodate a variety of head sizes. The flexible cap 212 includes a proximal surface 222 (e.g., which may variously be described as a bottom surface, lower surface, inner surface, inside surface, or surface proximate to the patient) and a distal surface 224 (e.g., which may variously be described as a top surface, upper surface, outer surface, outside surface, or surface further from the patient). The flexible cap 212 forms a concavity 226 generally sized and shaped to receive an upper portion of a head of a patient, and may include a posterior extension 228 configured to cover the lower rear portion of a patient's head (e.g., the nape, posterior hairline, occipital protuberance, and/or proximate thereto, etc.). Proximate to the posterior extension 228 (but towards the center of the flexible cap 212), the flexible cap 212 may include a flex arc (e.g., left flex arc 229a and right flex arc 229b), which allows the posterior extension 228 to more easily flex outward to accommodate varying head sizes.

In certain embodiments, the flexible cap 212 may include a seal plug 232 removably attached to and covering an electronic connection port 230 at a top of the flexible cap 212. The electronic connection port 230 is mechanically attached to an electronics receptacle 234 arranged at a top of the flexible cap 212. The seal plug 232 covers and protects the electronic connection port 230 from damage when not in use. The electronics receptacle 234 may be configured to receive an electronics subassembly 250 of a FPCB assembly 214 (show in FIGS. 11A and 11B and discussed in more detail below) to provide mechanical stability to the electronics subassembly 250. For example, the electronics receptacle 234 may be mechanically attached and secured to the electronics subassembly 250 to prevent relative movement therebetween. The electronic connection port 230 (with the electronics receptacle 234) may provide mechanical and/or electronic connectivity between the electronics subassembly 250 with an electronic device (e.g., computer, smartphone, etc.) external to the phototherapy device 210 or electronic connector (e.g., power cord, USB cord, etc.) to receive electrical power and/or electronic data (e.g., operational parameters). In certain embodiments, wireless communication may be provided between the phototherapy device 210 and an electronic device. In certain embodiments, a battery operatively coupled to the FPCB assembly 214 may be inductively charged (e.g., wirelessly charged).

The FPCB assembly 214 (discussed in more detail below) includes a proximal surface 236 (which may variously be referred to as a bottom surface, lower surface, inner surface, inside surface, or surface proximate to the patient) and a distal surface 237 (which may variously be referred to as a top surface, upper surface, outer surface, outside surface, or surface further from the patient). The FPCB assembly 214 forms a concavity 238 generally sized and shaped to receive at least an upper portion of the head of a patient, and may include a posterior extension 239 configured to cover the lower rear portion of a patient's head (e.g., the nape, posterior hairline, occipital protuberance, and/or proximate thereto, etc.). The proximal surface 236 includes at least one light emitting device (e.g., LED), and may include a plurality of LED devices, configured to generate emissions having one or more peak wavelengths (e.g., red LEDs and/or blue LEDs), as discussed in more detail above.

The flexible lenticular lens 216 includes a proximal surface 252 (e.g., inner surface, inside surface, surface proximate to the patient) and a distal surface 254 (e.g., outer surface, outside surface, surface further from the patient). The flexible lenticular lens 216 forms a concavity 256 generally sized and shaped to the head of a patient, and may include a posterior extension 258 configured to cover the lower part of a back of a patient's head (e.g., the nape, posterior hairline, occipital protuberance, and/or proximate thereto, etc.). Proximate the posterior extension 258 (but towards the center of the flexible lenticular lens 216), the flexible lenticular lens 216 may include a flex arc 259a, 259b, which allows the posterior extension 258 to more easily flex outward to accommodate varying head sizes. The flexible lenticular lens 216 may be molded, may have a thickness of approximately 0.02 in. to 0.06 in. (e.g., approximately 0.033 in.), and may have a lens density in a range of from about 10 to about 80 lenses per inch, or from about 20 to about 60 lenses per inch, or from about 30 to about 50 lenses per inch, or about 40 lenses per inch (LPI), although other dimensions may be used. Depending on the materials used, if a flexible lenticular lens 216 has a thickness smaller than about 0.02 inch, then undesirable wrinkling or crinkling may result, and if a flexible lenticular lens 216 has a thickness greater than 0.02 inch, it may be insufficiently flexible or stretchable to accommodate head sizes of different patients.

In certain embodiments, a flexible lenticular lens 216 may include a padding recess 260 along a peripheral edge of the flexible lenticular lens 216 to receive the foam padding 220a, 220b (such that the foam padding 220a, 220b contacts the flexible lenticular lens proximal surface 252). In this manner, the padding recess 260 and the foam padding 220a, 220b may be generally complementary to each other in size and/or shape. In certain embodiments, the padding recess 260 and foam padding 220a, 220b may be configured to extend along the entire peripheral edge of the flexible lenticular lens 216 or a portion thereof. The foam padding 220a, 220b provides an additional layer of comfort and a compressible layer for an improved fit to the patient's head. In certain embodiments, the foam padding 220a, 220b may be removably attached to the flexible lenticular lens proximal surface 252 (e.g., by Velcro), such that the foam padding 220a, 220b may be washable and/or replaceable.

The FPCB assembly 214 is positioned between the flexible cap 212 and the flexible lenticular lens 216. More specifically, the FPCB assembly 214 is positioned within the flexible cap concavity 226 such that the FPCB assembly distal surface 237 is proximate to the flexible cap proximal surface 222. The flexible lenticular lens 216 is positioned within the FPCB assembly concavity 238 such that the flexible lenticular lens distal surface 254 is positioned proximate the FPCB assembly proximal surface 236. In this manner, when the flexible cap 212, FPCB assembly 214, and flexible lenticular lens 216 are assembled together, the concavities and peripheral edges thereof are generally aligned with one another. In the same manner, the flexible cap concavity 226, FPCB concavity 238, and flexible lenticular lens concavity 256 are all generally aligned with one another; the flexible cap posterior extension 228, the FPCB assembly posterior extension 239, and the flexible lenticular lens posterior extension 258 are all generally aligned with one another; and the flexible cap flex arc 229a, 229b and flexible lenticular lens flex arc 259 are generally aligned with one another. A binding edge clip 221 (shown in FIG. 13B) may be positioned along a peripheral edge of the flexible cap 212, FPCB assembly 214, and flexible lenticular lens 216 to secure them together (e.g., the binding edge clip 221 being inwardly biased).

The plurality of standoffs 218a, 218b may include top standoffs 218a positioned at or along a top of the flexible lenticular lens 216, and side standoffs 218b positioned at or along a side of the flexible lenticular lens 216. Each standoff 218a, 218b includes a proximal end 262 and a distal end 264. The standoffs 218a, 218b are positioned between the flexible lenticular lens 216 and the FPCB assembly 214. In certain embodiment, the standoffs 218a, 218b may be attached to (e.g., by adhesive), or may be integrally formed with, the flexible lenticular lens 216 (e.g., by molding the standoffs 218a, 218b concurrently with the flexible lenticular lens 216). More specifically, for each standoff 218a, 218b, the standoff proximal end 262 contacts (and extends from) the flexible lenticular lens distal surface 254, and the standoff distal end 264 may contact the FPCB assembly proximal surface 236, such that the distance between the FPCB assembly proximal surface 236 and the flexible lenticular lens distal surface 254 is not less than a height of the standoff 218a, 218b. The height of the standoff 218a, 218b may be greater than a height of the LED (of a plurality of LEDs) to prevent the flexible lenticular lens distal surface 254 from contacting the LED (and/or any of the plurality of LEDs). The standoffs 218a, 218b maintain a minimum distance between the flexible lenticular lens distal surface 254 and the FPCB assembly proximal surface 236, as discussed below in more detail.

Figure 11A:
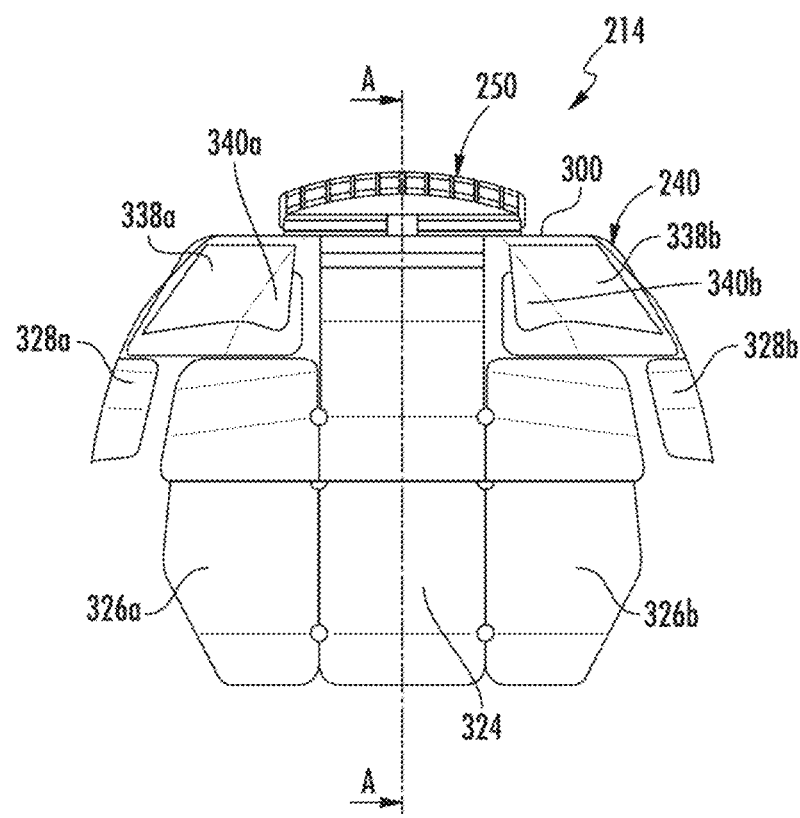
FIG. 11A is rear elevation view of the flexible printed circuit board (FPCB) assembly shown in FIG. 10E, the FPCB assembly including a panel subassembly and an electronics subassembly.
Figure 11B:
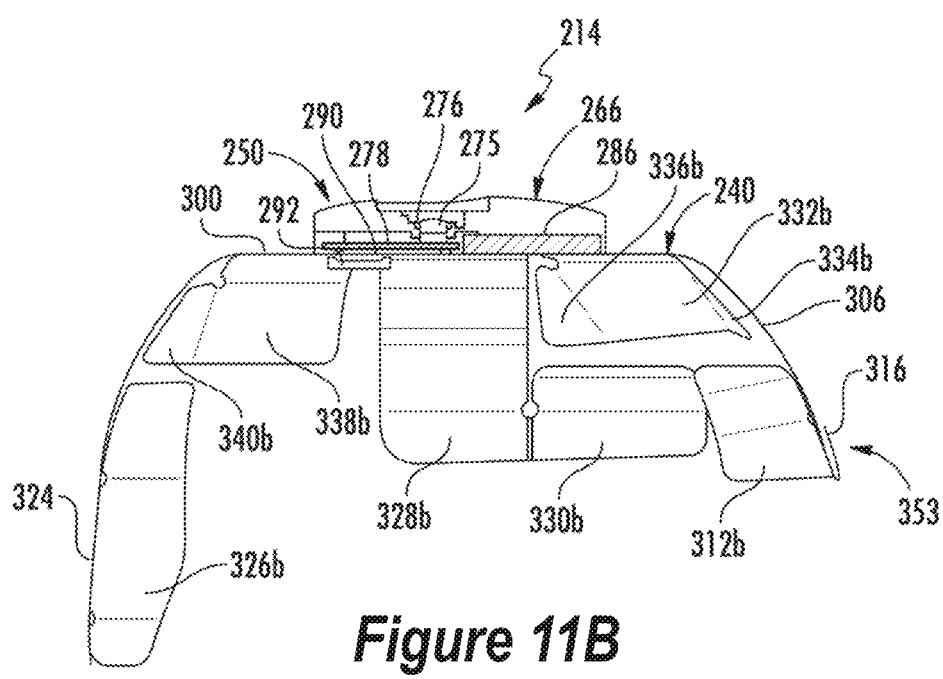
FIG. 11B is a side cross-sectional view of the FPCB assembly of FIG. 11A, taken along section line A-A illustrated in FIG. 11A.
Figure 11C:
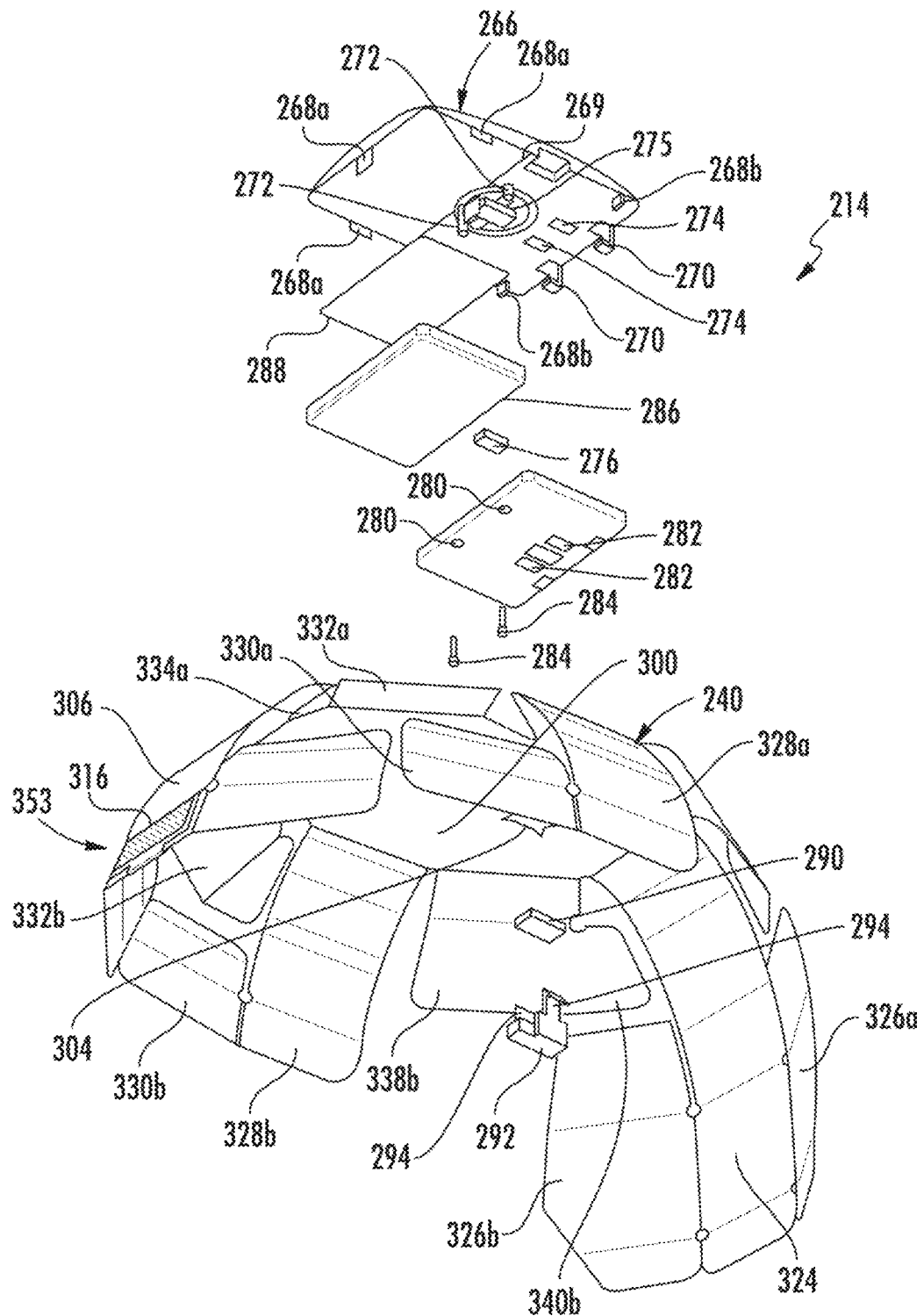
FIG. 11C is an exploded view of the FPCB assembly of FIGS. 11A and 11B.

FIGS. 11A-11C are views of the FPCB assembly 214. More specifically, FIG. 11A is rear elevation view, FIG. 11B is a side cross sectional view, and FIG. 11C is an exploded view of the FPCB assembly 214. The FPCB assembly 214 includes a panel subassembly 240 (e.g., multiple interconnected FPCB panels or elements) and an electronics subassembly 250. The electronics subassembly 250 is attached to the panel subassembly 240 by a mount 266, which also houses electronic circuitry therein. The mount 266 includes a plurality of attachments extending from a bottom surface thereof, with the plurality of attachments including tabs 268a, 268b, engagement prongs 270, screw posts 272, prong receptacles 274, and the like. The mount 266 also includes an electronics port 275 extending therethrough. In certain embodiments, the electronics port 275 may be embodied an electronics connector providing mechanical and electronic communication between an external electronics device or connector and the electronics subassembly 250 (explained in more detail below).

The electronics subassembly 250 also includes an O-ring 276 positioned around the electronics port 275 at a bottom surface of the mount 266. The electronics subassembly 250 further includes a control printed circuit board (PCB) 278 which includes driver circuitry for controlling operation of the panel subassembly 240 (and the LEDs mounted thereto). The control PCB 278 includes a plurality of attachments including screw apertures 280 and prong apertures 282. The screw apertures 280 receive screws 284 therethrough, which extend into mount screw posts 272, thereby attaching the control PCB 278 to a bottom surface of the mount 266 (although any other suitable fastener or attachment means may be used). The tabs 268b and/or a ridge 269 opposite thereto further secure the control PCB 278 to the mount 266 by preventing lateral movement of the control PCB 278 relative to the mount 266 (the tabs 268b may also be inserted into grooves or apertures in the panel subassembly 240).

The electronics port 275 is aligned with connector circuitry of the control PCB 278 and the flexible cap electronics receptacle 234 (shown in FIG. 10E) to provide electronic and/or mechanical access of the PCB electronics connector to an external electronic device (e.g., computer, smartphone, etc.) or electronic connector (e.g., power cord, USB cord, etc.) to receive electrical power and/or electronic communications (e.g., instructions, software updates, operational parameters, operating data, and the like).

The electronics subassembly 250 further includes a battery 286 attached to the bottom surface of the mount 266 by a battery attachment 288 (e.g., adhesive film, mechanical element, etc.). A FPCB lock pad 290 is positioned on the FPCB assembly proximal surface 236 and aligned with a FPCB snap lock 292. The FPCB snap lock 292 includes engagement prongs 294 (e.g., outwardly biased) that extend through slots 304 of the panel subassembly 240, through the control PCB prong apertures 282, and through the mount prong receptacles 274, thereby securing the panel subassembly 240, control PCB 278, and mount 266 to one another. Accordingly, the control PCB 278 and battery 286 are positioned adjacent to one another, and both contact (or are positioned proximate to) the FPCB assembly distal surface 237.

Figure 12A:
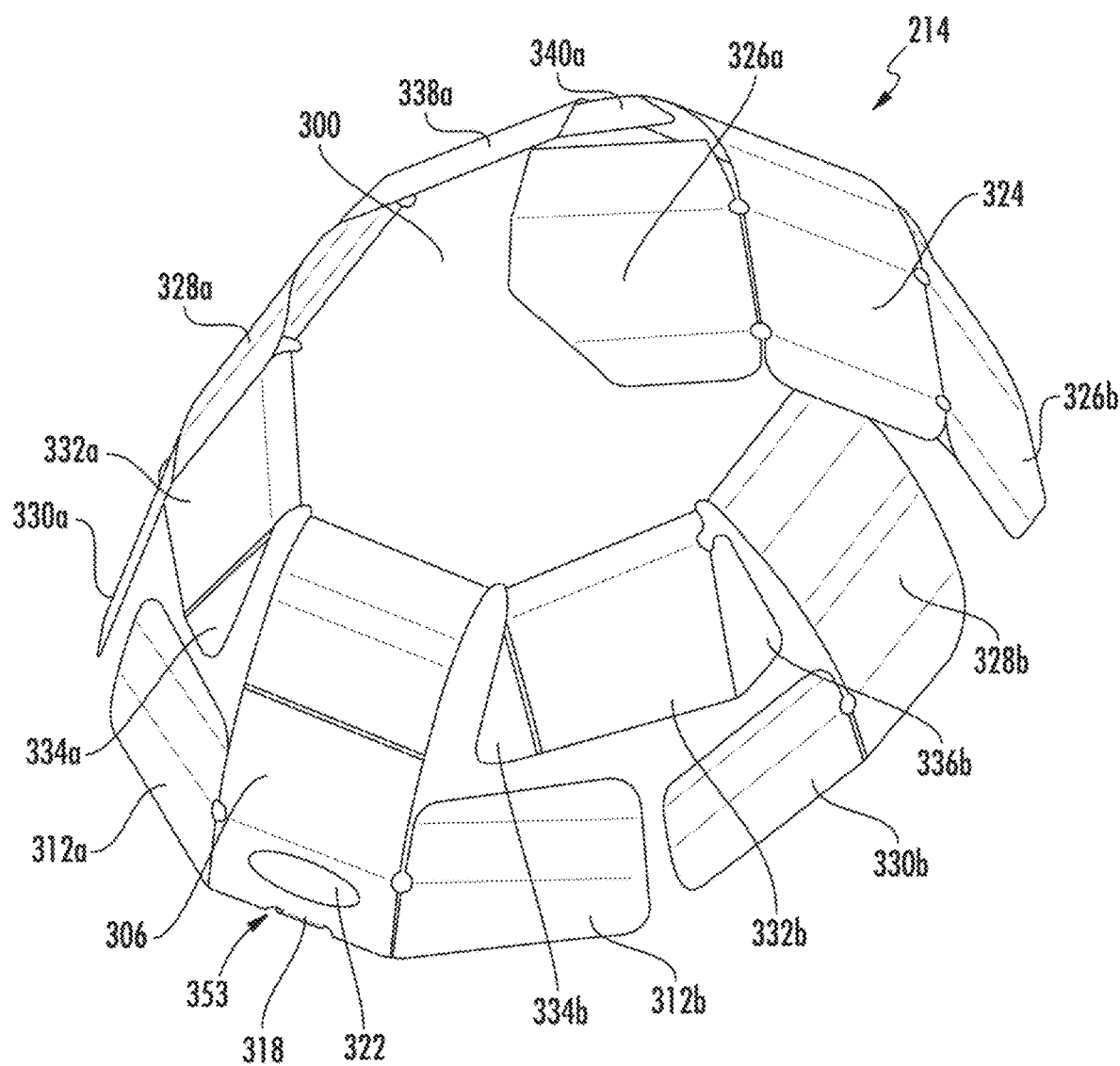
FIG. 12A is a bottom perspective view of the panel subassembly of FIG. 11A in a bent configuration with bends formed between various panels to form a concavity.
Figure 12B:
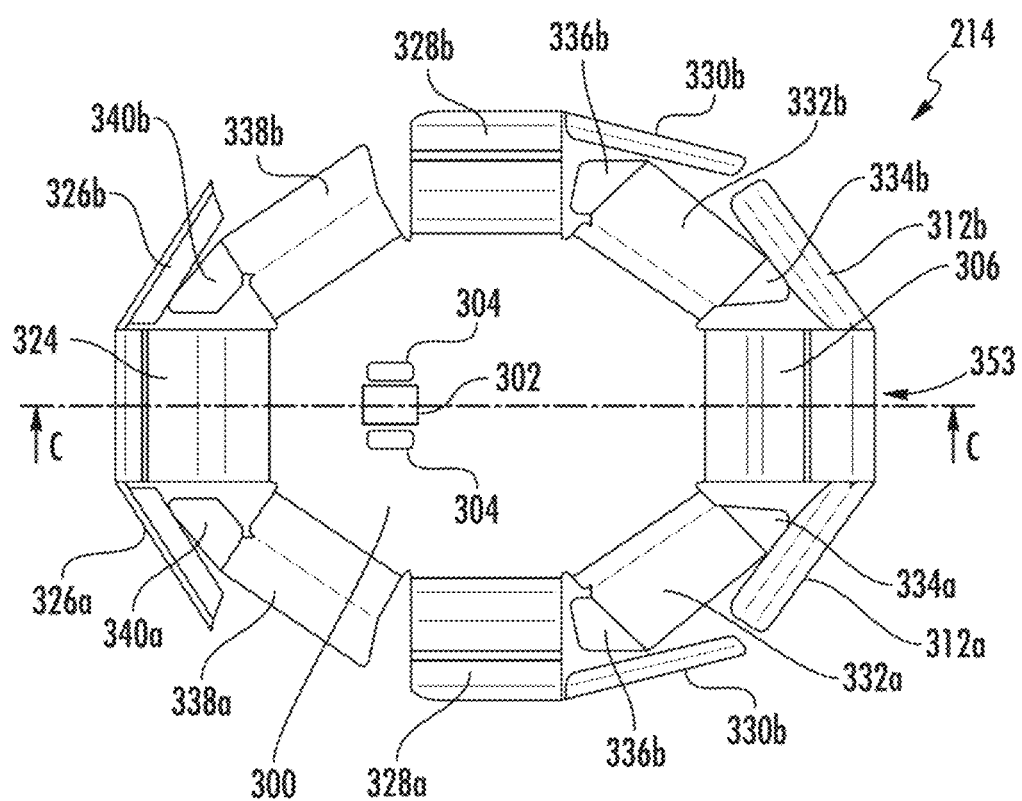
FIG. 12B is a bottom plan view of the panel subassembly of FIG. 12A in a bent configuration.
Figure 12C:
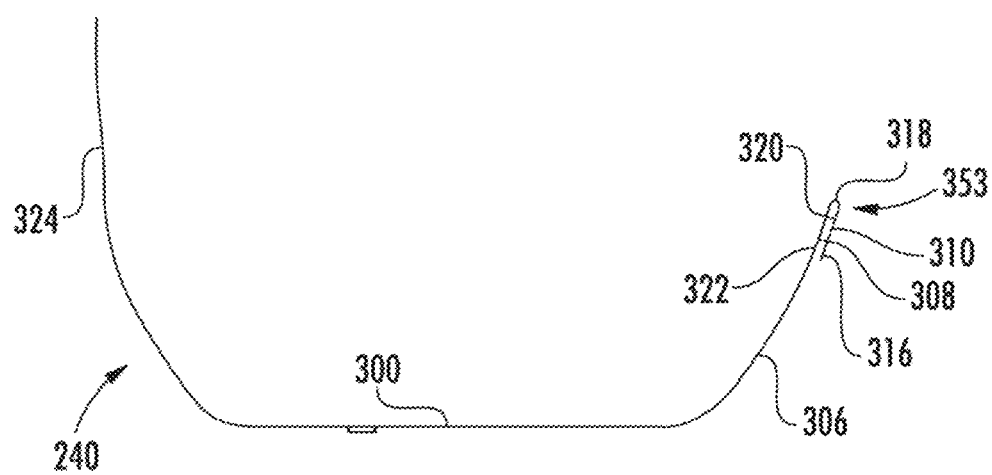
FIG. 12C is a side cross-sectional side view of the panel subassembly of FIGS. 12A and 12B in a bent configuration, taken along section line C-C illustrated in FIG. 12B.
Figures 12D, 12E:
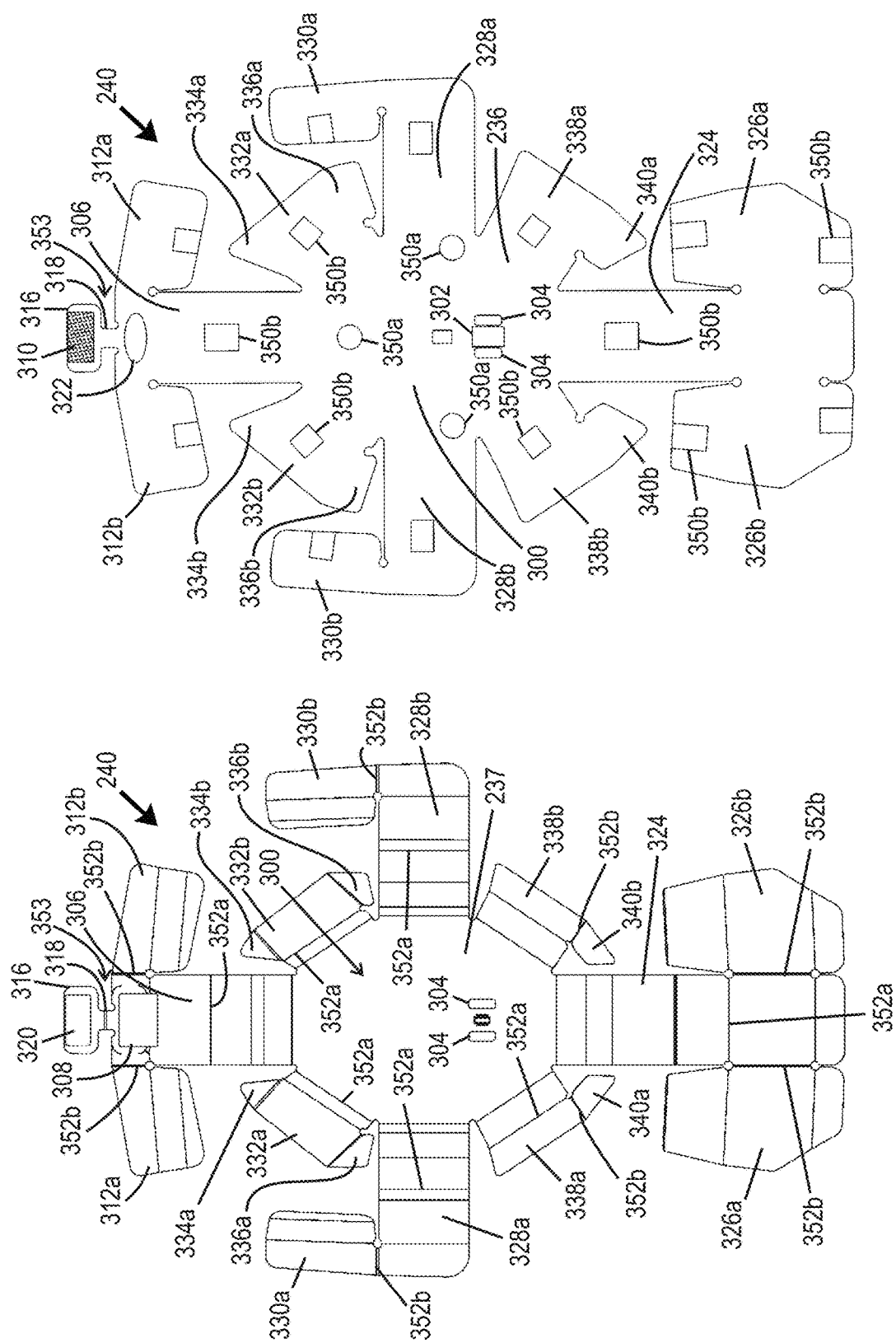
FIG. 12D is a top plan view of the panel subassembly of FIGS. 12A-12C in a flat configuration with illustration of inter-panel bending regions.
FIG. 12E is a bottom plan view of the panel subassembly of FIGS. 12A-12D in a flat configuration.

FIGS. 12A-12E illustrate the panel subassembly (also illustrated in FIGS. 11A-11C. More specifically, FIG. 12A is a bottom perspective view of the panel subassembly in a bent configuration, FIG. 12B is a bottom plan view of the panel subassembly in the bent configuration, FIG. 12C is a cross-sectional side view of the panel subassembly, FIG. 12D is a top plan view of the panel subassembly in a flat and fully expanded configuration with bending regions illustrated, and FIG. 12E is a bottom plan view of the panel subassembly in a flat and fully expanded configuration.

The panel subassembly 240 includes a plurality of interconnected FPCB panels that are able to bend and move (e.g., along reduced width regions or using hinge-like structurers) relative to one another to form varying dihedral angles. The panel subassembly 240 includes a body 300 (e.g., one or more body panels) with a stiffener section 302 positioned between two through slots 304. The through slots 304 receive the FPC snap lock engagement prongs 294 (shown in FIGS. 11A-11C and discussed above) and are aligned with the electronics subassembly control PCB prong apertures 282 and electronics subassembly mount prong receptacles 274, as explained above.

The body 300 includes multiple radially extending portions (e.g., a series of interconnected panels) positioned generally circumferentially around the peripheral edge of the body 300. More specifically, the body 300 includes a front extension 306, a rear extension 324 (extending opposite the front extension 306), a left extension 328a (positioned between and left of the front extension 306 and the rear extension 324), a right extension 328b (positioned between and right of the front extension 306 and the rear extension 324), a left front extension 332a (positioned between the front extension 306 and the left extension 328a), a left rear extension 338a (positioned between the rear extension 324 and the left extension 328a), a right front extension 332b (positioned between the front extension 306 and the right extension 328b), and a right rear extension 338b (positioned between the rear extension 324 and the right extension 328b). Each extension may comprise one or more panels that are separated by bending regions to permit bending or other relative movement permitted therebetween (e.g., forming varying dihedral angles).

The front extension 306 is attached to the body 300 at a proximal end, and a distal end thereof (opposite the proximal end) includes a stiffener section 308 and a capacitive touch active pad 322. The stiffener section 308 is provided at distal surface 237 (e.g., top surface), and the capacitive touch active pad 322 is provided at a proximal surface 236 (e.g., bottom surface), with the stiffener section 308 and capacitive touch active pad 322 opposing but being aligned with one another. The front extension 306 further includes a left flap 312a attached at a left side of the distal end of the front extension 306, and a right flap 312b attached at a right side of the distal end of the front extension 306.

A capacitive tab 316 is attached to the distal end of the front extension 306 by a neck 318. The capacitive tab 316 includes a stiffener section 320 on the distal surface 237 and a signal guard 310 on the proximal surface 236, with the stiffener section 320 and the signal guard 310 being arranged opposite to but aligned with one another. The capacitive tab 316 can bend outwardly by the neck 318 such that the capacitive tab stiffener section 320 and the front extension stiffener section 308 contact each other. In such a configuration, the capacitive tab stiffener section 320, signal guard 310, front extension stiffener section 308 and front extension capacitive touch active pad 322 are aligned with one another. In an alternative embodiment, the capacitive tab 316 may bend inwardly by the neck 318. In such a configuration, the extension stiffener section 308 and the capacitive tab stiffener section 320 may be arranged along a proximal surface, the front extension 306 may include a signal guard at a distal surface, and the capacitive tab 316 may include a capacitive touch active pad at a distal surface.

The rear extension 324 is attached to the body 300 at a proximal end and includes a left flap 326a and right flap 326b at a distal end. The left extension 328a is attached to the body 300 at a proximal end and includes a forward flap 330a at a distal end. The right extension 328b is attached to the body 300 at a proximal end and includes a forward flap 330b at a distal end. The left front extension 332a is attached to the body 300 at a proximal end and includes a forward flap 334a and a rearward flap 336a at a distal end. The left rear extension 338a is attached to the body 300 at a proximal end and includes a rearward flap 340a at a distal end. The right front extension 332b is attached to the body 300 at a proximal end and includes a forward flap 334b and a rearward flap 336b at a distal end. The right rear extension 338b is attached to the body 300 at a proximal end and includes a rearward flap 340b at a distal end.

The extensions and flaps may each include one or more panels and/or bending regions 352a, 352b. More specifically, as shown in FIG. 12D, the extensions and flaps may each include one or more horizontal bending regions 352a (e.g., bending transverse to a radius of the body 300). At least a portion of each extension may be connected to at least a portion of a respective flap by a vertical bending region 352b (bending along a radius of the body 300). The bending regions 352a, 352b allow the panel subassembly 240 to conform to the shape of the patient's head (e.g., the vertical bending regions 352b conform the panel subassembly 240 to the circumference of the patient's head). The flaps may attach to their respective extensions along an entire side of the flap or a portion thereof.

The panel subassembly 240 includes a plurality of keep-out areas 350a, 350b on the proximal surface 236 thereof. When the FPCB assembly 214 and flexible lenticular lens 216 are assembled together, the keep-out areas 350a, 350b generally align with (and are larger than) the distal ends 264 of the plurality of standoffs 218a, 218b to protect the circuitry of the panel subassembly 240, and to prevent standoffs 218a, 218b from contacting light emitters mounted to the panel assembly 240. More specifically, top keep out areas 350a align with and contact top standoffs 218a, and side keep-out areas 350b align with and contact side standoffs 218b. In certain embodiments, the panel subassembly 240 may include an encapsulant layer.

Figure 12F:
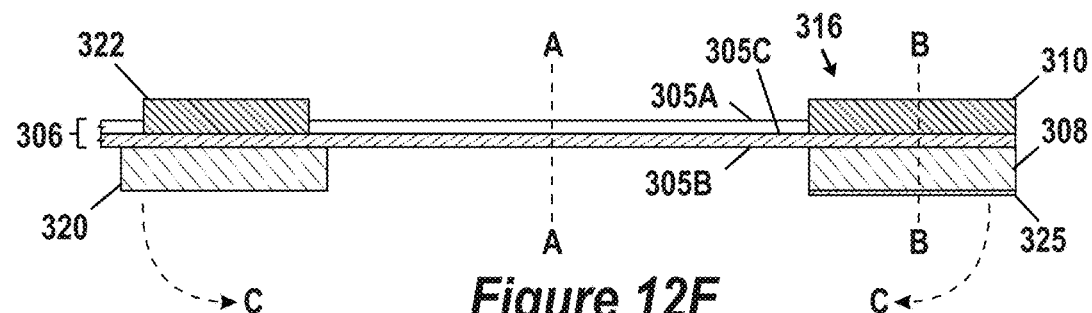
FIG. 12F is a cross-sectional view of a flexible printed circuit board (FPCB) incorporating elements for fabricating a capacitor prior to folding of the FPCB and adhesion of the capacitor elements.
Figure 12G:
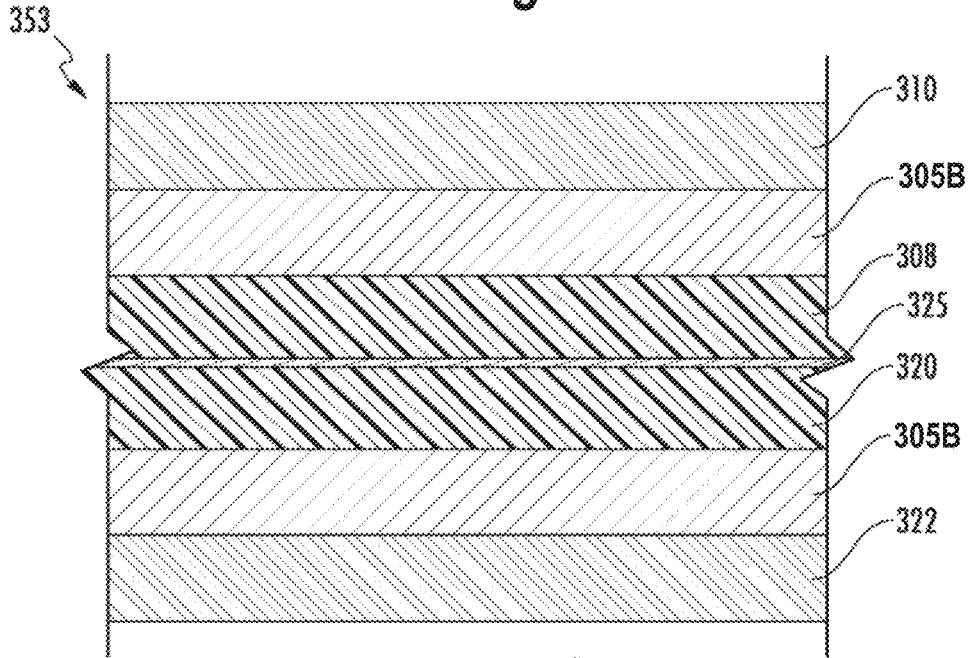
FIG. 12G is a cross-sectional view (taken along section line B-B in FIG. 12F) of a capacitor fabricated from the FPCB and elements shown in FIG. 12F, including flexible printed circuit board elements and intervening spacer elements.
Figure 12H:
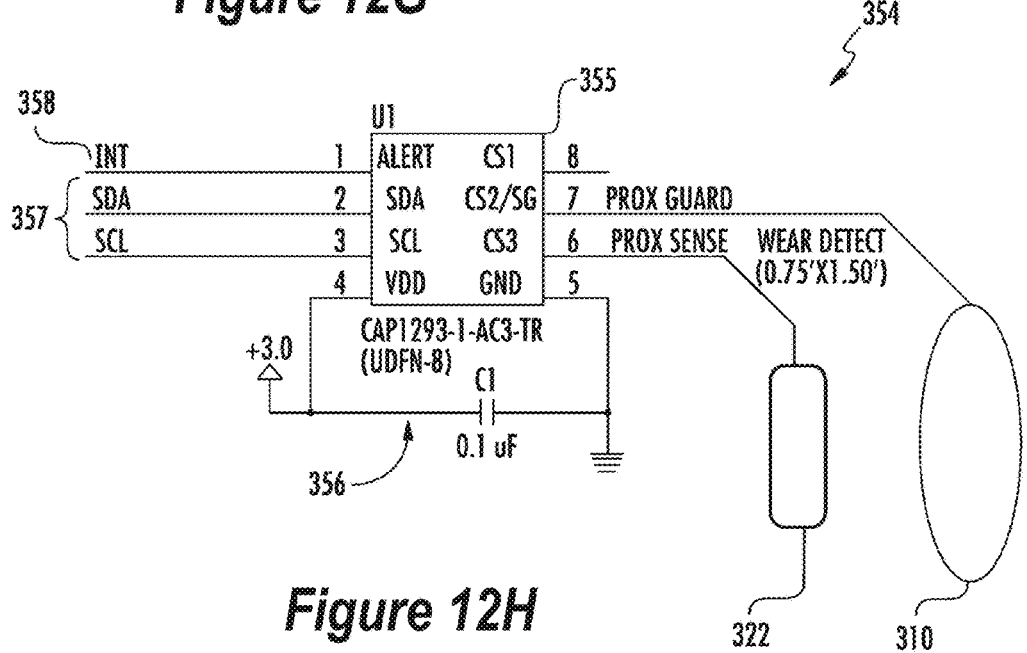
FIG. 12H is a circuit diagram for a proximity sensor including an integrated circuit chip and a capacitor according to FIG. 12G.

FIGS. 12F-12H illustrate a capacitor. More specifically, FIG. 12F is a cross-sectional view of a flexible printed circuit board (FPCB) incorporating elements for fabricating a capacitor prior to folding of the FPCB (in the direction of curved arrows C, along fold line A-A) and adhesion of the capacitor elements. FIG. 12F illustrates a copper layer 305C arranged between a cover layer 305A and a carrier (e.g., polyimide) layer 305B of a FPCB 306 (which may be embodied in a front extension panel), with a capacitive touch active pad 322 and a signal guard 310 further mounted to the FPCB 306 (preferably over a first surface of the carrier layer 305B, and in electrical communication with traces formed by the copper layer 305A). A front extension stiffener section 308 and a capacitive tab stiffener section 320 are provided along a second surface of the carrier layer 305B, proximate to the signal guard 310 and the capacitive touch active pad 322, respectively. Adhesive (or double-sided adhesive tape) 325 is arranged along one or more of the stiffener sections 308, 320 to provide non-conductive adhesion therebetween when the FPCB is folded in the direction of curved arrow C along fold line A-A. FIG. 12G is a cross-sectional view of a capacitor 353 fabricated from the FPCB 306 and elements shown in FIG. 12F, following folding of the FPCB 306 and adhesion between the stiffener sections (or spacer elements) 308, 320. In certain embodiments, a portion of the FPCB 306 extending forward of the fold line A-A may embody a capacitive tab 316 that is continuous with the remainder of the FPCB 306. In other embodiments, the capacitive tab 316 may embody a second FPCB panel that is discontinuous relative to the FPCB 306.

In certain embodiments, the capacitor 353 shown in FIG. 12G comprises the front extension 306 (which may be embodied in a front extension panel, first FPCB panel, first FPCB element, etc.), the front extension stiffener section 308 (e.g., first stiffener section), the front extension capacitive touch active pad 322 (e.g., capacitive pad), the carrier layer 305B (which may be embodied in a capacitive tab 316 or capacitive tab panel, second FPCB panel, second FPCB element, etc.), the capacitive tab stiffener section 320 (e.g., the second stiffener section), the signal guard 310 (e.g., signal ground hatch), and an adhesive (or double-sided adhesive tape) 325 positioned between the front extension stiffener section 308 and the capacitive tab stiffener section 320. The front extension stiffener section 308, capacitive tab stiffener section 320, and adhesive (or double-sided adhesive tape) 325 provide non-conductive separation between the front extension capacitive touch active pad 322 and the signal guard 310. As shown in FIG. 12G, the carrier layer 305B (e.g., 0.1 to 1.5 mm thick), front extension stiffener section 308 (e.g., 0.25 to 2.5 mm thick), capacitive tab stiffener section 320 (e.g., 0.25 to 2.5 mm thick), and adhesive (or double-sided adhesive tape) 325 (e.g., 0.01 to 0.25 mm) together define a distance (e.g., predetermined distance, d in Equation 1 below) between the front extension capacitive touch active pad 322 and the signal guard 310 which corresponds with a predetermined capacitive value, such as shown below:

$$C = \left(\frac{0.0885 \times E_r(L \times W)}{d}\right) \quad \text{Equation 1}$$

In Equation 1, L is the length of the conductive elements, W is the width of the conductive elements, $E_r$ is the relative dielectric constant, and d is the dielectric thickness between the conductive elements. In one embodiment, the length is about 3.0 cm, the width is about 2.0 cm, and the thickness is about 0.75 to 1.00 mm. This provides a capacitance for the capacitor 353 of about 25 to 33 pF. In certain embodiments, the signal guard 310 may have a lateral dimension (e.g., width) that exceeds lateral dimensions of the front extension capacitive touch active pad 322 by 20% to 40%. The first and second FPCB panels may comprise polyimide, and the first and second stiffener sections may have a dielectric constant between 2.5 and 5 (e.g., between 4 and 4.5)

It is noted that a single stiffener may be used instead of two stiffeners. For example, the front extension stiffener section 308 may be twice as thick, such that a capacitive tab stiffener section 320 is not needed. The stiffeners (e.g., non-conductive spacers) may be any non-conductive material (e.g., foam, PCB, etc.), and may be attached to their respective FPCB element by a fastener or adhesive (e.g., glue, tape, etc.). The adhesive 325 may be applied on at least a portion of the front extension stiffener section 308 and/or the capacitive tab stiffener section 320. Additionally, any type of adhesive 325 could be used (e.g., double-sided tape, glue, etc.), and other types of attachment could be used other than adhesive 325, such as a fastener (e.g., screw, nail, etc.). In such circumstances, the adhesive 325 could be omitted.

In certain embodiments, the capacitor 353 may be used as a proximity sensor (e.g., capacitive sensor), such that the phototherapy device 210 can determine whether the phototherapy device 210 is proximate to a patient's forehead by a change in capacitance and/or voltage (e.g., due to interaction with an electric field proximate to a patient's skin). In certain embodiments, the patient's skin can alter the capacitance (and resulting voltage) from a short distance away without requiring contact with the capacitor 353.

The panels of the panel subassembly 240, as a flex circuit, are very thin (e.g., about 0.10 mm or less). This thickness is generally too thin to provide appropriate capacitance values for a proximity sensor, since capacitance would be too high. Accordingly, folding the capacitive tab 316 aligns the signal guard 310 with the front extension capacitive touch active pad 322, and a minimum distance therebetween is maintained by the front extension stiffener section 308, capacitive tab stiffener section 320, and/or adhesive 325 which preferably embody dielectric materials. Thus, a larger distance is created between these two conductive plates (e.g., signal guard 310 and the front extension capacitive touch active pad 322), and the capacitance value is modified. Optionally, capacitance values may be further adjusted by adding material layers (e.g., double sided adhesive tape 325) between the two plates (e.g., signal guard 310 with the front extension capacitive touch active pad 322), with such added material preferably serving as a dielectric.

In certain embodiments, the capacitor 353 provides directional sensing functionality such that only the capacitance of the front extension capacitive touch active pad 322 is altered by the proximity of skin thereto. In certain embodiments, the signal guard 310 may be configured to be driven in polarity opposite from that of the front extension capacitive touch active pad 322, and the signal guard 310 may be larger in size than the front extension capacitive touch active pad 322 to extend beyond the margins of the front extension capacitive touch active pad 322. This ensures that proximity of skin to the signal guard 310 does not change capacitance of the front extension capacitive touch active pad 322. In other words, the front extension capacitive touch active pad 322 is configured to sense capacitance changes (due to skin proximity) that originate from inside the phototherapy device 210, and the signal guard 310 prevents the detection of a false proximity signal (e.g., from capacitance changes that originate from sources outside the phototherapy device 210). This prevents a patient touching the exterior (e.g., capacitive tab 316) of the phototherapy device 210 from triggering operation of the phototherapy device 210. The phototherapy device 210 will only be triggered from wearing the phototherapy device 210 (e.g., because the patient's skin will modify capacitance of the capacitor 353). The front extension signal guard 310 may be patterned (e.g., in a hatch, mesh, etc.) with copper to form a Faraday cage to insulate the front extension capacitive touch active pad 322, which may include a continuous (e.g., solid copper) conductive surface.

FIG. 12H shows a circuit 354 of the capacitor 353 (or proximity sensor). The circuit 354 includes a capacitive touch controller 355 (e.g., microcontroller) which may be an integrated circuit (IC). The circuit 354 may be connected to the front extension capacitive touch active pad 322, the signal guard 310, and a power circuit 356 (including a positive supply voltage and ground). Further, the circuit 354 may be connected to one or more data sources 357 (e.g., serial data line (SDA), serial clock line (SCL), etc.), and interrupt 358 (INT). When the interrupt 358 is triggered, the interrupt 358 sends a signal to the motherboard to bring the motherboard from a sleep state (e.g., for power saving) to an active state. In the active state, the motherboard may check for wireless (e.g., Bluetooth) signals and/or electrical connections, check the account (e.g., status), and/or enable operation of the phototherapy device 210. In certain embodiments, the circuit 354 may remain continuously active and provide feedback to the controller, such that the interrupt 358 is triggered when the voltage and/or capacitance exceeds a predetermined value (e.g., between 12-50 pF), such as resulting from a change in capacitance of the capacitor 353. In certain embodiments, the sensitivity threshold may be adjusted via the capacitive touch controller 355.

Figure 13B:
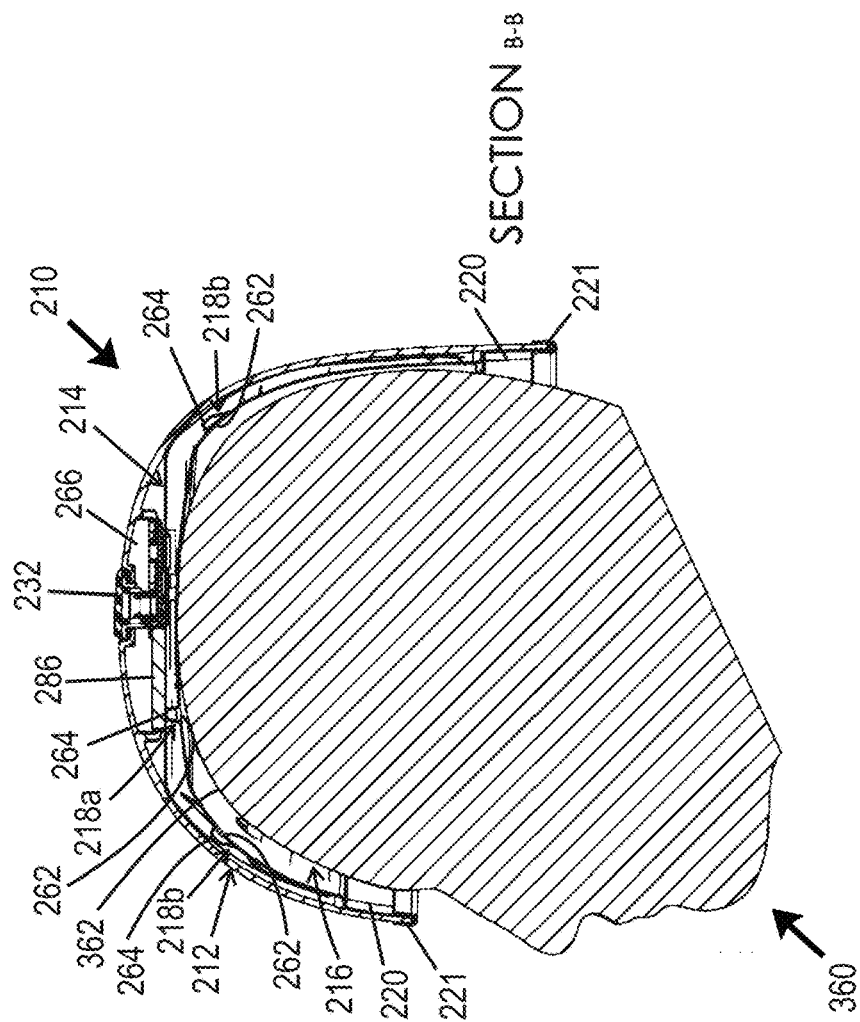
FIG. 13B is a cross-sectional side view of the patient and phototherapy device of FIG. 13A, taken along section line B-B illustrated in FIG. 13A.
Figure 13A:
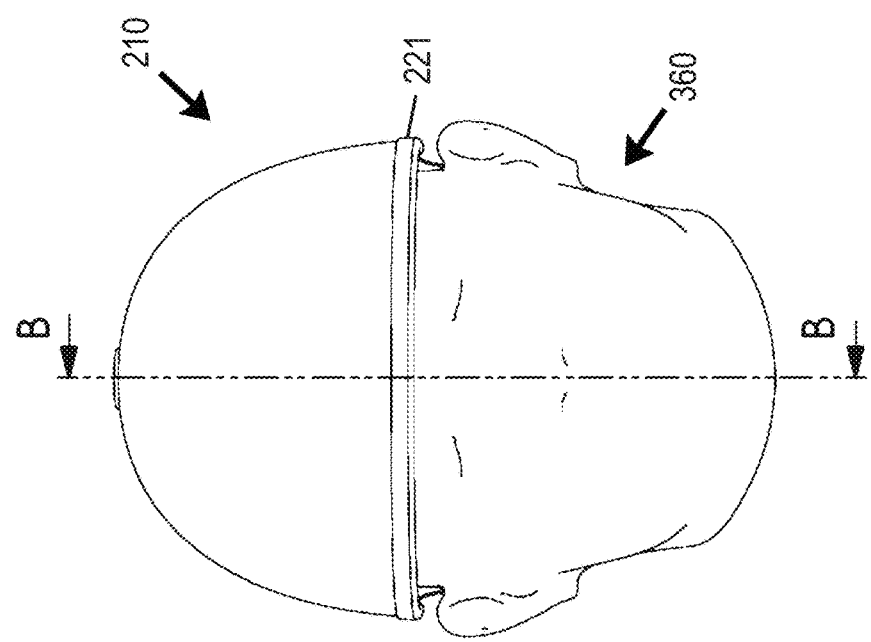
FIG. 13A is a front elevation view of a patient wearing a phototherapy device according to FIGS. 10A-10E.

FIGS. 13A and 13B illustrate a patient wearing and using the phototherapy device 210 of FIGS. 10A-10E. More specifically, FIG. 13A is a front elevation view of a patient wearing the phototherapy device 210, and FIG. 13B is a cross-sectional side view of the patient wearing the phototherapy device 210. As shown, the front of the phototherapy device 210 is positioned above the patient's eyes, and the rear of the phototherapy device 210 (e.g., the posterior extensions) extends along the lower back of the head, such that a front bottom edge and a rear bottom edge of the phototherapy device 210 are at two different heights when in use. This allows the phototherapy device 210 to increase the coverage area of the phototherapy device 210 to cover desired hair-producing areas of a scalp of the patient 360. As discussed above, the flexible cap 212, FPCB assembly 214, and flexible lenticular lens 216 may be adjustable in size and shape (e.g., the circumference can vary) to accommodate various users. For example, an inner circumference may vary from 54 cm to 64 cm.

In use, the LEDs of the phototherapy device 210 provide therapeutic light emissions to a scalp 362 of the patient 360. More specifically, the LEDs mounted on the FPCB assembly proximal surface 236 transmit light through the flexible lenticular lens 216, which defocuses the light emissions to increase the uniform distribution of light emissions across the patient's scalp 362. Although a flexible lenticular lens 216 is used in certain embodiments, other light-transmissive materials or layers including diffusers may be used. The flexible lenticular lens 216 is preferably positioned a predetermined distance from the LEDs for optimal light emission distribution and performance (e.g., avoiding positioning the LEDs too far or too near from the flexible lenticular lens 216), and to maintain a safe distance between the patient's scalp 362 and the LEDs (e.g., from the heat generated by the LEDs). This distance (e.g., 3.5 mm between LEDs and flexible lenticular lens 216 in certain embodiments) is maintained by the plurality of standoffs 218a, 218b, where gravity naturally encourages the FPCB assembly 214 towards the flexible lenticular lens 216 and the plurality of standoffs 218a, 218b contact the FPCB assembly 214 to maintain a minimum distance therebetween (for LED protection, for optical optimization, and/or for thermal separation from a patient's scalp).

In certain embodiments, the LEDs may provide one or more peak wavelengths (e.g., red light emission and/or blue light emission), such as about 620 nm to 660 nm and/or 660 nm to 670 nm, etc. For example, the plurality of LEDs may include LEDs producing peak wavelengths of about 420 nm and 620 nm, or 420 nm and 660 nm, or 420 nm, 625 nm, and 660 nm.

Figure 14A:
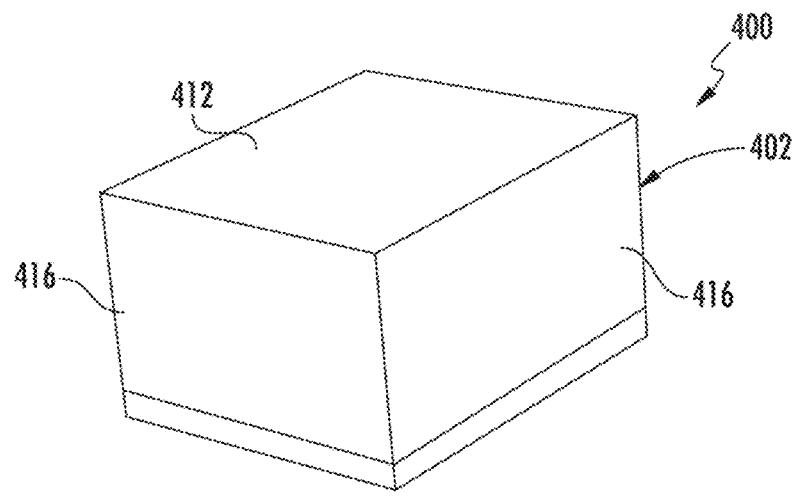
FIG. 14A is an upper perspective view of a package containing a phototherapy device according to FIGS. 10A-10E.
Figure 14B:
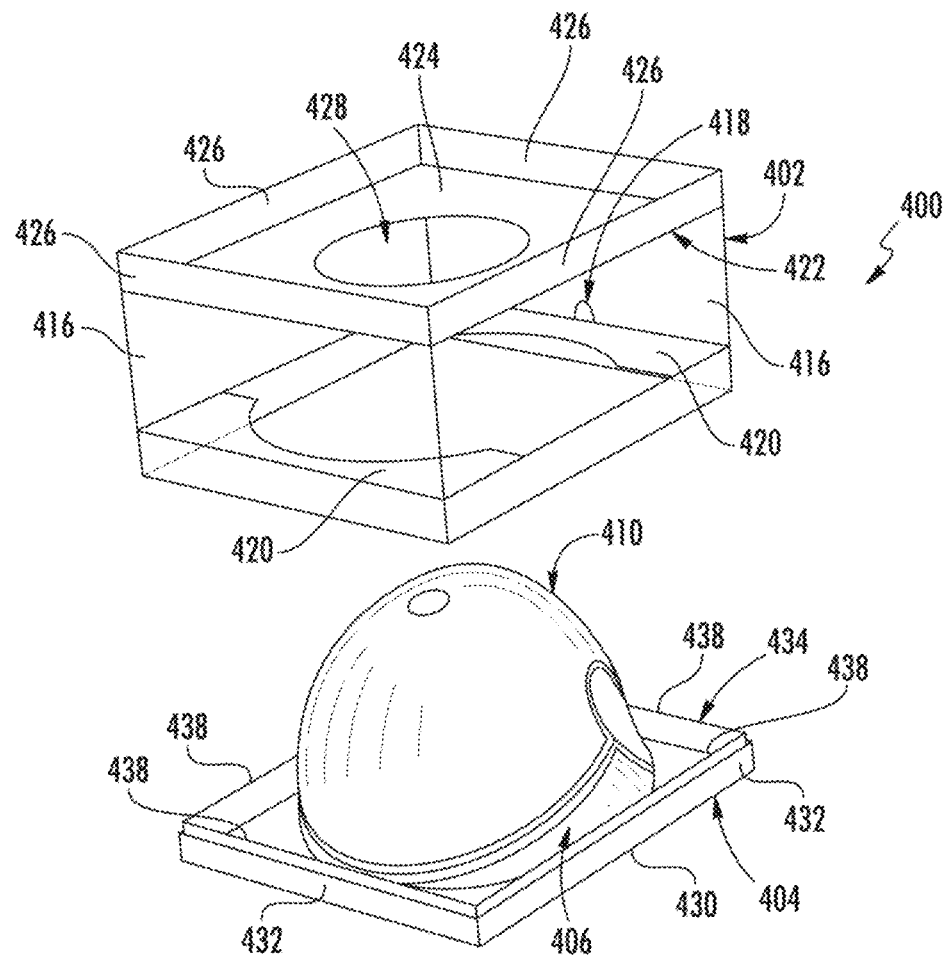
FIG. 14B is an exploded perspective view of the package and phototherapy device of FIG. 14A following removal of a top cover from a bottom lid of the package.
Figure 14C:
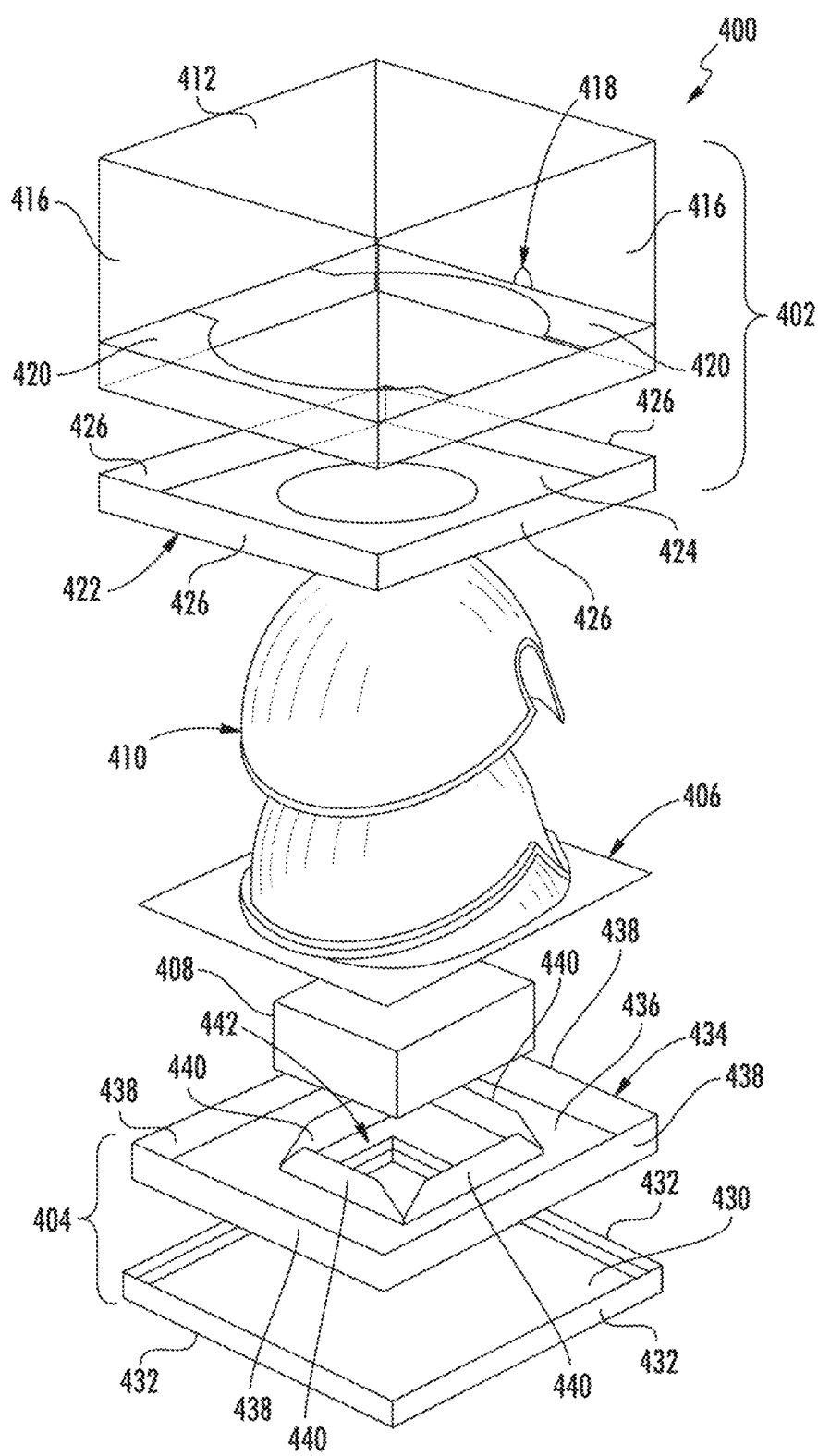
FIG. 14C is an exploded view of the package with the phototherapy device of FIGS. 14A and 14B, according to one embodiment.
Figure 14D:
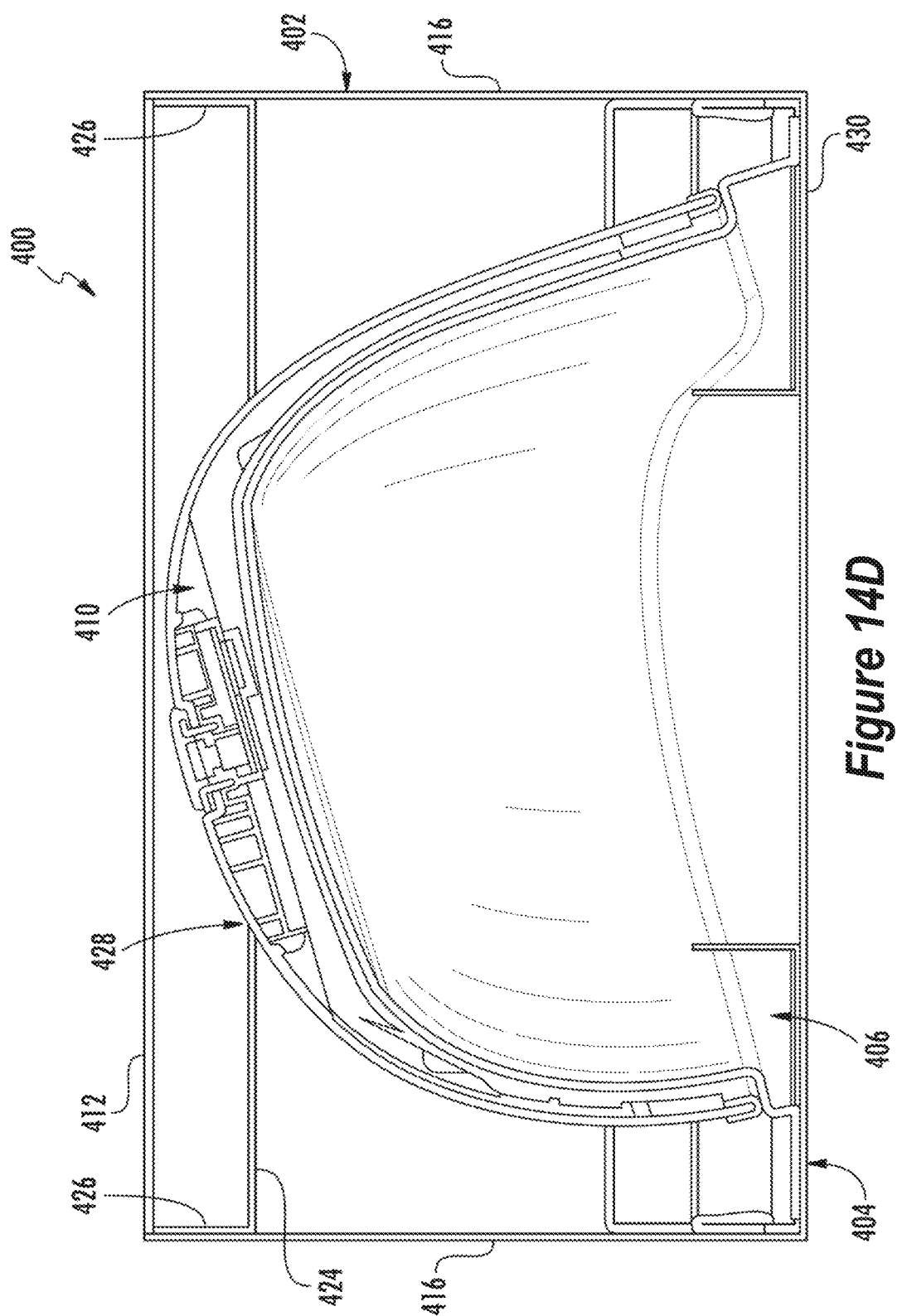
FIG. 14D is a side cross-sectional view of the packaged phototherapy device of FIGS. 14A-14C.

FIGS. 14A-14D are views of a package and a phototherapy device. More specifically, FIG. 14A is an upper perspective view of a package containing a phototherapy device. FIG. 14B is an exploded perspective view of the package and phototherapy device following removal of the top cover from the bottom lid (with the top cover being transparent for illustrative purposes). FIG. 14C is an exploded view of the package with the phototherapy device of FIGS. 14A and 14B (with the top cover being transparent for illustrative purposes). FIG. 14D is a side cross-sectional view of the packaged phototherapy device. The packaged device 400 includes a top cover 402, a bottom lid 404, a charging base 406 therebetween, and an accessory box 408 positioned between the bottom lid 404 and the charging base 406, wherein a phototherapy device 410 is positioned on the charging base 406 between the charging base 406 and the top cover 402.

The top cover 402 may be provided in various shapes and sizes. In certain embodiments, the top cover 402 may include a top wall 412 with sidewalls 416 extending downwardly from a perimeter thereof. In certain embodiments, a sidewall may include a cord hole punch 418 to receive an electronic connector therethrough for connection with the phototherapy device 410. In certain embodiments, the top cover 402 may include one or more positioning flaps 420 located proximate to (but a distance from) an opening of the top cover 402 to provide sufficient clearance to receive a portion of the bottom lid 404. The positioning flaps 420 help stabilize the phototherapy device 410 and prevent lateral movement thereof. In certain embodiments, the top cover 402 may include an insert 422 having a bottom wall 424 and sidewalls 426 extending upwardly from a perimeter thereof. The insert 422 includes a clearance hole 428 in an approximate center thereof to receive a portion of a top of the phototherapy device 410 therein. Thus, the top cover insert 422 prevents lateral movement of the phototherapy device 410, and secures the phototherapy device 410 between the insert 422 and the charging base 406.

The bottom lid 404 may be provided in various shapes and sizes. The bottom lid 404 may include a bottom wall 430 with sidewalls 432 extending upwardly from a perimeter thereof. In certain embodiments, the bottom lid 404 may include an insert 434 having a bottom wall 436, exterior walls 438 along an outer perimeter thereof, and interior walls 440 along an interior perimeter thereof and defining an interior aperture 442 (extending through the bottom wall 436). In certain embodiments, the insert exterior walls 438 may be taller than the bottom lid sidewalls 432, such that the insert exterior walls 438 contact the interior of the top cover sidewalls 416 (to frictionally secure the top cover 402 thereto and to prevent lateral movement therebetween). The bottom lid insert interior walls 440 may receive the accessory box 408 therein (to frictionally secure the accessory box 408 thereto and to prevent lateral movement therebetween). The accessory box 408 may include a headliner pack, USB cable, AC adaptor, etc.

Figure 15A:
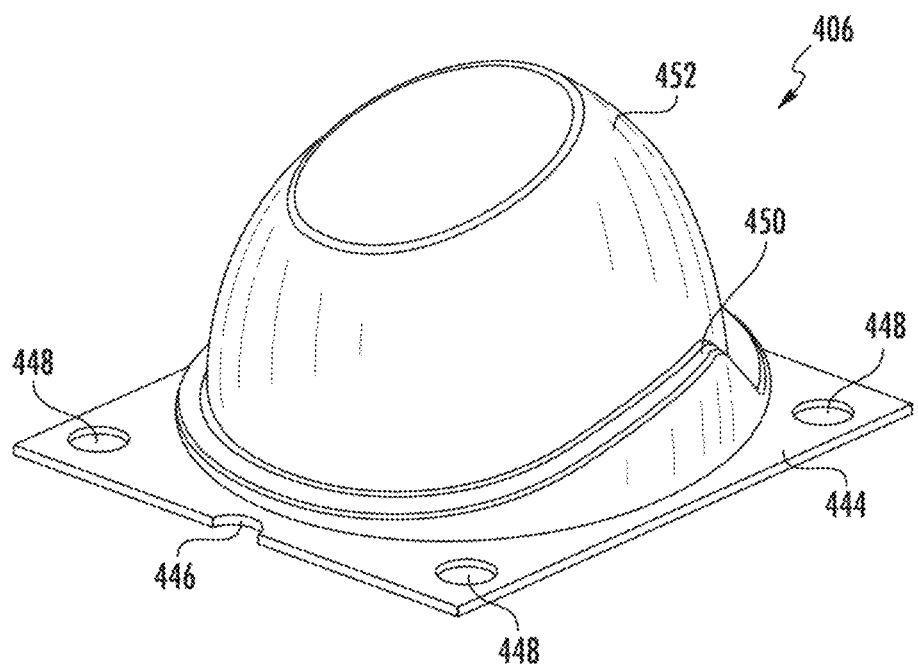
FIG. 15A is an upper perspective view of a charging base portion of the packaged phototherapy device of FIGS. 14A-14D.
Figure 15B:
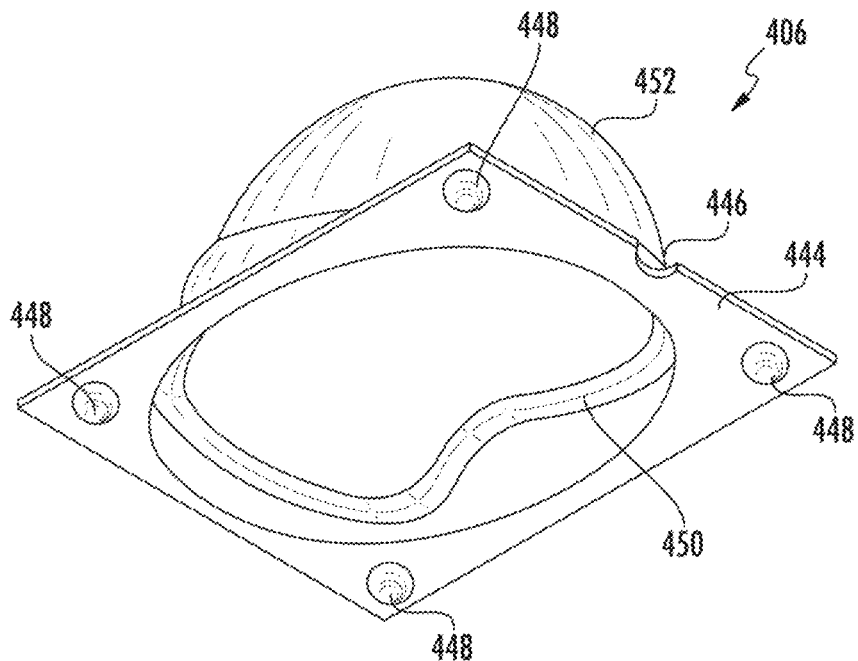
FIG. 15B is a lower perspective view of the charging base of FIG. 15A.
Figure 15C:
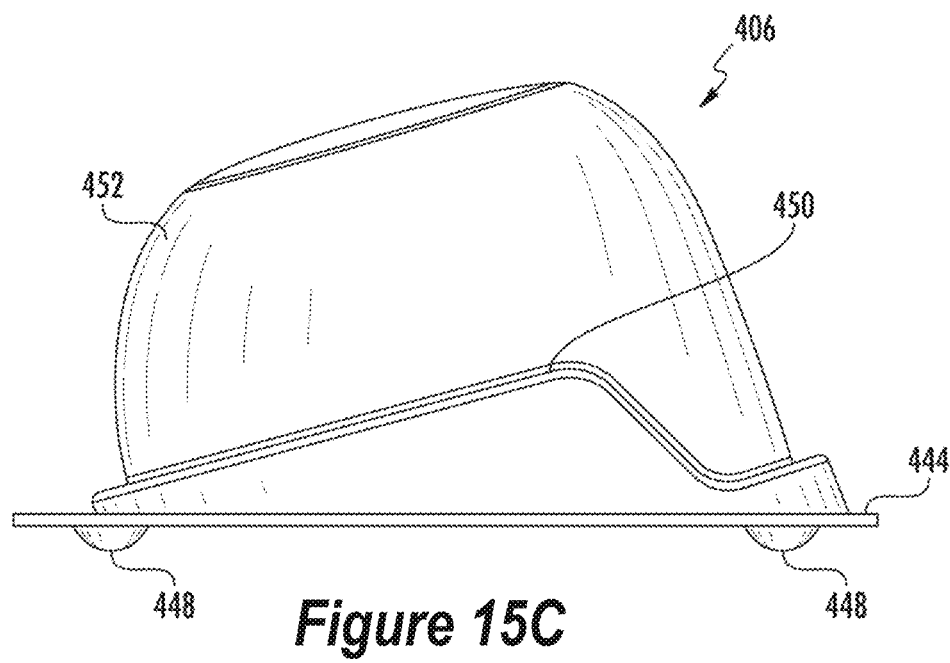
FIG. 15C is a side elevation view of the charging base of FIGS. 15A and 15B.
Figure 15D:
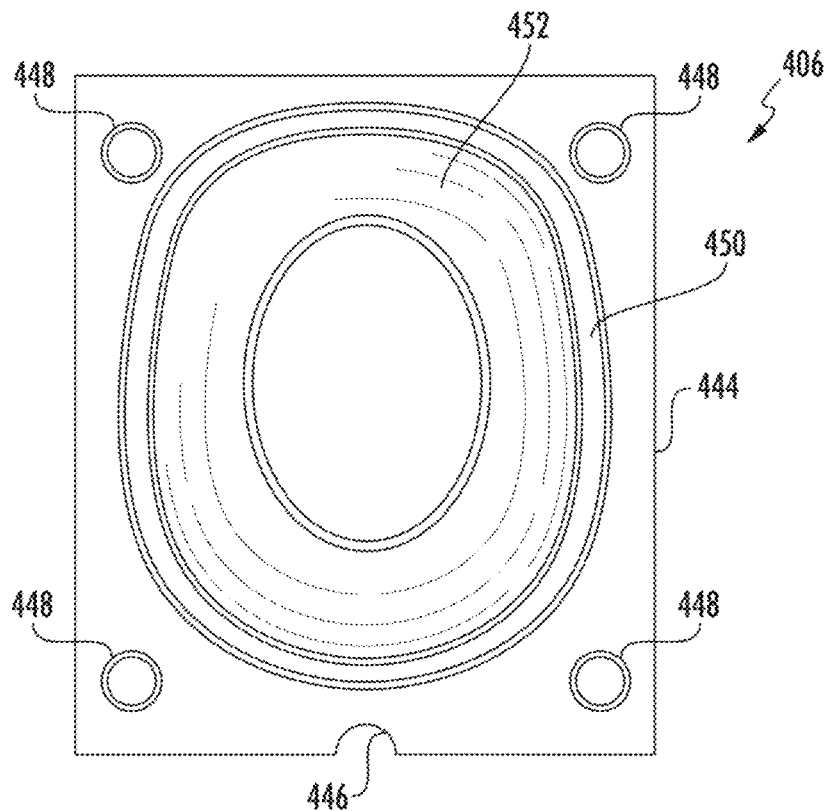
FIG. 15D is a top plan view of the charging base of FIGS. 15A-15C.

FIGS. 15A-15D are views of the charging base 406. More specifically, FIG. 15A is an upper perspective view of the charging base of the packaged phototherapy device, FIG. 15B is a lower perspective view of the charging base, FIG. 15C is a side elevation view of the charging base, and FIG. 15D is a top plan view of the charging base. The charging base 406 may include a foundation 444 of a complimentary shape to that of the bottom lid insert exterior walls 438 (to frictionally secure the charging base 406 thereto and to prevent lateral movement therebetween). In certain embodiments, the charging base 406 may include a notch 446 in a front edge of the foundation 444 to facilitate removal of the charging base 406 from the bottom lid 404 (shown in FIGS. 14A-14D and discussed above). In certain embodiments, the charging base 406 may include one or more feet 448 extending from a bottom surface of the charging base 406. The feet 448 may be integrally formed with the foundation 444 or attached thereto.

The foundation 444 has a contoured top 452 (e.g., convex top) that generally conforms to the shape of the proximal surface of the phototherapy device 410, and the foundation 444 may include a lip 450 that generally conforms to the peripheral edge of the phototherapy device 410. Accordingly, the contoured top 452 and lip 450 of the charging base 406 stabilizes the phototherapy device 410 when placed thereon. Further, the contoured top 452 receives the accessory box 408 within an interior defined by the contoured top 452. The charging base 406 may be used to hold the phototherapy device 410 when not in use and/or when charging, thereby supporting the phototherapy device 410 in a protected manner and preventing it from being distorted in shape. In certain embodiments, the charging base 406 may provide wireless inductive charging of the phototherapy device 410 through the contoured top 452 when the phototherapy device 410 is positioned thereon.

Those skilled in the art will recognize improvements and modifications to the preferred embodiments of the present disclosure. All such improvements and modifications are considered within the scope of the concepts disclosed herein and the claims that follow.

What is claimed is:

1. A phototherapy device for delivering light emissions to a scalp of a patient, comprising:
    a flexible lenticular lens comprising a proximal lens surface and a distal lens surface, wherein the flexible lenticular lens is generally sized and shaped to a head of the patient;
    a flexible printed circuit board (FPCB) including at least one light emitting device on a proximal surface thereof; and a plurality of standoffs positioned between the distal lens surface and the FPCB to maintain a minimum distance between the at least one light emitting device and the distal lens surface, wherein the phototherapy device is configured to transmit light emissions generated by the at least one light emitting device through the flexible lenticular lens to the scalp of the patient.

2. The phototherapy device of claim 1, wherein a distance from a proximal end of each standoff of the plurality of standoffs to the proximal lens surface of the flexible lens exceeds a thickness of the flexible lens.

3. The phototherapy device of claim 1, wherein light emissions of the at least one light emitting device are within a range of about from 620 nm to 700 nm.

4. The phototherapy device of claim 1, wherein the FPCB is arranged to accommodate outward expansion and inward contraction.

5. The phototherapy device of claim 1, wherein the at least one light emitting device comprises a non-coherent light emitting device.

6. The phototherapy device of claim 1, wherein the at least one light emitting device comprises a first array of light emitting devices arranged to generate light having a first peak wavelength and a second array of light emitting devices arranged to generate light having a second peak wavelength, wherein the second peak wavelength differs from the first peak wavelength by at least 20 nm.

7. The phototherapy device of claim 6, wherein the first peak wavelength and the second peak wavelength are selected from one of the following combinations (a) to (f): (a) the first peak wavelength is in a range of from 615 nm to 635 nm and the second peak wavelength is in a range of from 650 nm to 670 nm; (b) the first peak wavelength is in a range of from 520 nm to 540 nm and the second peak wavelength is in a range of from 650 nm to 670 nm; (c) the first peak wavelength is in a range of from 410 nm to 430 nm and the second peak wavelength is in a range of from 620 nm to 640 nm; (d) the first peak wavelength is in a range of from 410 nm to 430 nm and the second peak wavelength is in a range of from 650 nm to 670 nm; (e) the first peak wavelength is in a range of from 410 nm to 430 nm and the second peak wavelength is in a range of from 495 nm to 515 nm; or (f) the first peak wavelength is in a range of from 410 nm to 430 nm and the second peak wavelength is in a range of from 520 nm to 540 nm.

8. The phototherapy device of claim 1, further comprising a proximity sensor arranged to sense a condition indicative of placement of the phototherapy device proximate to the scalp of the patient, wherein at least one of initiation, termination, or modification of operation of the at least one light emitting device is responsive to an output signal of the proximity sensor.

9. The phototherapy device of claim 1, further comprising a temperature sensor arranged to sense a temperature condition on or proximate to a portion of the phototherapy device, wherein at least one of initiation of operation, deviation of operation, or termination of operation of the at least one light emitting device is responsive to an output signal of the temperature sensor.

10. The phototherapy device of claim 1, wherein the plurality of standoffs is integrally attached to the flexible lenticular lens.

11. The phototherapy device of claim 10, wherein the flexible lenticular lens and the plurality of standoffs are formed by molding.

12. The phototherapy device of claim 1, further comprising a communication module configured to electronically communicate with an electronic device external to the phototherapy device.

13. A method for treating at least one dermatological disorder, the method comprising placing the phototherapy device of claim 1 on a head of the patient, and energizing the at least one light emitting device to deliver light emissions to at least a portion of the scalp of the patient.

14. The phototherapy device for delivering light emissions to a scalp of a patient, comprising:
a flexible lenticular lens comprising a proximal lens surface and a distal lens surface, wherein the flexible lenticular lens is generally sized and shaped to a head of the patient;
a flexible printed circuit board (FPCB) including at least one light emitting device on a proximal surface thereof; and a plurality of standoffs positioned between the distal lens surface and the FPCB to maintain a minimum distance between the at least one light emitting device and the distal lens surface, wherein the phototherapy device is configured to transmit light emissions generated by the at least one light emitting device through the flexible lenticular lens to the scalp of the patient, wherein light emissions of the at least one light emitting device are within a range of about from 410 nm to 455 nm.

* * * * *